(12) United States Patent
Tabuteau

(10) Patent No.: US 10,413,561 B2
(45) Date of Patent: *Sep. 17, 2019

(54) NERIDRONIC ACID AND OTHER BISPHOSPHONATES FOR TREATING COMPLEX REGIONAL PAIN SYNDROME AND OTHER DISEASES

(71) Applicant: ANTECIP BIOVENTURES II LLC, New York, NY (US)

(72) Inventor: Herriot Tabuteau, New York, NY (US)

(73) Assignee: ANTECIP BIOVENTURES II LLC, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/366,818

(22) Filed: Mar. 27, 2019

(65) Prior Publication Data
US 2019/0216833 A1    Jul. 18, 2019

Related U.S. Application Data

(63) Continuation-in-part of application No. 16/110,869, filed on Aug. 23, 2018, which is a continuation-in-part of application No. 15/710,759, filed on Sep. 20, 2017, now Pat. No. 10,080,765, which is a continuation-in-part of application No.
(Continued)

(51) Int. Cl.
| | | |
|---|---|---|
| A61K 31/675 | (2006.01) | |
| A61K 9/20 | (2006.01) | |
| A61K 31/663 | (2006.01) | |
| A61K 45/06 | (2006.01) | |
| A61K 47/12 | (2006.01) | |

(Continued)

(52) U.S. Cl.
CPC .......... *A61K 31/675* (2013.01); *A61K 9/0053* (2013.01); *A61K 9/20* (2013.01); *A61K 9/2004* (2013.01); *A61K 9/2009* (2013.01); *A61K 9/2013* (2013.01); *A61K 9/2027* (2013.01); *A61K 9/2054* (2013.01); *A61K 9/28* (2013.01); *A61K 31/663* (2013.01); *A61K 45/06* (2013.01); *A61K 47/12* (2013.01)

(58) Field of Classification Search
CPC .................................................. A61K 31/663
See application file for complete search history.

(56) References Cited

U.S. PATENT DOCUMENTS

| 4,822,609 A | 4/1989 | Flora |
|---|---|---|
| 4,939,130 A | 7/1990 | Jaeggi et al. |

(Continued)

FOREIGN PATENT DOCUMENTS

| CN | 101259133 | 3/2008 |
|---|---|---|
| EP | 1057488 | 12/2000 |

(Continued)

OTHER PUBLICATIONS

U.S. Appl. No. 15/710,759, filed Sep. 20, 2017 First Named Inventor: Herriot Tabuteau Assignee: Antecip Bioventures II LLC.
(Continued)

*Primary Examiner* — San Ming R Hui
(74) *Attorney, Agent, or Firm* — Maschoff Brennan; Brent A. Johnson; Yuefen Zhou

(57) ABSTRACT

Oral dosage forms of osteoclast inhibitors, such as neridronic acid, in an acid or a salt form, can be used to treat or alleviate pain or related conditions, such as complex regional pain syndrome.

28 Claims, 4 Drawing Sheets

Related U.S. Application Data

15/587,246, filed on May 4, 2017, now Pat. No. 9,782,421, which is a continuation-in-part of application No. 15/384,125, filed on Dec. 19, 2016, now Pat. No. 9,655,908, and a continuation-in-part of application No. 15/357,932, filed on Nov. 21, 2016, now Pat. No. 9,707,245, which is a continuation-in-part of application No. PCT/US2015/032739, filed on May 27, 2015, which is a continuation of application No. PCT/US2014/050427, filed on Aug. 8, 2014, which is a continuation of application No. 14/279,241, filed on May 15, 2014, now abandoned, which is a continuation-in-part of application No. 14/530,556, filed on Oct. 31, 2014, now abandoned, which is a continuation-in-part of application No. 14/279,229, filed on May 15, 2014, now Pat. No. 9,034,889, which is a continuation of application No. 14/063,979, filed on Oct. 25, 2013, now Pat. No. 8,802,658, which is a continuation-in-part of application No. 13/894,274, filed on May 14, 2013, now abandoned, which is a continuation-in-part of application No. 14/457,659, filed on Aug. 12, 2014, now abandoned, and a continuation-in-part of application No. 15/371,052, filed on Dec. 6, 2016, now abandoned, and a continuation-in-part of application No. 15/136,092, filed on Apr. 22, 2016, now Pat. No. 9,616,078, which is a continuation-in-part of application No. 16/222,040, filed on Dec. 17, 2018, which is a continuation of application No. 16/152,256, filed on Oct. 4, 2018, which is a continuation of application No. 15/963,878, filed on Apr. 26, 2018, now Pat. No. 10,117,880, which is a continuation of application No. 15/820,305, filed on Nov. 21, 2017, now Pat. No. 10,052,338, which is a continuation of application No. 15/703,891, filed on Sep. 13, 2017, now Pat. No. 9,931,352, which is a continuation-in-part of application No. 15/647,140, filed on Jul. 11, 2017, now Pat. No. 9,820,999, which is a continuation-in-part of application No. 15/357,932, filed on Nov. 21, 2016, now Pat. No. 9,707,245.

(60) Provisional application No. 62/431,287, filed on Dec. 7, 2016, provisional application No. 61/646,538, filed on May 14, 2012, provisional application No. 61/647,478, filed on May 15, 2012, provisional application No. 61/654,292, filed on Jun. 1, 2012, provisional application No. 61/654,383, filed on Jun. 1, 2012, provisional application No. 61/655,527, filed on Jun. 5, 2012, provisional application No. 61/655,541, filed on Jun. 5, 2012, provisional application No. 61/764,563, filed on Feb. 14, 2013, provisional application No. 61/762,225, filed on Feb. 7, 2013, provisional application No. 61/767,647, filed on Feb. 21, 2013, provisional application No. 61/767,676, filed on Feb. 21, 2013, provisional application No. 61/803,721, filed on Mar. 20, 2013, provisional application No. 62/150,871, filed on Apr. 22, 2015, provisional application No. 62/802,107, filed on Feb. 6, 2019.

(51) Int. Cl.
*A61K 9/28* (2006.01)
*A61K 9/00* (2006.01)

(56) References Cited

U.S. PATENT DOCUMENTS

| | | | |
|---|---|---|---|
| 5,869,471 | A | 2/1999 | Hovancik et al. |
| 6,015,801 | A | 1/2000 | Daifotis |
| 6,419,955 | B1 | 7/2002 | Gabel et al. |
| 6,468,559 | B1 | 10/2002 | Chen et al. |
| 6,943,155 | B2 | 9/2005 | Lichtenberger |
| 7,645,459 | B2 | 1/2010 | Dansereau |
| 7,658,939 | B2 | 2/2010 | Oshlack et al. |
| 7,704,977 | B2 | 4/2010 | Leonard |
| 8,053,429 | B2 | 11/2011 | Cumming et al. |
| 8,119,159 | B2 | 2/2012 | Cumming et al. |
| 8,323,689 | B2 | 12/2012 | Cumming et al. |
| 8,323,690 | B2 | 12/2012 | Cumming et al. |
| 8,399,023 | B2 | 3/2013 | Hanna et al. |
| 8,772,267 | B2 | 7/2014 | Pappagallo |
| 8,802,658 | B2 | 8/2014 | Tabuteau |
| 8,822,436 | B1 | 9/2014 | Tabuteau |
| 8,828,431 | B2 | 9/2014 | Cumming et al. |
| 8,835,650 | B1 | 9/2014 | Tabuteau |
| 8,859,530 | B2 | 10/2014 | Desai |
| 8,865,757 | B1 | 10/2014 | Tabuteau |
| 8,883,201 | B2 | 11/2014 | Leonard |
| 8,883,203 | B2 | 11/2014 | Leonard |
| 8,901,161 | B1 | 12/2014 | Tabuteau |
| 8,901,162 | B1 | 12/2014 | Tabuteau |
| 8,933,057 | B2 | 1/2015 | Hanna et al. |
| 8,962,599 | B1 | 2/2015 | Tabuteau |
| 9,006,279 | B1 | 4/2015 | Tabuteau |
| 9,034,889 | B2 | 5/2015 | Tabuteau |
| 9,079,927 | B1 | 7/2015 | Tabuteau |
| 9,149,487 | B2 | 10/2015 | Tabuteau |
| 9,169,279 | B2 | 10/2015 | Hanna et al. |
| 9,205,045 | B1 | 12/2015 | Tabuteau |
| 9,211,257 | B2 | 12/2015 | Tabuteau |
| 9,216,153 | B2 | 12/2015 | Tabuteau |
| 9,216,168 | B1 | 12/2015 | Tabuteau |
| 9,265,778 | B2 | 2/2016 | Tabuteau |
| 9,278,106 | B2 | 3/2016 | Tabuteau |
| 9,283,239 | B2 | 3/2016 | Tabuteau |
| 9,289,384 | B2 | 3/2016 | Tabuteau |
| 9,289,385 | B2 | 3/2016 | Tabuteau |
| 9,289,441 | B2 | 3/2016 | Tabuteau |
| 9,290,575 | B2 | 3/2016 | Tabuteau |
| 9,301,964 | B2 | 4/2016 | Tabuteau |
| 9,408,860 | B2 | 8/2016 | Tabuteau |
| 9,408,861 | B2 | 8/2016 | Tabuteau |
| 9,408,862 | B2 | 8/2016 | Tabuteau |
| 9,427,403 | B2 | 8/2016 | Tabuteau |
| 9,511,081 | B2 | 12/2016 | Tabuteau |
| 9,517,242 | B2 | 12/2016 | Tabuteau |
| 9,522,157 | B2 | 12/2016 | Tabuteau |
| 9,539,268 | B2 | 1/2017 | Tabuteau |
| 9,585,901 | B2 | 3/2017 | Tabuteau |
| 9,585,902 | B2 | 3/2017 | Tabuteau |
| 9,610,300 | B2 | 4/2017 | Tabuteau |
| 9,616,077 | B2 | 4/2017 | Tabuteau |
| 9,616,078 | B2 | 4/2017 | Tabuteau |
| 9,623,036 | B2 | 4/2017 | Tabuteau |
| 9,623,037 | B2 | 4/2017 | Tabuteau |
| 9,623,038 | B2 | 4/2017 | Tabuteau |
| 9,655,908 | B2 | 5/2017 | Tabuteau |
| 9,662,343 | B2 | 5/2017 | Tabuteau |
| 9,669,040 | B2 | 6/2017 | Tabuteau |
| 9,675,626 | B2 | 6/2017 | Tabuteau |
| 9,694,022 | B2 | 7/2017 | Tabuteau |
| 9,694,023 | B2 | 7/2017 | Tabuteau |
| 9,700,570 | B2 | 7/2017 | Tabuteau |
| 9,707,245 | B2 | 7/2017 | Tabuteau |
| 9,707,247 | B2 | 7/2017 | Tabuteau |
| 9,717,747 | B2 | 8/2017 | Tabuteau et al. |
| 9,770,457 | B2 | 9/2017 | Tabuteau |
| 9,782,421 | B1 | 10/2017 | Tabuteau |
| 9,789,128 | B2 | 10/2017 | Tabuteau |
| 9,795,622 | B2 | 10/2017 | Tabuteau |
| 9,820,999 | B2 | 11/2017 | Tabuteau |
| 9,827,192 | B2 | 11/2017 | Tabuteau |

(56) References Cited

U.S. PATENT DOCUMENTS

| | | |
|---|---|---|
| 9,827,256 B2 | 11/2017 | Tabuteau |
| 9,844,559 B2 | 12/2017 | Tabuteau |
| 9,855,213 B2 | 1/2018 | Tabuteau |
| 9,861,648 B2 | 1/2018 | Tabuteau |
| 9,867,839 B2 | 1/2018 | Tabuteau |
| 9,867,840 B2 | 1/2018 | Tabuteau |
| 9,877,977 B2 | 1/2018 | Tabuteau |
| 9,884,069 B2 | 2/2018 | Tabuteau |
| 9,895,383 B2 | 2/2018 | Tabuteau |
| 9,901,589 B2 | 2/2018 | Tabuteau |
| 9,925,203 B2 | 3/2018 | Tabuteau |
| 9,931,352 B2 | 4/2018 | Tabuteau |
| 9,943,531 B2 | 4/2018 | Tabuteau |
| 9,949,993 B2 | 4/2018 | Tabuteau |
| 9,956,234 B2 | 5/2018 | Tabuteau |
| 9,956,237 B2 | 5/2018 | Tabuteau |
| 9,956,238 B2 | 5/2018 | Tabuteau |
| 9,999,628 B2 | 6/2018 | Tabuteau |
| 9,999,629 B2 | 6/2018 | Tabuteau |
| 10,004,756 B2 | 6/2018 | Tabuteau |
| 10,016,445 B2 | 7/2018 | Tabuteau |
| 10,016,446 B2 | 7/2018 | Tabuteau |
| 10,028,908 B2 | 7/2018 | Tabuteau |
| 10,028,969 B2 | 7/2018 | Tabuteau |
| 10,034,890 B2 | 7/2018 | Tabuteau |
| 10,039,773 B2 | 8/2018 | Tabuteau |
| 10,039,774 B2 | 8/2018 | Tabuteau |
| 10,052,338 B2 | 8/2018 | Tabuteau |
| 10,092,581 B2 | 10/2018 | Tabuteau |
| 10,111,837 B2 | 10/2018 | Tabuteau |
| 10,111,891 B2 | 10/2018 | Tabuteau |
| 10,111,894 B2 | 10/2018 | Tabuteau |
| 10,117,880 B2 | 11/2018 | Tabuteau |
| 10,137,139 B2 | 11/2018 | Tabuteau |
| 10,173,986 B2 | 1/2019 | Tabuteau |
| 10,195,141 B2 | 2/2019 | Tabuteau |
| 10,195,223 B2 | 2/2019 | Tabuteau |
| 10,238,672 B2 | 3/2019 | Tabuteau |
| 10,265,332 B2 | 4/2019 | Tabuteau |
| 10,335,424 B2 | 7/2019 | Tabuteau |
| 2004/0063670 A1 | 4/2004 | Fox et al. |
| 2005/0026871 A1 | 2/2005 | Flashner-Barak et al. |
| 2005/0054616 A1 | 3/2005 | Aronhime |
| 2005/0260262 A1 | 11/2005 | Dansereau |
| 2006/0068010 A1 | 3/2006 | Turner |
| 2007/0134319 A1 | 6/2007 | Zannou et al. |
| 2009/0281064 A1 | 11/2009 | Ahmed et al. |
| 2010/0121040 A1 | 5/2010 | Nakazawa |
| 2010/0215743 A1 | 8/2010 | Leonard |
| 2011/0028435 A1 | 2/2011 | Hanna et al. |
| 2011/0098252 A1 | 4/2011 | Pappagallo |
| 2012/0190647 A1 | 7/2012 | Hanna et al. |
| 2013/0035315 A1 | 2/2013 | Hanna et al. |
| 2013/0274282 A1 | 10/2013 | Tabuteau |
| 2013/0303485 A1 | 11/2013 | Tabuteau |
| 2013/0303486 A1 | 11/2013 | Tabuteau |
| 2013/0303487 A1 | 11/2013 | Tabuteau |
| 2013/0303488 A1 | 11/2013 | Tabuteau |
| 2014/0051669 A1 | 2/2014 | Tabuteau |
| 2014/0051718 A1 | 2/2014 | Tabuteau |
| 2014/0107345 A1 | 4/2014 | Tabuteau |
| 2014/0249107 A1 | 9/2014 | Tabuteau |
| 2014/0249108 A1 | 9/2014 | Tabuteau |
| 2014/0249109 A1 | 9/2014 | Tabuteau |
| 2014/0249110 A1 | 9/2014 | Tabuteau |
| 2014/0249111 A1 | 9/2014 | Tabuteau |
| 2014/0249112 A1 | 9/2014 | Tabuteau |
| 2014/0249113 A1 | 9/2014 | Tabuteau |
| 2014/0249317 A1 | 9/2014 | Tabuteau |
| 2014/0256683 A1 | 9/2014 | Tabuteau |
| 2014/0329773 A1 | 11/2014 | Tabuteau |
| 2014/0348916 A1 | 11/2014 | Tabuteau |
| 2014/0349974 A1 | 11/2014 | Tabuteau |
| 2015/0051175 A1 | 2/2015 | Tabuteau |
| 2015/0057250 A1 | 2/2015 | Tabuteau |
| 2015/0133403 A1 | 5/2015 | Tabuteau |
| 2015/0141373 A1 | 5/2015 | Tabuteau |
| 2015/0141374 A1 | 5/2015 | Tabuteau |
| 2015/0148312 A1 | 5/2015 | Tabuteau |
| 2015/0157564 A1 | 6/2015 | Tabuteau |
| 2015/0164929 A1 | 6/2015 | Tabuteau |
| 2015/0216884 A1 | 8/2015 | Tabuteau |
| 2015/0344505 A1 | 12/2015 | Tabuteau |
| 2015/0361179 A1 | 12/2015 | Tabuteau |
| 2016/0038517 A1 | 2/2016 | Tabuteau |
| 2016/0095871 A1 | 4/2016 | Tabuteau |
| 2016/0095872 A1 | 4/2016 | Tabuteau |
| 2016/0113950 A1 | 4/2016 | Tabuteau |
| 2016/0151398 A1 | 6/2016 | Tabuteau |
| 2016/0158254 A1 | 6/2016 | Tabuteau |
| 2016/0158255 A1 | 6/2016 | Tabuteau |
| 2016/0158256 A1 | 6/2016 | Tabuteau |
| 2016/0166589 A1 | 6/2016 | Tabuteau |
| 2016/0166590 A1 | 6/2016 | Tabuteau |
| 2016/0175333 A1 | 6/2016 | Tabuteau |
| 2016/0199394 A1 | 7/2016 | Tabuteau |
| 2016/0199395 A1 | 7/2016 | Tabuteau |
| 2016/0206636 A1 | 7/2016 | Tabuteau |
| 2016/0235772 A1 | 8/2016 | Tabuteau |
| 2016/0263134 A1 | 9/2016 | Tabuteau |
| 2016/0296539 A1 | 10/2016 | Tabuteau |
| 2016/0324882 A1 | 11/2016 | Tabuteau |
| 2016/0331679 A1 | 11/2016 | Tabuteau |
| 2016/0331766 A1 | 11/2016 | Tabuteau |
| 2016/0331767 A1 | 11/2016 | Tabuteau |
| 2016/0331768 A1 | 11/2016 | Tabuteau |
| 2017/0042914 A1 | 2/2017 | Tabuteau |
| 2017/0049791 A1 | 2/2017 | Tabuteau |
| 2017/0056425 A1 | 3/2017 | Tabuteau |
| 2017/0056426 A1 | 3/2017 | Tabuteau |
| 2017/0056427 A1 | 3/2017 | Tabuteau |
| 2017/0065620 A1 | 3/2017 | Tabuteau |
| 2017/0065621 A1 | 3/2017 | Tabuteau |
| 2017/0065622 A1 | 3/2017 | Tabuteau |
| 2017/0065623 A1 | 3/2017 | Tabuteau |
| 2017/0065624 A1 | 3/2017 | Tabuteau |
| 2017/0065625 A1 | 3/2017 | Tabuteau |
| 2017/0071958 A1 | 3/2017 | Tabuteau |
| 2017/0071960 A1 | 3/2017 | Tabuteau |
| 2017/0079995 A1 | 3/2017 | Tabuteau |
| 2017/0079996 A1 | 3/2017 | Tabuteau |
| 2017/0079997 A1 | 3/2017 | Tabuteau |
| 2017/0079998 A1 | 3/2017 | Tabuteau |
| 2017/0087168 A1 | 3/2017 | Tabuteau |
| 2017/0087169 A1 | 3/2017 | Tabuteau |
| 2017/0095486 A1 | 4/2017 | Tabuteau |
| 2017/0095487 A1 | 4/2017 | Tabuteau |
| 2017/0095488 A1 | 4/2017 | Tabuteau |
| 2017/0100416 A1 | 4/2017 | Tabuteau |
| 2017/0100417 A1 | 4/2017 | Tabuteau |
| 2017/0119801 A1 | 5/2017 | Tabuteau |
| 2017/0128470 A1 | 5/2017 | Tabuteau |
| 2017/0128472 A1 | 5/2017 | Tabuteau |
| 2017/0136046 A1 | 5/2017 | Tabuteau |
| 2017/0143747 A1 | 5/2017 | Tabuteau |
| 2017/0157039 A1 | 6/2017 | Tabuteau |
| 2017/0157152 A1 | 6/2017 | Tabuteau |
| 2017/0157153 A1 | 6/2017 | Tabuteau |
| 2017/0172917 A1 | 6/2017 | Tabuteau |
| 2017/0173054 A1 | 6/2017 | Tabuteau |
| 2017/0182072 A1 | 6/2017 | Tabuteau |
| 2017/0209469 A1 | 7/2017 | Tabuteau |
| 2017/0216324 A1 | 8/2017 | Tabuteau |
| 2017/0224710 A1 | 8/2017 | Tabuteau |
| 2017/0232018 A1 | 8/2017 | Tabuteau |
| 2017/0252299 A1 | 9/2017 | Tabuteau |
| 2017/0252361 A1 | 9/2017 | Tabuteau |
| 2017/0260144 A1 | 9/2017 | Tabuteau |
| 2017/0266209 A1 | 9/2017 | Tabuteau |
| 2017/0281654 A1 | 10/2017 | Tabuteau |
| 2017/0281655 A1 | 10/2017 | Tabuteau |
| 2017/0281656 A1 | 10/2017 | Tabuteau |
| 2017/0304331 A1 | 10/2017 | Tabuteau |
| 2018/0000848 A1 | 1/2018 | Tabuteau |

(56) References Cited

U.S. PATENT DOCUMENTS

| | | |
|---|---|---|
| 2018/0015110 A1 | 1/2018 | Tabuteau |
| 2018/0015112 A1 | 1/2018 | Tabuteau |
| 2018/0021358 A1 | 1/2018 | Tabuteau |
| 2018/0028544 A1 | 2/2018 | Tabuteau |
| 2018/0042947 A1 | 2/2018 | Tabuteau |
| 2018/0050053 A1 | 2/2018 | Tabuteau |
| 2018/0055767 A1 | 3/2018 | Tabuteau |
| 2018/0055862 A1 | 3/2018 | Tabuteau |
| 2018/0064734 A1 | 3/2018 | Tabuteau |
| 2018/0064735 A1 | 3/2018 | Tabuteau |
| 2018/0064736 A1 | 3/2018 | Tabuteau |
| 2018/0071321 A1 | 3/2018 | Tabuteau |
| 2018/0071322 A1 | 3/2018 | Tabuteau |
| 2018/0110789 A1 | 4/2018 | Tabuteau |
| 2018/0133232 A1 | 5/2018 | Tabuteau |
| 2018/0140621 A1 | 5/2018 | Tabuteau |
| 2018/0153914 A1 | 6/2018 | Tabuteau |
| 2018/0161348 A1 | 6/2018 | Tabuteau |
| 2018/0169119 A1 | 6/2018 | Tabuteau |
| 2018/0207182 A1 | 7/2018 | Tabuteau |
| 2018/0228820 A1 | 8/2018 | Tabuteau |
| 2018/0228821 A1 | 8/2018 | Tabuteau |
| 2018/0235985 A1 | 8/2018 | Tabuteau |
| 2018/0243322 A1 | 8/2018 | Tabuteau |
| 2018/0256611 A1 | 9/2018 | Tabuteau |
| 2018/0264016 A1 | 9/2018 | Tabuteau |
| 2018/0271887 A1 | 9/2018 | Tabuteau |
| 2018/0280291 A1 | 10/2018 | Tabuteau |
| 2018/0280415 A1 | 10/2018 | Tabuteau |
| 2018/0280416 A1 | 10/2018 | Tabuteau |
| 2018/0360858 A1 | 12/2018 | Tabuteau |
| 2019/0000864 A1 | 1/2019 | Tabuteau |
| 2019/0015434 A1 | 1/2019 | Tabuteau |
| 2019/0023661 A1 | 1/2019 | Tabuteau |
| 2019/0030050 A1 | 1/2019 | Tabuteau |
| 2019/0030051 A1 | 1/2019 | Tabuteau |
| 2019/0030052 A1 | 1/2019 | Tabuteau |
| 2019/0054099 A1 | 2/2019 | Tabuteau |
| 2019/0091143 A1 | 3/2019 | Tabuteau |
| 2019/0099434 A1 | 4/2019 | Tabuteau |
| 2019/0111065 A1 | 4/2019 | Tabuteau |
| 2019/0117677 A1 | 4/2019 | Tabuteau |
| 2019/0160080 A1 | 5/2019 | Tabuteau |
| 2019/0167703 A1 | 6/2019 | Tabuteau |

FOREIGN PATENT DOCUMENTS

| | | |
|---|---|---|
| WO | 1999015155 | 4/1999 |
| WO | 2000028954 | 5/2000 |
| WO | 2002043738 | 1/2002 |
| WO | 2002087555 | 11/2002 |
| WO | 2003075741 | 9/2003 |
| WO | 2004035061 | 4/2004 |
| WO | 2005063218 | 7/2005 |
| WO | 2005072747 | 8/2005 |
| WO | 2005107751 | 11/2005 |
| WO | 2005115331 | 12/2005 |
| WO | 2005115406 | 12/2005 |
| WO | 2006102117 | 9/2006 |
| WO | 2011014781 | 2/2011 |
| WO | 2011097269 | 8/2011 |
| WO | 2012071517 | 5/2012 |
| WO | 2013173330 | 11/2013 |
| WO | 2015060924 | 4/2015 |
| WO | 2015184003 | 12/2015 |
| WO | 2007092338 | 8/2017 |

OTHER PUBLICATIONS

Mackey et al., Pharmacologic Therapies for Complex Regional Pain Syndrome, Current Pain and Headache Reports, 11 (1), 38-43, Mar. 2007.
U.S. Appl. No. 15/716,334, filed Sep. 26, 2017 First Named Inventor: Herriot Tabuteau Assignee: Antecip Bioventures II LLC.
Grünenthal GMBH, Petition for Post Grant Review of U.S. Pat. No. 9,539,268, dated Oct. 10, 2017.
U.S. Appl. No. 15/782,480, filed Oct. 12, 2017 First Named Inventor: Herriot Tabuteau Assignee: Antecip Bioventures II LLC.
U.S. Appl. No. 15/787,612, filed Oct. 18, 2017 First Named Inventor: Herriot Tabuteau Assignee: Antecip Bioventures II LLC.
Grünenthal GMBH, Declaration of Stephen Bruehl, for Petition for Post Grant Review of U.S. Pat. No. 9,539,268, dated Oct. 10, 2017.
Grünenthal GMBH, Declaration of Clive G. Wilson, for Petition for Post Grant Review of U.S. Pat. No. 9,539,268, dated Oct. 10, 2017.
Neogi et al., The Effect of Alendronate on Progression of Spinal Osteophytes and Disc-space Narrowing, Annals Rheumatic Diseases, 67, 1427-30, Feb. 2008.
Buckland-Wright et al., A 2 yr Longitudinal Radiographic Study Examining the Effect of a Bisphosphonate (Risedronate) upon Subchondral Bone Loss in Osteoarthritic Knee Patients, Rheumatology, 46, 257-64, Jul. 2007.
McQueen et al., Zoledronic Acid Does not Reduce MRI ErosiveProgression in PsA but may Suppress Bone Oedema: the Zoledronic Acid in Psoriatic Arthritis (ZAPA) Study, Annals Rheumatic Diseases, 70, 1091-94, Feb. 2011.
U.S. Appl. No. 15/801,028, filed Nov. 1, 2017 First Named Inventor: Herriot Tabuteau Assignee: Antecip Bioventures II LLC.
U.S. Appl. No. 15/801,049, filed Nov. 1, 2017 First Named Inventor: Herriot Tabuteau Assignee: Antecip Bioventures II LLC.
U.S. Appl. No. 15/804,781, filed Nov. 6, 2017 First Named Inventor: Herriot Tabuteau Assignee: Antecip Bioventures II LLC.
U.S. Appl. No. 15/806,236, filed Nov. 7, 2017 First Named Inventor: Herriot Tabuteau Assignee: Antecip Bioventures II LLC.
U.S. Appl. No. 15/808,794, filed Nov. 9, 2017 First Named Inventor: Herriot Tabuteau Assignee: Antecip Bioventures II LLC.
U.S. Appl. No. 15/814,745, filed Nov. 16, 2017 First Named Inventor: Herriot Tabuteau Assignee: Antecip Bioventures II LLC.
U.S. Appl. No. 15/820,305, filed Nov. 21, 2017 First Named Inventor: Herriot Tabuteau Assignee: Antecip Bioventures II LLC.
*Grunenthal GMBH v. Antecip Bioventures II LLC*, Case PGR2017-00022, U.S. Pat. No. 9,408,862, Decision, Institution of Post-Grant Review, pp. 1-46, dated Nov. 15, 2017.
Goldberg et al., Multi-Day Low Dose Ketamine Infusion for the Treatment of Complex Regional Pain Syndrome, Pain Physician, 8(2), 175-179, Apr. 2005.
U.S. Appl. No. 15/840,066, filed Dec. 13, 2017 First Named Inventor: Herriot Tabuteau Assignee: Antecip Bioventures II LLC.
U.S. Appl. No. 15/850,503, filed Dec. 21, 2017 First Named Inventor: Herriot Tabuteau Assignee: Antecip Bioventures II LLC.
Coderre et al., A Hypothesis for the Cause of Complex Regional Pain Syndrome-Type I (Reflex Sympathetic Dystrophy): Pain Due to Deep-Tissue Microvascular Pathology, Pain Medicine, 11(8), 1224-1238, Aug. 1, 2010.
Suresh, Migrating Bone Marrow Edema Syndrome: A Cause of Recurring Knee Pain, Acta Orthopaedica et Traumatologica Turcica, 44(4), 340-343, 2010.
Miettunen et al., Dramatic Pain Relief and Resolution of Bone Inflammation Following Pamidronate in 9 Pediatric Patients with Persistent Chronic Recurrent Multifocal Osteomyelitis (CRMO), Pediatric Rheumatology, 7(1), 2, Dec. 2009.
U.S. Appl. No. 15/877,067, filed Jan. 22, 2018 First Named Inventor: Herriot Tabuteau Assignee: Antecip Bioventures II LLC.
U.S. Appl. No. 15/879,107, filed Jan. 24, 2018 First Named Inventor: Herriot Tabuteau Assignee: Antecip Bioventures II LLC.
U.S. Appl. No. 15/887,271, filed Feb. 2, 2018 First Named Inventor: Herriot Tabuteau Assignee: Antecip Bioventures II LLC.
U.S. Appl. No. 15/897,947, filed Feb. 15, 2018 First Named Inventor: Herriot Tabuteau Assignee: Antecip Bioventures II LLC.
U.S. Appl. No. 15/934,785, filed Mar. 23, 2018 First Named Inventor: Herriot Tabuteau Assignee: Antecip Bioventures II LLC.
U.S. Appl. No. 15/952,017, filed Apr. 12, 2018 First Named Inventor: Herriot Tabuteau Assignee: Antecip Bioventures II LLC.
U.S. Appl. No. 15/954,017, filed Apr. 16, 2018 First Named Inventor: Herriot Tabuteau Assignee: Antecip Bioventures II LLC.
Grünenthal GMBH, Petition for Post-Grant Review of U.S. Pat. No. 9,707,245, dated Apr. 18, 2018.

(56) References Cited

OTHER PUBLICATIONS

U.S. Appl. No. 15/962,854, filed Apr. 25, 2018 First Named Inventor: Herriot Tabuteau Assignee: Antecip Bioventures II LLC.
U.S. Appl. No. 15/963,878, filed Apr. 26, 2018 First Named Inventor: Herriot Tabuteau Assignee: Antecip Bioventures II LLC.
Grunenthal GMBH v. Antecip Bioventures II LLC, Case PGR2018-00001, U.S. Pat. No. 9,539,268, Decision, Institution of Post-Grant Review, pp. 1-39, May 1, 2018.
U.S. Appl. No. 15/977,413, filed May 11, 2018 First Named Inventor: Herriot Tabuteau Assignee: Antecip Bioventures II LLC.
U.S. Appl. No. 15/982,794, filed May 17, 2018 First Named Inventor: Herriot Tabuteau Assignee: Antecip Bioventures II LLC.
U.S. Appl. No. 15/989,641, filed May 25, 2018 First Named Inventor: Herriot Tabuteau Assignee: Antecip Bioventures II LLC.
U.S. Appl. No. 15/997,470, filed Jun. 4, 2018 First Named Inventor: Herriot Tabuteau Assignee: Antecip Bioventures II LLC.
U.S. Appl. No. 15/997,530, filed Jun. 4, 2018 First Named Inventor: Herriot Tabuteau Assignee: Antecip Bioventures II LLC.
U.S. Appl. No. 16/002,888, filed Jun. 7, 2018 First Named Inventor: Herriot Tabuteau Assignee: Antecip Bioventures II LLC.
Grunenthal GMBH v. Antecip Bioventures II LLC, Case PGR2017-00008, U.S. Pat. No. 9,283,239, Final Written Decision, pp. 1-22, Jun. 22, 2018.
Grünenthal GMBH, Declaration of Lawrence Poree for Petition for Post Grant Review of U.S. Pat. No. 3,707,245, dated Apr. 18, 2018.
Bruehl, How Common is Complex Regional Pain Syndrom-Type I, Pain 129, 1-2, 2007.
Gatti et al., Neridronic Acid for the Treatment of Bone Metabolic Diseases, Expert Opinion on Drug Metabolism & Toxicology, 5(10), 1305-1311, Sep. 2009.
La Montagna et al., Successful Neridronate Therapy in Transient Osteoporosis of the Hip, Clin. Rheumatol., 24, 67-69, Aug. 2004.
Manicourt et al., Role of Alendronate in Therapy for Posttaumatic Complex Regional Pain Syndrome Type I of the Lower Extremity, Arthritis & Rheumatism, 50(11), 3690-3697, Nov. 2004.
Muratore et al., Il neridronato nel trattamento dell'algodistrofia simpatica riflessa dell'anca: confronto in aperto con il clodronato, Progressi in Rheumatologia, Abstract Book VII Congresso Nazionale Collegio Dei Reumatologi Ospedalieri, 5(Suppl. 1), 89, Apr. 16-18, 2004.
Adami et al., Intravenous Neridronate in Adults with Osteogenesis Imperfecta, J. Bone & Mineral Res., 18(1), 126-30, 2003.
Varenna, Efficacy Study of Neridronate to Treat Painful Osteoarthritis of the Knee With Bone Marrow Lesions, ClinicalTrials.gov, 3 pgs., last accessed on Mar. 13, 2013, available at: https://clinicaltrials.gov/ct2/show/NCT01803360.
Grünenthal GMBH, Efficacy and Safety of Intravenous Neridronic Acid in CRPS-I, ClinicalTrials.gov, 6 pgs., last accessed on Nov. 11, 2016, available at: https://clinicaltrials.gov/ct2/show/NCT02402530.
U.S. Appl. No. 15/385,415, filed Dec. 20, 2016 First Named Inventor: Herriot Tabuteau Assignee: Antecip Bioventures II LLC.
U.S. Appl. No. 15/386,858, filed Dec. 21, 2016 First Named Inventor: Herriot Tabuteau Assignee: Antecip Bioventures II LLC.
Grünenthal GMBH, Petition for Post Grant Review of U.S. Pat. No. 9,283,239, dated Dec. 14, 2016.
Grünenthal Gmbh, Declaration of Stephen Bruehl, for Petition for Post Grant Review of U.S. Pat. No. 9,283,239, dated Dec. 15, 2016.
U.S. Appl. No. 15/403,073, filed Jan. 10, 2017 First Named Inventor: Herriot Tabuteau Assignee: Antecip Bioventures II LLC.
U.S. Appl. No. 15/403,783, filed Jan. 18, 2017 First Named Inventor: Herriot Tabuteau Assignee: Antecip Bioventures II LLC.
U.S. Appl. No. 15/414,402, filed Jan. 24, 2017 First Named Inventor: Herriot Tabuteau Assignee: Antecip Bioventures II LLC.
U.S. Appl. No. 15/416,995, filed Jan. 26, 2017 First Named Inventor: Herriot Tabuteau Assignee: Antecip Bioventures II LLC.
U.S. Appl. No. 15/426,908, filed Feb. 7, 2017 First Named Inventor: Herriot Tabuteau Assignee: Antecip Bioventures II LLC.
Jarrett et al., Preliminary Evidence for a Structural Benefit of the New Bisphosphonate Zoledronic Acid in Early Rheumatoid Arthritis, Arthritis and Rheumatism, 54(5), 1410-1414, May 2006.
U.S. Appl. No. 15/432,777, filed Feb. 14, 2017 First Named Inventor: Herriot Tabuteau Assignee: Antecip Bioventures II LLC.
U.S. Appl. No. 15/438,513, filed Feb. 21, 2017 First Named Inventor: Herriot Tabuteau Assignee: Antecip Bioventures II LLC.
U.S. Appl. No. 15/439,774, filed Feb. 22, 2017 First Named Inventor: Herriot Tabuteau Assignee: Antecip Bioventures II LLC.
U.S. Appl. No. 15/446,971, filed Mar. 1, 2017 First Named Inventor: Herriot Tabuteau Assignee: Antecip Bioventures II LLC.
Varenna et al., Predictors of Responsiveness to Bisphosphonate Treatment in Patients with Complex Regional Pain Syndrome Type I: A Retrospective Chart Analysis, Pain Medicine, pnw207, Sep. 2016.
U.S. Appl. No. 15/454,874, filed Mar. 9, 2017 First Named Inventor: Herriot Tabuteau Assignee: Antecip Bioventures II LLC.
U.S. Appl. No. 15/459,992, filed Mar. 15, 2017 First Named Inventor: Herriot Tabuteau Assignee: Antecip Bioventures II LLC.
U.S. Appl. No. 15/481,330, filed Apr. 6, 2017 First Named Inventor: Herriot Tabuteau Assignee: Antecip Bioventures II LLC.
U.S. Appl. No. 15/484,766, filed Apr. 11, 2017 First Named Inventor: Herriot Tabuteau Assignee: Antecip Bioventures II LLC.
Moseley et al., Intense Pain Soon After Wrist Fracture Strongly Predicts Who Will Develop Complex Regional Pain Syndrome: Prospective Cohort Study. The Journal of Pain,15(1),16-23, Jan. 2014.
U.S. Appl. No. 15/498,251, filed Apr. 26, 2017 First Named Inventor: Herriot Tabuteau Assignee: Antecip Bioventures II LLC.
U.S. Appl. No. 15/587,108, filed May 4, 2017 First Named Inventor: Herriot Tabuteau Assignee: Antecip Bioventures II LLC.
U.S. Appl. No. 15/587,246, filed May 4, 2017 First Named Inventor: Herriot Tabuteau Assignee: Antecip Bioventures II LLC.
Grünenthal GMBH, Petition for Post Grant Review of U.S. Pat. No. 9,408,862, dated May 8, 2017.
Grünenthal GMBH, Declaration of Stephen Bruehl, for Petition for Post Grant Review of U.S. Pat. No. 3,408,862, dated May 8, 2017.
Grünenthal GMBH, Declaration of Clive G. Wilson, for Petition for Post Grant Review of U.S. Pat. No. 3,408,862, dated May 8, 2017.
Pazianas et al., Eliminating the Need for Fasting with Oral Administration of Bisphosphonates, Therapeutics & Clinical Risk Management, 9, 395-402, 2013.
Spector, Bisphosphonates: Potential Therapeutic Agents for Disease Modification in Osteoarthritis, Aging Clinical & Experimental Research, 15(5), 413-418, Oct. 2003.
Spector et al., Effect of Risedronate on Joint Structure and Symptoms of Knee Osteoarthritis: Results of the BRISK Randomized, Controlled Trial [ISRCTN01928173], Arthritis Reserch & Therapy, 7(3), R625, Mar. 2005.
Fujita et al., Comparison of the Analgesic Effects of Bisphosphonates: Etidronate, Alendronate and Risedronate by Electroalgometry Utilizing the Fall of Skin Impedance, Journal of Bone & Mineral Metabolism, 27(2), 234-239, Mar. 2009.
U.S. Appl. No. 15/599,319, filed May 18, 2017 First Named Inventor: Herriot Tabuteau Assignee: Antecip Bioventures II LLC.
U.S. Appl. No. 15/604,394, filed May 24, 2017 First Named Inventor: Herriot Tabuteau Assignee: Antecip Bioventures II LLC.
U.S. Appl. No. 15/605,730, filed May 25, 2017 First Named Inventor: Herriot Tabuteau Assignee: Antecip Bioventures II LLC.
U.S. Appl. No. 15/623,274, filed Jun. 14, 2017 First Named Inventor: Herriot Tabuteau Assignee: Antecip Bioventures II LLC.
U.S. Appl. No. 15/624,428, filed Jun. 15, 2017 First Named Inventor: Herriot Tabuteau Assignee: Antecip Bioventures II LLC.
U.S. Appl. No. 15/624,471, filed Jun. 15, 2017 First Named Inventor: Herriot Tabuteau Assignee: Antecip Bioventures II LLC.
U.S. Appl. No. 15/647,140, filed Jul. 11, 2017 First Named Inventor: Herriot Tabuteau Assignee: Antecip Bioventures II LLC.
Expert Declaration of Dr. Socrates Papapoulos, paragraphs 40-46, Apr. 2017.
Grunenthal GMBH v. Antecip Bioventures II LLC, Case PGR2017-00008, U.S. Pat. No. 9,238,239, Patent Owner's Preliminary Response, p. 35, dated Apr. 2017.
Grunenthal GMBH v. Antecip Bioventures II LLC, Case PGR2017-00008, U.S. Pat. No. 9,238,239, Decision, Institution of Post-Grant Review, pp. 29-30, dated Jul. 2017.

(56) References Cited

OTHER PUBLICATIONS

U.S. Appl. No. 15/672,126, filed Aug. 8, 2017 First Named Inventor: Herriot Tabuteau Assignee: Antecip Bioventures II LLC.
U.S. Appl. No. 15/672,147, filed Aug. 8, 2017 First Named Inventor: Herriot Tabuteau Assignee: Antecip Bioventures II LLC.
U.S. Appl. No. 15/697,211, filed Sep. 6, 2017 First Named Inventor: Herriot Tabuteau Assignee: Antecip Bioventures II LLC.
U.S. Appl. No. 15/697,267, filed Sep. 6, 2017 First Named Inventor: Herriot Tabuteau Assignee: Antecip Bioventures II LLC.
U.S. Appl. No. 15/702,616, filed Sep. 12, 2017 First Named Inventor: Herriot Tabuteau Assignee: Antecip Bioventures II LLC.
U.S. Appl. No. 15/703,891, filed Sep. 13, 2017 First Named Inventor: Herriot Tabuteau Assignee: Antecip Bioventures II LLC.
U.S. Appl. No. 15/707,238, filed Sep. 18, 2017 First Named Inventor: Herriot Tabuteau Assignee: Antecip Bioventures II LLC.
U.S. Appl. No. 15/707,673, filed Sep. 18, 2017 First Named Inventor: Herriot Tabuteau Assignee: Antecip Bioventures II LLC.
Sharma et al., Advances in Treatment of Complex Regional Pain Syndrome: Recent Insights on a Perplexing Disease, Current Opinion in Anesthesiology, 19(5), 566-572, Oct. 2006.
Siminoski et al., Intravenous Pamidronate for Treatment of Reflex Sympathetic Dystrophy During Breast Feeding, Journal of Bone and Mineral Research, 15(10), 2052-2055, Oct. 2000.
Simm et al., The Successful Use of Pamidronate in an 11-year-old Girl with Complex Regional Pain Syndrome: Response to Treatment Demonstrated by Serial Peripheral Quantitative Computerised Tomographic Scan, Bone, 46(4), 885-888, Apr. 2010.
Slobodin et al., The Synergistic Efficacy of Adalimumab and Pamidronate in a Patient with Ankylosing Spondylitis, Clinical Rheumatology, 29(7), 793-794, Jul. 2010.
Sorbera et al., Zoledronate Disodium, Drugs of the Future, 25(3), 259-268, Mar. 2000.
The Use of Zoledronic Acid to Complex Regional Pain Syndrome (Aclasta), ClinicalTrials.gov, 3 pgs., last accessed on Feb. 8, 2013, available at: http://clinicaltrials.gov/ct2/show/NCT01788176.
Tran et al., Treatment of Complex Regional Pain Syndrome: A Review of the Evidence, Canadian Journal of Anesthesia, 57(2), 149-166, Feb. 2010.
US Food and Drug Administration, Pharmacology Review of ZOMETA®, 261 pgs., Nov. 2001, available at: http://www.accessdata.fda.gov/drugsatfda_docs/nda/2001/21-223_Zometa.cfm.
US Food and Drug Administration, Severe Pain with Osteoporosis Drugs; FDA patient safety news: Show #73, 1 pg., Mar. 2008, available at: http://www.fda.gov/downloads/Safety/FDAPatientSafetyNews/UCM417867.pdf.
U.S. Appl. No. 13/894,244, filed May 14, 2013 First Named Inventor: Herriot Tabuteau Assignee: Antecip Bioventures II LLC.
U.S. Appl. No. 13/894,252, filed May 14, 2013 First Named Inventor: Herriot Tabuteau Assignee: Antecip Bioventures II LLC.
U.S. Appl. No. 13/894,262, filed May 14, 2013 First Named Inventor: Herriot Tabuteau Assignee: Antecip Bioventures II LLC.
U.S. Appl. No. 13/894,274, filed May 14, 2013 First Named Inventor: Herriot Tabuteau Assignee: Antecip Bioventures II LLC.
U.S. Appl. No. 14/063,979, filed Oct. 25, 2013 First Named Inventor: Herriot Tabuteau Assignee: Antecip Bioventures II LLC.
U.S. Appl. No. 14/106,291, filed Dec. 13, 2013 First Named Inventor: Herriot Tabuteau Assignee: Antecip Bioventures II LLC.
U.S. Appl. No. 14/279,196, filed May 15, 2014 First Named Inventor: Herriot Tabuteau Assignee: Antecip Bioventures II LLC.
U.S. Appl. No. 14/279,206, filed May 15, 2014 First Named Inventor: Herriot Tabuteau Assignee: Antecip Bioventures II LLC.
U.S. Appl. No. 14/279,213, filed May 15, 2014 First Named Inventor: Herriot Tabuteau Assignee: Antecip Bioventures II LLC.
U.S. Appl. No. 14/279,222, filed May 15, 2014 First Named Inventor: Herriot Tabuteau Assignee: Antecip Bioventures II LLC.
U.S. Appl. No. 14/279,226, filed May 15, 2014 First Named Inventor: Herriot Tabuteau Assignee: Antecip Bioventures II LLC.
U.S. Appl. No. 14/279,229, filed May 15, 2014 First Named Inventor: Herriot Tabuteau Assignee: Antecip Bioventures II LLC.
U.S. Appl. No. 14/279,232, filed May 15, 2014 First Named Inventor: Herriot Tabuteau Assignee: Antecip Bioventures II LLC.
U.S. Appl. No. 14/279,236, filed May 15, 2014 First Named Inventor: Herriot Tabuteau Assignee: Antecip Bioventures II LLC.
U.S. Appl. No. 14/279,241, filed May 15, 2014 First Named Inventor: Herriot Tabuteau Assignee: Antecip Bioventures II LLC.
U.S. Appl. No. 14/288,241, filed May 27, 2014 First Named Inventor: Herriot Tabuteau Assignee: Antecip Bioventures II LLC.
U.S. Appl. No. 14/288,713, filed May 28, 2014 First Named Inventor: Herriot Tabuteau Assignee: Antecip Bioventures II LLC.
U.S. Appl. No. 14/288,716, filed May 28, 2014 First Named Inventor: Herriot Tabuteau Assignee: Antecip Bioventures II LLC.
U.S. Appl. No. 14/288,720, filed May 28, 2014 First Named Inventor: Herriot Tabuteau Assignee: Antecip Bioventures II LLC.
U.S. Appl. No. 14/310,811, filed Jun. 20, 2014 First Named Inventor: Herriot Tabuteau Assignee: Antecip Bioventures II LLC.
U.S. Appl. No. 14/336,642, filed Jul. 21, 2014 First Named Inventor: Herriot Tabuteau Assignee: Antecip Bioventures II LLC.
U.S. Appl. No. 14/446,184, filed Jul. 29, 2014 First Named Inventor: Herriot Tabuteau Assignee: Antecip Bioventures II LLC.
U.S. Appl. No. 14/456,939, filed Aug. 11, 2014 First Named Inventor: Herriot Tabuteau Assignee: Antecip Bioventures II LLC.
U.S. Appl. No. 14/457,659, filed Aug. 12, 2014 First Named Inventor: Herriot Tabuteau Assignee: Antecip Bioventures II LLC.
U.S. Appl. No. 14/481,097, filed Sep. 9, 2014 First Named Inventor: Herriot Tabuteau Assignee: Antecip Bioventures II LLC.
U.S. Appl. No. 14/530,556, filed Oct. 31, 2014 First Named Inventor: Herriot Tabuteau Assignee: Antecip Bioventures II LLC.
U.S. Appl. No. 14/536,526, filed Nov. 7, 2014 First Named Inventor: Herriot Tabuteau Assignee: Antecip Bioventures II LLC.
U.S. Appl. No. 14/538,709, filed Nov. 11, 2014 First Named Inventor: Herriot Tabuteau Assignee: Antecip Bioventures II LLC.
U.S. Appl. No. 14/540,333, filed Nov. 13, 2014 First Named Inventor: Herriot Tabuteau Assignee: Antecip Bioventures II LLC.
U.S. Appl. No. 14/604,524, filed Jan. 23, 2015 First Named Inventor: Herriot Tabuteau Assignee: Antecip Bioventures II LLC.
U.S. Appl. No. 14/605,822, filed Jan. 26, 2015 First Named Inventor: Herriot Tabuteau Assignee: Antecip Bioventures II LLC.
U.S. Appl. No. 14/607,947, filed Jan. 28, 2015 First Named Inventor: Herriot Tabuteau Assignee: Antecip Bioventures II LLC.
U.S. Appl. No. 14/607,985, filed Jan. 28, 2015 First Named Inventor: Herriot Tabuteau Assignee: Antecip Bioventures II LLC.
U.S. Appl. No. 14/608,855, filed Jan. 29, 2015 First Named Inventor: Herriot Tabuteau Assignee: Antecip Bioventures II LLC.
U.S. Appl. No. 14/625,457, filed Feb. 18, 2015 First Named Inventor: Herriot Tabuteau Assignee: Antecip Bioventures II LLC.
U.S. Appl. No. 14/635,857, filed Mar. 2, 2015 First Named Inventor: Herriot Tabuteau Assignee: Antecip Bioventures II LLC.
U.S. Appl. No. 14/639,013, filed Mar. 13, 2015 First Named Inventor: Herriot Tabuteau Assignee: Antecip Bioventures II LLC.
U.S. Appl. No. 14/686,551, filed Apr. 14, 2015 First Named Inventor: Herriot Tabuteau Assignee: Antecip Bioventures II LLC.
U.S. Appl. No. 14/967,224, filed Dec. 11, 2015 First Named Inventor: Herriot Tabuteau Assignee: Antecip Bioventures II LLC.
U.S. Appl. No. 14/967,234, filed Dec. 11, 2015 First Named Inventor: Herriot Tabuteau Assignee: Antecip Bioventures II LLC.
U.S. Appl. No. 14/968,514, filed Dec. 14, 2015 First Named Inventor: Herriot Tabuteau Assignee: Antecip Bioventures II LLC.
Abe et al., Improvement of Pain and Regional Osteoporotic Changes in the Foot and Ankle by Low-Dose Bisphosphonate Therapy for Complex Regional Pain Syndrome Type I: A Case Series, Journal of Medical Case Reports, 5(1), 349-354, Aug. 2011.
Adami et al., Bisphosphonate Therapy of Reflex Sympathetic Dystrophy Syndrome, Annals of Rheumatic Diseases, 56(3), 201-204, Mar. 1997.
Bingham et al., Risedronate Decreases Biochemical Markers of Cartilage Degradation but Does Not Decrease Symptoms or Slow Radiographic Progression in Patients with Medical Compartment Osteoarthritis of the Knee, Arthritis & Rheumatism, 54(11), 3494-3507, Nov. 2006.
Bonabello et al., Analgesic Effect of Bisphosphonates in Mice, Pain, 91(3), 269-275, Apr. 2001.

(56) References Cited

OTHER PUBLICATIONS

Breuer et al., An Open-Label Pilot Trial of Ibandronate for Complex Regional Pain Syndrome, The Clinical Journal of Pain, 24(8), 685-689, Oct. 2008.
Brunner et al., Biphosphonates for the Therapy of Complex Regional Pain Syndrome I—Systematic Review, European Journal of Pain, 13(1), 17-21, Jan. 2009.
Cantatore et al., Evaluation of Bone Turnover and Osteoclastic Cytokines in Early Rheumatoid Arthritis Treated with Alendronate, The Journal of Rheumatology, 26(11), 2318-2323, Nov. 1999.
Chauvineau et al., What is the Place of Diphosphonates in the Treatment of Complex Regional Pain Syndrom I? A Literature Review, Annales de Readaptation et de Medecine Physique, 48(3), 150-157, Apr. 2005.
Clere, CRPS: Evidence Still Needed for Biphosphonates, Douleurs Evaluation—Diagnostic—Traitement 10(4), 214-215, Sep. 2009.
Conte et al., Safety of Intravenous and Oral Bisphosphonates and Compliance with Dosing Regimens, The Oncologist, 9 (Suppl 4), 28-37, Sep. 2004.
Cortet et al., Treatment of Severe, Recalcitrant Reflex Sympathetic Dystrophy: Assessment of Efficacy and Safety of the Second Generation Bisphosphonate Pamidronate, Clinical Rheumatology, 16(1), 51-56, Jan. 1997.
Cremers et al., Pharmacokinetics/Pharmacodynamics of Bisphosphonates, Clinical Pharmacokinetics, 44(6), 551-570, Jun. 2005.
Cullen et al., MER-101: A Bioavailability Study of Various GIPET™ Formulations in Beagle Dogs with Intraduodenal Cannulae, Abstract T3147, American Association of Pharmaceutical Scientists (AAPS), San Diego, CA, USA, Nov. 12-16, 2007.
De Castro et al., Zoledronic Acid to Treat Complex Regional Pain Syndrome Type I in Adult (Case Report), Revista Dor Pesquisa Clinica e Terapêutica, Sao Paulo, 12(1), 71-73, Jan.-Mar. 2011.
Devogelaer et al., Dramatic Improvement of Interactable Reflex Sympathetic Dystrophy Syndrome by Intravenous Infusions of the Second Generation Bisphosphonate APD., Abstract 213, 3(suppl), S122, Tenth Annual Meeting of the American Society for Bone and Mineral Research, New Orleans, LA, USA, Jun. 4-7, 1988.
Dubin, Weekly, Oral Zoledronic Acid can Improve Quality of Life for Bone Metastases Sufferers, Specialty Pharma, 10(3), 30-33, Nov. 2010.
European Medicines Agency, Public Summary of Opinion on Orphan Designation, Zoledronic Acid for the Treatment of Complex Regional Pain Syndrome, 4 pgs., Oct. 2013.
European Medicines Agency, Scientific Discussion of Aclasta®, 24 pgs., Mar. 2005, available at: http://www.ema.europa.eu/docs/en_GB/document_library/EPAR_-_Scientific_Discussion/human/000595/WC500020933.pdf.
European Union Summary of Product Characteristics for ACLASTA®, last accessed Aug. 2012, 19 pgs.
European Union Summary of Product Characteristics for ZOMETA®, last accessed Aug. 2012, 49 pgs.
Gangji et al., Analgesic Effect of Intravenous Pamidronate on Chronic Back Pain Due to Osteoporotic Vertebral Fractures, Clinical Rheumatology, 18(3), 266-267, May 1999.
Giles, Risedronate not an Effective Disease Modifier in Knee Osteoarthritis, John Hopkins Medicine, Oct. 2006, available at http://www.hopkinsarthritis.org/arthritis-news/risedronate-not-an-effective-disease-modifier-in-knee-osteoarthritis.
Gremeaux et al., Complex Regional Pain Syndrome of the Knee: Early and Good Action of Biphosphonates on Pain and Function, Annales de réadaptation et de médecine physique 50(4), 240-243, May 2007.
Hamida et al., Myositis Ossificans Circumscripta of the Knee Improved by Alendronate, Joint Bone Spine, 71(2), 144-146, Apr. 2004.
Henson et al., Complex Regional Pain Syndrome: State-of-the-Art Update, Current Treatment Options in Cardiovascular Medicine, 12(2), 156-167, Apr. 2010.

Kim et al., Analgesic Effects of the Non-Nitrogen-Containing Bisphosphonates Etidronate and Clodronate, Independent of Anti-Resorptive Effects on Bone, European Journal of Pharmacology, 699(1-3), 14-22, Jan. 2013.
Koivisto et al., Efficacy of Zoledronic Acid for Chronic Low Back Pain Associated with Modic Changes in Magnetic Resonance Imaging, BMC Musculoskeletal Disorders, 15(64), 1-9, Mar. 2014.
Kopterides et al., Successful Treatment of SAPHO Syndrome with Zoledronic Acid, Rheumatoid Arthritis, 50(9), 2970-2973, Sep. 2004.
Kretzchmar et al., Rapid and Sustained Influence of Intravenous Zoledronic Acid on Course of Pain and Analgesics Consumption in Patients with Cancer with Bone Metastases: A Multicenter Open-Label Study over 1 Year, Supportive Cancer Therapy, 4(4), 203-210, Sep. 2007.
Kubalek et al., Treatment of Reflex Sympathetic Dystrophy with Pamidronate: 29 Cases, Rheumatology, 40(12),1394-1397, Dec. 2001.
Laslett et al., Zoledronic Acid Reduces Knee Pain and Bone Marrow Lesions over 1 Year: A Randomized Controlled Trial, Annals of the Rheumatic Diseases, 71(8), 1322-1328, Aug. 2012.
Leonard et al., MER-101 Tablets: A Pilot Bioavailability Study of a Novel Oral Formulation of Zoledronic Acid, Poster Presentation, Molecular Targets and Cancer Therapeutics, San Francisco, CA, USA, Oct. 22-26, 2007.
Leonard et al., Safety Profile of Zoledronic Acid in a Novel Oral Formulation, Poster Presentation, Molecular Targets & Cancer Therapeutics Conference, Boston, MA, USA, Nov. 15-19, 2009.
Leonard et al., Studies of Bioavailability and Food Effects of MER-101 Zoledronic Acid Tablets in Postmenopausal Women, Poster Presentation, ASCO Breast Cancer Symposium, San Francisco, CA, USA, Oct. 2009.
Maillefert et al., Treatment of Refractory Reflex Sympathetic Dystrophy with Pamidronate, Annals of the Rhematic Diseases, 54(8), 687, Sep. 1995.
Maksymowych et al., A Six-Month Randomized, Controlled, Double-Blind, Dose-Response Comparison of Intravenous Pamidronate (60 mg versus 10 mg) in the Treatment of Nonsteroidal Antiinflammatory Drug-Refractory Ankylosing Spondylitis, Arthritis & Rheumatism, 46(3), 766-773, Mar. 2002.
Manicourt et al., Role of Alendronate in Therapy for Posttraumatic Complex Regional Pain Syndrome Type 1 of the Lower Extremity, Rheumatoid & Arthritis, 50(11), 3690-3697, Nov. 2004.
Matsuo et al., Antiinflammatory and Chondroprotective Effects of the Aminobisphosphonate Incadronate (YM175) in Adjuvant Induced Arthritis, abstract, The Journal of rheumatology, 30(6), 1280-1290, Jun. 2003.
Mc Hugh et al., MER-101-03, A Multi Center, Phase II Study to Compare MER-101 20 mg Tablets to Intravenous ZOMETA® 4 mg in Prostate Cancer Patients, Abstract and Presentation, American Society of Clinical Oncology Annual Meeting, Orlando, FL, USA, May 29-Jun. 2, 2009.
Merrion Pharmaceuticals, ORAZOL®: Novel Approach to Adjuvant Therapy for Improving Outcomes in Breast Cancer, Presentation, 15 pgs., Apr. 2011, last accessed at http://www.merrionpharma.com/archive/presentations/ORAZOLPresentationQ12011.pdf.
Novartis Pharmaceutical Corporation, Highlights of Prescribing Information for RECLAST® (Zoledronic Acid), Injection, 28 pgs., last revised Apr. 2013, available at http://www.accessdata.fda.gov/drugsatfda_docs/label/2013/021817s015lbl.pdf.
Orcel et al., Bisphosphonates in Bone Diseases Other than Osteoporosis, Joint Bone Spine, 69(1), 19-27, Jan. 2002.
Orcel, Response, Joint Bone Spine, 69(5), 522, Oct. 2002.
Podworny et al., Partial Chondroprotective Effect of Zoledronate in a Rabbit Model of Inflammatory Arthritis, abstract, The Journal of Rheumatology, 26(9), 1972-1982, Sep. 1999.
Rehman et al., Treatment of Reflex Sympathetic Dystrophy with Intravenous Pamidronate, Abstract P36, Bone and Tooth Society Meeting, p. 116, Apr. 1991.
Ringe, Development of Clinical Utility of Zoledronic Acid and Patient Consideration in the Treatment of Osteoporosis, Patient Preference and Adherence, 4, 231-245, Jul. 2010.

(56) References Cited

OTHER PUBLICATIONS

Robinson et al., Efficacy of Pamidronate in Complex Regional Pain Syndrome Type I, Pain Medicine, 5(3), 276-280, Sep. 2004.
Rovetta et al., Efficacy of Disodium-Clodronate in the Management of Joint Pain in Rheumatoid Arthritis. Six Months Open Study, abstract, Minerva Medica, 94(5), 353-7, Oct. 2003.
Schott, Bisphosphonates for Pain Relief in Reflex Sympathetic Dystrophy?, The Lancet, 350(9085), 1117, Oct. 1997.
Sebastin, Complex Regional Pain Syndrome, Indian Journal of Plastic Surgery, 44(2), 298-307, May 2011.
Varenna et al., Predictors of Responsiveness to Bisphosphonate Treatment in Patients with Complex Regional Pain Syndrome Type I: A Retrospective Chart Analysis, Pain Med., 18, 1131-38, 2017.
Merskey et al., Pain Terms: A Current List with Definitions and Notes on Usage, in Classification of Chronic Pain, 207-213, Merskey & Bogduk eds., 1994.
Fosamax® (alendronate sodium) Tablets for Oral Use and Oral Solution Prescribing Information, Feb. 2012.
Boniva® (ibandronate sodium) Tablets Prescribing Information, Jan. 2011.
Schwarzer & Maier, Complex Regional Pain Syndrome, in Guide to Pain Management in Low-Resource Settings, 249-254, Kopf & Patel eds., 2010.
Grünenthal GMBH, Petition for Post-Grant Review of U.S. Pat. No. 9,820,999, dated Aug. 21, 2018.
U.S. Appl. No. 16/110,869, filed Aug. 23, 2018 First Named Inventor: Herriot Tabuteau Assignee: Antecip Bioventures II LLC.
Grünenthal GMBH, Declaration of Lawrence Poree for Petition for Post Grant Review of U.S. Pat. No. 9,820,999, dated Aug. 21, 2018.
U.S. Appl. No. 16/124,069, filed Sep. 6, 2018 First Named Inventor: Herriot Tabuteau Assignee: Antecip Bioventures II LLC.
U.S. Appl. No. 16/136,065, filed Sep. 18, 2018 First Named Inventor: Herriot Tabuteau Assignee: Antecip Bioventures II LLC.
U.S. Appl. No. 16/137,446, filed Sep. 20, 2018 First Named Inventor: Herriot Tabuteau Assignee: Antecip Bioventures II LLC.
U.S. Appl. No. 16/144,916, filed Sep. 27, 2018 First Named Inventor: Herriot Tabuteau Assignee: Antecip Bioventures II LLC.
U.S. Appl. No. 16/152,256, filed Oct. 4, 2018 First Named Inventor: Herriot Tabuteau Assignee: Antecip Bioventures II LLC.
U.S. Appl. No. 16/152,750, filed Oct. 5, 2018 First Named Inventor: Herriot Tabuteau Assignee: Antecip Bioventures II LLC.
U.S. Appl. No. 16/167,371, filed Oct. 22, 2018 First Named Inventor: Herriot Tabuteau Assignee: Antecip Bioventures II LLC.
U.S. Appl. No. 16/168,632, filed Oct. 23, 2018 First Named Inventor: Herriot Tabuteau Assignee: Antecip Bioventures II LLC.
Manara et al., SAT0524 Predictors of a clinical response to bisphosphonates treatment in patients with complex regional pain syndrome Type I, Annals of The Rheumatic Diseases 73(Suppl. 2), 2014.
Grünenthal GMBH, Petition for Post-Grant Review of U.S. Pat. No. 9,867,839, dated Oct. 16, 2018.
Grünenthal GMBH, Declaration of Lawrence Poree for Petition for Post Grant Review of U.S. Pat. No. 9,867,839, dated Oct. 16, 2018.
Hutton MJ, et al., Modic Vertebral Body Changes: The Natural History as Assessed by Consecutive Magnetic Resonance Imaging. Spine, 36(26), 2304-2307, Dec. 15, 2011.
Dowd et al. Complex regional pain syndrome with special emphasis on the knee. The Journal of bone and joint surgery. British volume. 89(3):285-90, Mar. 2007.
Rossini et al. Intra-articular clodronate for the treatment of knee osteoarthritis: dose ranging study vs hyaluronic acid. Rheumatology. 48(7):773-8, Apr. 2009.
Merskey, H & Bogduk, N.,, Classification of chronic pain: Descriptions of chronic pain syndromes and definitions of pain terms (second edition), 1994.
Bruehl, An update on the pathophysiology of complex regional pain syndrome. Anesthesiology 113(3):713-25, Sep. 2010.
Harden et al. Validation of proposed diagnostic criteria (the "Budapest Criteria") for complex regional pain syndrome. Pain 150(2):268-74, Aug. 2010.

Carbone et al. The relationship of antiresorptive drug use to structural findings and symptoms of knee osteoarthritis. Arthritis & Rheumatism 50(11):3516-25, Nov. 2004.
Morabito et al. Neridronate prevents bone loss in patients receiving androgen deprivation therapy for prostate cancer. Journal of Bone and Mineral Research 19(11):1766-70, Nov. 2004.
Merlotti et al. Comparison of different intravenous bisphosphonate regimens for Paget's disease of bone. Journal of Bone and Mineral Research 22(10):1510-7, Oct. 2007.
Benucci et al. Effects of monthly intramuscular neridronate in rheumatic patients in chronic treatment with low-dose glucocorticoids. Clin Exp Rheumatol. 27(4):567-73, Jul. 2009.
Gatti et al. New bisphosphonates in the treatment of bone diseases. Drugs & aging. 15(4):285-96, Oct. 1999.
Zometa® (zoledronic acid) Injection Concentrate for Intravenous Infusion Prescribing Information, Oct. 2009.
U.S. Appl. No. 16/208,413, filed Dec. 3, 2018 First Named Inventor: Herriot Tabuteau Assignee: Antecip Bioventures II LLC.
U.S. Appl. No. 16/218,383, filed Dec. 12, 2018 First Named Inventor: Herriot Tabuteau Assignee: Antecip Bioventures II LLC.
U.S. Appl. No. 16/222,040, filed Dec. 17, 2018 First Named Inventor: Herriot Tabuteau Assignee: Antecip Bioventures II LLC.
Grünenthal GMBH, Petition for Post-Grant Review of U.S. Pat. No. 9,931,352, dated Jan. 3, 2019.
Grünenthal GMBH, Petition for Post-Grant Review of U.S. Pat. No. 10,039,774, dated Jan. 3, 2019.
Grünenthal GMBH, Petition for Post-Grant Review of U.S. Pat. No. 10,052,338, dated Jan. 3, 2019.
Grünenthal GMBH, Declaration of Lawrence Poree for Petition for Post Grant Review of U.S. Pat. Nos. 9,931,352, 10,039,774, & 10,052,338, dated Jan. 3, 2019.
Varenna, L'inquadramento clinico della sindrome algodistrofica (Complex Regional Pain Syndrome Di Tipo I). Recenti acquisizioni, The clinical framework of algodystrophy (Complex Regional Pain Syndrome type I). An update, Giornale Italiano di Ortopedia e Traumatologia. 37:227-3, Oct. 2011.
Drummond, Sensory Disturbances in Complex Regional Pain Syndrome: Clinical Observations, Autonomic Interactions, and Possible Mechanisms, Pain Medicine. 11(8):1257-66, Jul. 2010.
Bruehl, et al., External validation of IASP diagnostic criteria for Complex Regional Pain Syndrome and proposed research diagnostic criteria, Pain. 81(1-2):147-54, May 1999.
U.S. Appl. No. 16/264,237, filed Jan. 31, 2019 First Named Inventor: Herriot Tabuteau Assignee: Antecip Bioventures II LLC.
U.S. Appl. No. 16/267,295, filed Feb. 4, 2019 First Named Inventor: Herriot Tabuteau Assignee: Antecip Bioventures II LLC.
U.S. Appl. No. 16/365,459, filed Mar. 26, 2019 First Named Inventor: Herriot Tabuteau Assignee: Antecip Bioventures II LLC.
U.S. Appl. No. 16/366,207, filed Mar. 27, 2019 First Named Inventor: Herriot Tabuteau Assignee: Antecip Bioventures II LLC.
U.S. Appl. No. 16/366,818, filed Mar. 27, 2019 First Named Inventor: Herriot Tabuteau Assignee: Antecip Bioventures II LLC.
U.S. Appl. No. 15/009,712, filed Jan. 28, 2016 First Named Inventor: Herriot Tabuteau Assignee: Antecip Bioventures II LLC.
U.S. Appl. No. 15/014,994, filed Feb. 3, 2016 First Named Inventor: Herriot Tabuteau Assignee: Antecip Bioventures II LLC.
U.S. Appl. No. 15/042,017, filed Feb. 11, 2016 First Named Inventor: Herriot Tabuteau Assignee: Antecip Bioventures II LLC.
U.S. Appl. No. 15/043,141, filed Feb. 12, 2016 First Named Inventor: Herriot Tabuteau Assignee: Antecip Bioventures II LLC.
U.S. Appl. No. 15/043,281, filed Feb. 12, 2016 First Named Inventor: Herriot Tabuteau Assignee: Antecip Bioventures II LLC.
U.S. Appl. No. 15/043,419, filed Feb. 12, 2016 First Named Inventor: Herriot Tabuteau Assignee: Antecip Bioventures II LLC.
U.S. Appl. No. 15/055,386, filed Feb. 26, 2016 First Named Inventor: Herriot Tabuteau Assignee: Antecip Bioventures II LLC.
U.S. Appl. No. 15/074,367, filed Mar. 18, 2016 First Named Inventor: Herriot Tabuteau Assignee: Antecip Bioventures II LLC.
U.S. Appl. No. 15/074,380, filed Mar. 18, 2016 First Named Inventor: Herriot Tabuteau Assignee: Antecip Bioventures II LLC.
U.S. Appl. No. 15/083,105, filed Mar. 28, 2016 First Named Inventor: Herriot Tabuteau Assignee: Antecip Bioventures II LLC.

(56) References Cited

OTHER PUBLICATIONS

U.S. Appl. No. 15/136,092, filed Apr. 22, 2016 First Named Inventor: Herriot Tabuteau Assignee: Antecip Bioventures II LLC.
U.S. Appl. No. 15/164,651, filed May 25, 2016 First Named Inventor: Herriot Tabuteau Assignee: Antecip Bioventures II LLC.
U.S. Appl. No. 15/188,725, filed Jun. 21, 2016 First Named Inventor: Herriot Tabuteau Assignee: Antecip Bioventures II LLC.
U.S. Appl. No. 15/211,827, filed Jul. 15, 2016 First Named Inventor: Herriot Tabuteau Assignee: Antecip Bioventures II LLC.
U.S. Appl. No. 15/217,752, filed Jul. 22, 2016 First Named Inventor: Herriot Tabuteau Assignee: Antecip Bioventures II LLC.
U.S. Appl. No. 15/217,773, filed Jul. 22, 2016 First Named Inventor: Herriot Tabuteau Assignee: Antecip Bioventures II LLC.
U.S. Appl. No. 15/223,487, filed Jul. 29, 2016 First Named Inventor: Herriot Tabuteau Assignee: Antecip Bioventures II LLC.
U.S. Appl. No. 15/223,548, filed Jul. 29, 2016 First Named Inventor: Herriot Tabuteau Assignee: Antecip Bioventures II LLC.
US Food and Drug Administration, CRPS Orphan Drug Designation for Zoledronic Acid, 1 pg., May 6, 2013, available at http://www.accessdata.fda.gov/scripts/opdlisting/oopd/OOPD_Results_2.cfm?Index_Number=374112.
Van Offel et al., Influence of Cyclic Intravenous Pamidronate on Proinflammatory Monocytic Cytokine Profiles and Bone Density in Rheumatoid Arthritis Treated with Low Dose Prednisolone and Methrotrexate, Clinical and Experimental Rheumatology, 19(1), 13-20, Jan. 2001.
Varenna et al., Intravenous Clodronate in the Treatment of Reflex Sympathetic Dystrophy Syndrome. A Randomized, Double Blind, Placebo Controlled Study, The Journal of Rheumatology, 27(6), 1477-1483, Jun. 2000.
Varenna et al., Treatment of Complex Regional Pain Syndrome Type I with Neridronate: A Randomized, Double-Blind, Placebo-Controlled Study, Rheumatology, 534-542, Nov. 2012.
Walker et al., Disease Modifying and Anti-Nociceptive Effects of the Bisphosphonate, Zoledronic Acid in a Model of Bone Cancer Pain, Pain, 100(3), 219-229, Dec. 2002.
Yanow et al., Complex Regional Pain Syndrome (CRPS/RSD) and Neuropathic Pain: Role of Intravenous Bisphosphonates as Analgesics, The Scientific World Journal, 8, 229-236, Feb. 2008.
Zaspel et al., Treatment of Early Stage CRPS I—Cortisone (Methylprednisolone) Versus Bisphosphonate (Zoledronic Acid), German Congress of Orthopedics and Traumatology, Berlin, DE, Oct. 24-27, 2007.
Altman et al., Low Back Pain in Paget's Disease of Bone, Clinical Orthopedic and Related Research, 217, 152-161, Apr. 1987.
McHugh et al., MER-101 Tablets: A Pilot Bioavailability Study of a Novel Oral Formulation of Zoledronic Acid, Molecular Cancer Therapeutics, Nov. 2007; B194.
U.S. Appl. No. 15/246,325, filed Aug. 24, 2016 First Named Inventor: Herriot Tabuteau Assignee: Antecip Bioventures II LLC.
U.S. Appl. No. 15/335,381, filed Oct. 26, 2016 First Named Inventor: Herriot Tabuteau Assignee: Antecip Bioventures II LLC.
U.S. Appl. No. 15/347,696, filed Nov. 9, 2016 First Named Inventor: Herriot Tabuteau Assignee: Antecip Bioventures II LLC.
U.S. Appl. No. 15/348,808, filed Nov. 10, 2016 First Named Inventor: Herriot Tabuteau Assignee: Antecip Bioventures II LLC.
U.S. Appl. No. 15/348,842, filed Nov. 10, 2016 First Named Inventor: Herriot Tabuteau Assignee: Antecip Bioventures II LLC.
U.S. Appl. No. 15/349,926, filed Nov. 11, 2016 First Named Inventor: Herriot Tabuteau Assignee: Antecip Bioventures II LLC.
U.S. Appl. No. 15/352,461, filed Nov. 15, 2016 First Named Inventor: Herriot Tabuteau Assignee: Antecip Bioventures II LLC.
U.S. Appl. No. 15/353,550, filed Nov. 16, 2016 First Named Inventor: Herriot Tabuteau Assignee: Antecip Bioventures II LLC.
U.S. Appl. No. 15/354,862, filed Nov. 17, 2016 First Named Inventor: Herriot Tabuteau Assignee: Antecip Bioventures II LLC.
U.S. Appl. No. 15/354,908, filed Nov. 17, 2016 First Named Inventor: Herriot Tabuteau Assignee: Antecip Bioventures II LLC.
U.S. Appl. No. 15/356,434, filed Nov. 18, 2016 First Named Inventor: Herriot Tabuteau Assignee: Antecip Bioventures II LLC.
U.S. Appl. No. 15/357,769, filed Nov. 21, 2016 First Named Inventor: Herriot Tabuteau Assignee: Antecip Bioventures II LLC.
U.S. Appl. No. 15/357,932, filed Nov. 21, 2016 First Named Inventor: Herriot Tabuteau Assignee: Antecip Bioventures II LLC.
U.S. Appl. No. 15/360,886, filed Nov. 23, 2016 First Named Inventor: Herriot Tabuteau Assignee: Antecip Bioventures II LLC.
U.S. Appl. No. 15/364,117, filed Nov. 29, 2016 First Named Inventor: Herriot Tabuteau Assignee: Antecip Bioventures II LLC.
U.S. Appl. No. 15/365,748, filed Nov. 30, 2016 First Named Inventor: Herriot Tabuteau Assignee: Antecip Bioventures II LLC.
U.S. Appl. No. 15/367,048, filed Dec. 1, 2016 First Named Inventor: Herriot Tabuteau Assignee: Antecip Bioventures II LLC.
U.S. Appl. No. 15/368,355, filed Dec. 2, 2016 First Named Inventor: Herriot Tabuteau Assignee: Antecip Bioventures II LLC.
U.S. Appl. No. 15/371,052, filed Dec. 6, 2016 First Named Inventor: Herriot Tabuteau Assignee: Antecip Bioventures II LLC.
U.S. Appl. No. 15/377,907, filed Dec. 13, 2016 First Named Inventor: Herriot Tabuteau Assignee: Antecip Bioventures II LLC.
U.S. Appl. No. 15/378,939, filed Dec. 14, 2016 First Named Inventor: Herriot Tabuteau Assignee: Antecip Bioventures II LLC.
U.S. Appl. No. 15/380,824, filed Dec. 15, 2016 First Named Inventor: Herriot Tabuteau Assignee: Antecip Bioventures II LLC.
U.S. Appl. No. 15/384,125, filed Dec. 19, 2016 First Named Inventor: Herriot Tabuteau Assignee: Antecip Bioventures II LLC.
U.S. Appl. No. 16/439,121, filed Jun. 12, 2019, First Named Inventor: Herriot Tabuteau, Assignee: Antecip Bioventures II LLC.
U.S. Appl. No. 16/452,910, filed Jun. 26, 2019, First Named Inventor: Herriot Tabuteau, Assignee: Antecip Bioventures II LLC.

NERIDRONIC ACID AND OTHER BISPHOSPHONATES FOR TREATING COMPLEX REGIONAL PAIN SYNDROME AND OTHER DISEASES

CROSS-REFERENCE TO RELATED APPLICATIONS

This application is a continuation-in-part of U.S. patent application Ser. No. 16/110,869, filed Aug. 23, 2018; which is a continuation-in-part of U.S. patent application Ser. No. 15/710,759, filed Sep. 20, 2017, now U.S. Pat. No. 10,080,765; which is a continuation-in-part of U.S. patent application Ser. No. 15/587,246, filed May 4, 2017, now U.S. Pat. No. 9,782,421; which is a continuation-in-part of U.S. patent application Ser. No. 15/384,125, filed Dec. 19, 2016, now U.S. Pat. No. 9,655,908; which claims the benefit of U.S. Prov. App. No. 62/431,287, filed Dec. 7, 2016; the above U.S. patent application Ser. No. 15/384,125 is also a continuation-in-part of U.S. patent application Ser. No. 15/357,932, filed Nov. 21, 2016, now U.S. Pat. No. 9,707,245; which is a continuation-in-part of International Pat. App. No. PCT/US2015/032739, filed May 27, 2015, which is a continuation of International Pat. App. No. PCT/US2014/050427, filed Aug. 8, 2014, which is a continuation of U.S. patent application Ser. No. 14/279,241, filed May 15, 2014, now abandoned; the above U.S. patent application Ser. No. 15/357,932 is also a continuation-in-part of U.S. patent application Ser. No. 14/530,556, filed Oct. 31, 2014, now abandoned; which is a continuation-in-part of U.S. patent application Ser. No. 14/279,229, filed May 15, 2014, now U.S. Pat. No. 9,034,889; which is a continuation of U.S. patent application Ser. No. 14/063,979, filed Oct. 25, 2013, now U.S. Pat. No. 8,802,658; which is a continuation-in-part of U.S. patent application Ser. No. 13/894,274, filed May 14, 2013, now abandoned; which claims the benefit of Prov. App. Nos. 61/646,538, filed May 14, 2012; 61/647,478, filed May 15, 2012; 61/654,292, filed Jun. 1, 2012; 61/654,383, filed Jun. 1, 2012; 61/655,527, filed Jun. 5, 2012; 61/655,541, filed Jun. 5, 2012; 61/764,563, filed Feb. 14, 2013; 61/762,225, filed Feb. 7, 2013; 61/767,647, filed Feb. 21, 2013; 61/767,676, filed Feb. 21, 2013; and 61/803,721, filed Mar. 20, 2013; the above U.S. patent application Ser. No. 15/384,125 is also a continuation-in-part of U.S. patent application Ser. No. 14/457,659, filed Aug. 12, 2014, now abandoned; the above U.S. patent application Ser. No. 15/384,125 is also a continuation-in-part of U.S. patent application Ser. No. 15/371,052, filed Dec. 6, 2016, now abandoned; and the above U.S. patent application Ser. No. 15/384,125 is also a continuation-in-part of U.S. patent application Ser. No. 15/136,092, filed Apr. 22, 2016, now U.S. Pat. No. 9,616,078; which claims the benefit of U.S. Prov. App. No. 62/150,871, filed Apr. 22, 2015; this application is also a continuation-in-part of Ser. No. 16/222,040, filed Dec. 17, 2018; which is a continuation of U.S. patent application Ser. No. 16/152,256, filed Oct. 4, 2018; which is a continuation of U.S. patent application Ser. No. 15/963,878, filed Apr. 26, 2018, now U.S. Pat. No. 10,117,880; which is a continuation of U.S. patent application Ser. No. 15/820,305, filed Nov. 21, 2017, now U.S. Pat. No. 10,052,338; which is a continuation of U.S. patent application Ser. No. 15/703,891, filed Sep. 13, 2017, now U.S. Pat. No. 9,931,352; which is a continuation-in-part of U.S. patent application Ser. No. 15/647,140, filed Jul. 11, 2017, now U.S. Pat. No. 9,820,999; which is a continuation-in-part of U.S. patent application Ser. No. 15/357,932, filed Nov. 21, 2016, now U.S. Pat. No. 9,707,245; this application also claims the benefit of U.S. Prov. Pat. App. No. 62/802,107, filed Feb. 6, 2019; any of the above applications, U.S. patents issued from, or U.S. publications of any of the above applications are incorporated by references in their entirety.

FIELD

This disclosure relates to bisphosphonates, such as neridronic acid or neridronate, zoledronic acid or zoledronate, for treating diseases such as complex regional pain syndrome (CRPS).

BACKGROUND

Bisphosphonate compounds are potent inhibitors of osteoclast activity, and are used clinically to treat bone-related conditions such as osteoporosis and Paget's disease of bone; and cancer-related conditions including multiple myeloma, and bone metastases from solid tumors. They generally have low oral bioavailability.

Patchy osteoporosis and bone marrow edema may result from osteoclast hyperactivity. Zoledronic acid is a potent inhibitor of bone resorption and osteoclast activity. Nitrogen containing bisphosphonates, such as zoledronic acid, also inhibit the mevalonate pathway in the osteoclast thereby interrupting normal osteoclast function.

Complex Regional Pain Syndrome (CRPS) is a debilitating condition characterized by severe, continuous, burning or throbbing pain often occurring in an extremity after injury or surgery. The excessive pain is accompanied by changes in skin color, temperature and/or swelling/edema. It is persistent, considered to be one of the most painful conditions a patient can experience (Tahmoush A J. Causalgia: redefinition as a clinical pain syndrome. Pain. 1981 April; 10(2): 187-97), results in loss of physical function, and can lead to significant and sometimes permanent disability. Complex Regional Pain Syndrome (CRPS) is a rare condition that typically affects patients following a soft tissue, bone, or nerve injury. Patients with CRPS have to live with very severe and persistent pain, Classic analgesics offer only limited symptomatic relief, and currently no sufficiently effective treatments are available. For this reason, people with CRPS report lower quality of life scores than patients with most other chronic pain conditions. Patients frequently become socially isolated, lose their employment, and/or suffer from depression.

CRPS is a disease affecting less than 200,000 people with severe, persistent pain without sufficiently effective treatment options today. With no FDA- or EMA-approved drug treatments of CRPS today, there is a clear need for effective treatment options to address this significant unmet medical need.

One of the bisphosphonates, neridronate, is an innovative new medicine that may bring hope to CRPS patients.

SUMMARY

It has been discovered that oral dosage forms comprising a bisphosphonate compound, such as zoledronic acid, neridronic acid, or another bisphosphonate can be used to treat or alleviate pain or related conditions.

Some embodiments include a method of treating complex regional pain syndrome comprising administering an oral dosage form containing neridronic acid to a mammal in need thereof.

DETAILED DESCRIPTION

Figure 1:
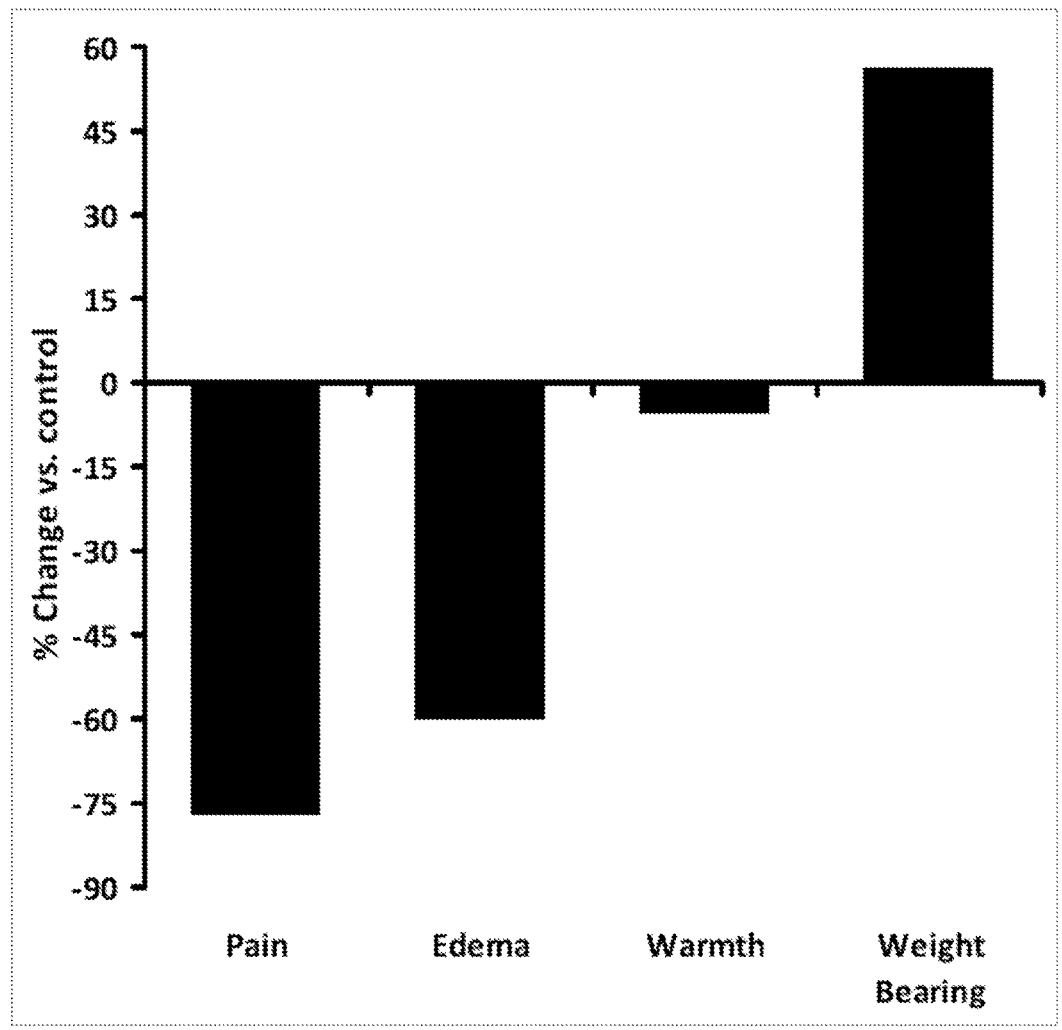
FIG. 1 is a graph summarizing the results for vehicle and zoledronic acid treated rats in a rat model of complex regional pain syndrome.

The term "treating" or "treatment" broadly includes any kind of treatment activity, including the cure, mitigation, or prevention of disease in man or other animals, or any activity that otherwise affects the structure or any function of the body of man or other animals.

The oral dosage forms comprising a bisphosphonate compound, such as zoledronic acid, neridronic acid, or another bisphosphonate may also be used to treat bone fractures or to enhance the healing of bone fractures.

General

Neridronic acid may be used to treat CRPS in a human being who has been diagnosed as having CRPS according to the clinical diagnostic criteria recommended by the International Association for the Study of Pain (IASP). Current criteria are known as Budapest criteria and were updated compared to the earlier 1994 IASP criteria resulting in increased specificity with comparable sensitivity (Harden et al., Pain 2010. 150; 268-74).

In some embodiments, neridronic acid is administered to treat a human being who is suffering from CRPS, wherein the human being is diagnosed with CRPS-I according to the Budapest clinical criteria In some embodiments, neridronic acid is administered to treat a human being who is suffering from CRPS who meets the Budapest criteria.

In some embodiments, neridronic acid is administered to treat a human being who is suffering from CRPS who meets the published 1994 IASP criteria. In some embodiments, neridronic acid is administered to treat a human being who is suffering from CRPS who has signs and symptoms of CRPS that apply to an affected limb (arm or leg) and has demonstrated asymmetry with respect to the contralateral limb. In some embodiments, neridronic acid is administered to treat a human being who is suffering from CRPS who has had CRPS for 2 years or less since onset of symptoms.

Complex regional pain syndrome is a debilitating pain syndrome. A human being who is treated with neridronic acid may have CRPS that is characterized by severe pain in a limb that can be accompanied by edema, and autonomic, motor and sensory changes.

A human being who is treated with neridronic acid may have Complex Regional Pain Syndrome (CRPS) that occurs after limb trauma and is associated with disproportionate pain, motor, sensory, trophic and autonomic changes. CRPS can be differentiated by the absence (CRPS-I) or presence (CRPS-II) of evident nerve lesions.

CRPS was reported to have an incidence rate of 5.46 per 100,000 person years at risk, and a period prevalence of 20.57 per 100,000 in the US (Sandroni et al., Pain 2003. 103: 199-207).

Type of CRPS

There are a few different types of complex regional pain syndrome, such as complex regional pain syndrome type I (CRPS-I), complex regional pain syndrome type II (CRPS-II), CRPS-NOS, or another type of CRPS, that may be treated by administering neridronic acid. Neridronic acid may be used to treat warm CRPS. Alternatively, neridronic acid may be used to treat cold CRPS.

Precipitating Event

Neridronic acid may be used to treat CRPS caused by any of a number of known precipitating events. The phrase "known precipitating event" indicates a precipitating event that the patient was known to have with respect to the CRPS. Such precipitating events include a bone fracture, a cutting injury, a scratch, a puncture injury, etc.

In some embodiments, neridronic acid is administered to treat a human being who is suffering from CRPS-I who has a known precipitating event prior to the onset of symptoms of CRPS-I. In some embodiments, the known precipitating event is surgery. In some embodiments, the known precipitating event is fracture. In some embodiments, the known precipitating event is sprain. In some embodiments, the known precipitating event is crush. In some embodiments, the known precipitating event is contusion. In some embodiments, the known precipitating event is dislocation. In some embodiments, the known precipitating event is an event other than, surgery, fracture, sprain, crush, contusion, or dislocation.

In some embodiments, neridronic acid is administered to treat a human being who is suffering from CRPS-II who has a known precipitating event prior to the onset of symptoms of CRPS-II. In some embodiments, the known precipitating event is surgery. In some embodiments, the known precipitating event is fracture. In some embodiments, the known precipitating event is sprain. In some embodiments, the known precipitating event is crush. In some embodiments, the known precipitating event is contusion. In some embodiments, the known precipitating event is dislocation. In some embodiments, the known precipitating event is an event other than, surgery, fracture, sprain, crush, contusion, or dislocation.

Time Between Precipitating Event Associated with CRPS and Administration

In some embodiments, the time between a precipitating event associated with CRPS and the administration of neridronic acid is at least 4 weeks, at least 8 weeks, at least 12 weeks, at least six months, or at least 1 year.

Signs/Symptoms

The effectiveness of the use of neridronic acid to treat CRPS type I may be affected by inciting event, location, signs and symptoms of CRPS, and/or CRPS duration.

In some embodiments, neridronic acid is administered to treat a human being who is suffering from CRPS-I, wherein disproportionate pain is a symptom of the CRPS-I. In some embodiments, neridronic acid is administered to treat a human being who is suffering from CRPS-I, wherein sensory changes is a symptom of the CRPS-I. In some embodiments, neridronic acid is administered to treat a human being who is suffering from CRPS-I, wherein autonomic changes is a symptom of the CRPS-I. In some embodiments, neridronic acid is administered to treat a human being who is suffering from CRPS-I, wherein hyperesthesia is a symptom of the CRPS-I. In some embodiments, neridronic acid is administered to treat a human being who is suffering from CRPS-I, wherein hyperalgesia is a symptom of the CRPS-I. In some embodiments, neridronic acid is administered to treat a human being who is suffering from CRPS-I, wherein pinprick hyperalgesia is a symptom of the CRPS-I. In some embodiments, neridronic acid is administered to treat a human being who is suffering from CRPS-I, wherein allodynia is a symptom of the CRPS-I. In some embodiments, neridronic acid is administered to treat a human being who is suffering from CRPS-I, wherein temperature asymmetry is a symptom of the CRPS-I. In some embodiments, neridronic acid is administered to treat a human being who is suffering from CRPS-I, wherein skin color asymmetry is a symptom of the CRPS-I. In some embodiments, neridronic acid is administered to treat a human being who is suffering from CRPS-I, wherein sweating asymmetry is a symptom of the CRPS-I. In some embodiments, neridronic acid is administered to treat a human being who is suffering from CRPS-I, wherein edema is a symptom of the CRPS-I. In some embodiments, neridronic acid is administered to treat a human being who is suffering from CRPS-I, wherein asymmetric edema is a symptom of the CRPS-I. In some embodiments, neridronic acid is administered to treat a human being who is suffering from CRPS-I, wherein trophic changes is a symptom of the CRPS-I. In some embodiments, neridronic acid is administered to treat a human being who is suffering from CRPS-I, wherein motor changes is a symptom of the CRPS-I. In some embodiments, the CRPS-I patient is selected for the symptom, e.g. hyperalgesia, pinprick hyperalgesia, allodynia, temperature asymmetry, skin color asymmetry, sweating asymmetry, asymmetric edema, tropic changes, motor changes, etc. In some embodiments, neridronic acid is administered to a human being with CRPS-I who has, or is selected for having, asymmetry with respect to hyperalgesia, pinprick hyperalgesia, allodynia, tropic changes, motor changes, or another sign or symptom of CRPS, e.g. with respect to the contralateral limb.

In some embodiments, neridronic acid is administered to treat a human being who is suffering from CRPS, wherein the human being has allodynia, or is selected for having allodynia. In some embodiments, neridronic acid is administered to treat a human being who is suffering from CRPS, wherein the human being has hyperalgesia, or is selected for having hyperalgesia. In some embodiments, neridronic acid is administered to treat a human being who is suffering from CRPS, wherein the human being has pinprick hyperalgesia, or is selected for having pinprick hyperalgesia. In some embodiments, neridronic acid is administered to treat a human being who is suffering from CRPS, wherein the human being has temperature asymmetry, or is selected for having temperature asymmetry. In some embodiments, neridronic acid is administered to treat a human being who is suffering from CRPS, wherein the human being has skin color asymmetry, or is selected for having skin color asymmetry. In some embodiments, neridronic acid is administered to treat a human being who is suffering from CRPS, wherein the human being has sweating asymmetry, or is selected for having sweating asymmetry. In some embodiments, neridronic acid is administered to treat a human being who is suffering from CRPS, wherein the human being has edema, or is selected for having edema. In some embodiments, neridronic acid is administered to treat a human being who is suffering from CRPS, wherein the human being has dystrophic changes, or is selected for having dystrophic changes. In some embodiments, neridronic acid is administered to treat a human being who is suffering from CRPS, wherein the human being has skin changes, or is selected for having skin changes. In some embodiments, neridronic acid is administered to treat a human being who is suffering from CRPS, wherein the human being has nail changes, or is selected for having nail changes. In some embodiments, neridronic acid is administered to treat a human being who is suffering from CRPS, wherein the human being has hair changes, or is selected for having hair changes. In some embodiments, neridronic acid is administered to treat a human being who is suffering from CRPS, wherein the human being has motor abnormalities, or is selected for having motor abnormalities.

In some embodiments, neridronic acid is administered to treat a human being who is suffering from CRPS, wherein the human being has or is selected for having allodynia, hyperalgesia, pinprick hyperalgesia, temperature asymmetry, skin color asymmetry, sweating asymmetry, edema, dystrophic changes, skin changes, nail changes, hair changes, or motor abnormalities.

Time of CRPS

The frequencies of CRPS symptoms decrease significantly over the first 6 to 13 months, but the outcomes of CRPS are highly variable, and there is a group of patients whose pain and sensory symptoms persist in the long term.

In some embodiments, the patient has CRPS for at least 1 month, at least 2 months, at least 3 months, at least 6 months, or at least 1 year prior to the treatment of neridronic acid.

Early CRPS may be much more responsive to different forms of pharmacological treatment than chronic CRPS. In some embodiments, neridronic acid is administered to treat CRPS in a human being who has had CRPS, or has been diagnosed with CRPS, for less than about 10 years, less than about 5 years, less than about 4 years, less than about 3 years, less than about 2 years, less than about 1 year, less than about 11 months, less than about 10 months, less than about 9 months, less than about 8 months, less than about 7 months, less than about 6 months, less than about 5 months less than about 4 months, less than about 3 months, less than about 2 months, less than about 1 month, about 0-2 months, about 2-4 months, about 4-6 months, about 6-8 months, about 8-10 months, about 10-12 months, about 1-2 years, about 2-3 years, about 3-4 years, about 4-5 years, about 5-6 years, about 6-7 years, about 7-8 years, about 8-9 years, about 9-10 years, about 0-4 months, about 0-8 months, about 8-12 months, about 1-3 years, about 3-5 years, about 0-6 months, about 6-12 months, about 1-5 years, about 5-10 years, or over 10 years.

In some embodiments, the patient being treated with neridronic acid has had CRPS, has had CRPS symptoms, or has been diagnosed with CRPS, for 2 years or less. In some embodiments, the patient being treated has had CRPS, or has been diagnosed with CRPS, for more than about 2 years.

Age of Patient

Neridronic acid can be used to treat CRPS in patients at various ages, such as an age of at least 18 years, at least 50 years (including a male of at least 50 years), a postmenopausal female, about 10 years to about 90 years, about 20 years to about 80 years, about 30 years to about 75 years, about 40 years to about 70 years, about 1 year to about 16 years, about 80 years to about 95 years, or over 90 years.

Neridronic acid can be used to treat CRPS in a human being who has an age of about 0-18 years, about 18-80 years, about 18-30 years, about 30-40 years, about 40-50 years, about 50-60 years, about 60-70 years, about 70-80 years, about 80-90 years, or any age.

In some embodiments, neridronic acid is used to treat CRPS in a human being who is at least 18 years of age.

Gender

In some embodiments, the human being who is treated for CRPS with neridronic acid is female. In some embodiments, the female human being is not pregnant.

In some embodiments, the human being who is treated for CRPS with neridronic acid is male.

In some embodiments, the human being who is treated for CRPS with neridronic acid has a weight that is at least 30 kg, at least 35 kg, at least 40 kg, at least 45 kg, at least 50 kg, at least 55 kg, or at least 60 kg.

Pain Intensity

In some embodiments, the person has baseline average pain intensity of 4 or greater measured using the 0-10 numerical rating scale (NRS), using an 11-point NRS, referring to the CRPS-affected limb (average of pain recorded over 7 days); or 40 mm or greater using the 100 mm visual analog scale (VAS), prior to the treatment of CRPS with the dosage form comprising neridronic acid.

In some embodiments, the person has baseline pain intensity of 5 or greater measured using the 0-10 numerical rating scale (NRS), or 50 mm or greater using the 100 mm visual analog scale (VAS) prior to the treatment of CRPS with the dosage form comprising neridronic acid.

Commonly used measures of pain intensity include the visual analog scale (VAS) and the numerical rating scale (NRS). With the VAS approach, patients rate the severity of their pain by marking a point on a 10-cm (or 100 mm) VAS (0=no pain and 10 cm=worst possible pain). With the NRS approach, patients rate the severity of their pain by verbally responding to an 11-point NRS (0=no pain and 10=worst possible pain). For example, the patient reports NRS pain value once daily (in the evening, 24-hour recall) in an electronic diary, then the weekly average of NRS pain value can be calculated based on the change from the baseline phase, that is from Day-7 to Day-1. VAS and NRS scores have been shown to be strongly correlated (slope of regression line, 1.01), indicating that a score on the 10-cm VAS is equivalent to the same score on the 11-point NRS (Bijur P E et al. Acad Emerg Med 2003; 10:390-392). For example, a VAS score of 5 cm (or 50 mm) is equivalent to an NRS score of 5. Knee pain in a person with a VAS score of 5 cm or 50 mm or higher, or an NRS score of 5 or higher, may be referred to herein as moderate to severe pain.

In some embodiments, for the patient who has mechanical allodynia (DMA), the pain intensity level of dynamic mechanical allodynia (DMA) can also use NRS. For example, for a patient who has dynamic mechanical allodynia, a tactile stimulus can be applied in a single sweeping motion (1 cm to 2 cm length) on the skin on the affected limb. The patient then judges the stimulus intensity by means of an NRS (0 to 10). "0" in this case means "no pain". Each "pricking", "stinging" or "burning" sensation is defined as a painful sensation, which should always be evaluated by giving a value greater than "0". "10" corresponds to the individual maximum pain imaginable.

Other pain intensity measurement may include pressure pain threshold (PPT). In some embodiments, pressure pain threshold is measured using a pressure algometer. For example, the threshold for pressure-induced pain can be measured on the tenar muscle/abductor hallucis muscle in 3 series of slowly increasing stimulus intensities (at a rate of about 50 kPa/s), on both the affected limb and the unaffected limb. The threshold is then determined as the arithmetic mean of the 3 series (in kPa). The ratio of the thresholds (PPT ratio) of the affected limb versus the unaffected limb can be then calculated.

In some embodiments, e.g. at baseline or the start of treatment, the human CRPS patient being treated with neridronic acid has an NRS of at least about 4, at least about 5, at least about 6, at least about 7, at least about 8, at least about 9 or greater, about 1-2, about 2-3, about 3-4, about 4-5, about 5-6, about 6-7, about 7-8, about 8-9, about 9-10, or about 10.

In some embodiments, e.g. at baseline or the start of treatment, the human CRPS patient being treated with neridronic acid has a VAS of at least about 4 cm, at least about 5 cm, at least about 6 cm, at least about 7 cm, at least about 8 cm, or at least about 9, cm, about 1-2 cm, about 2-3 cm, about 3-4 cm, about 4-5 cm, about 5-6 cm, about 6-7 cm, about 7-8 cm, about 8-9 cm, about 9-10 cm, or about 10 cm.

In some embodiments, the human CRPS patient being treated with neridronic acid has ongoing moderate to severe chronic pain, including a baseline current pain intensity score of at least about 4 or greater using an 11-point Numerical Rating Scale (NRS) referring to the CRPS-affected limb prior to administration of a dosage form comprising neridronic acid.

In some embodiments, treatment of a human CRPS patient with neridronic acid may decrease the visual analog (VAS) pain score, or the EuroQol visual analog scale (EQ VAS) measured using a 100 mm scale, by at least about 1 mm, at least about 5 mm, at least about 10 mm, at least about 15 mm, at least about 20 mm, at least about 25 mm, at least about 30 mm, at least about 35 mm, at least about 40 mm, at least about 45 mm, at least about 50 mm, at least about 55 mm, at least about 60 mm, at least about 65 mm, at least about 70 mm, at least about 80 mm, at least about 90 mm, about 1-10 mm, about 10-20 mm, about 20-30 mm, about 30-40 mm, about 40-50 mm, about 50-60 mm, about 60-70 mm, about 70-80 mm, about 80-90 mm, about 90-100 mm, about 1-30 mm, about 30-60 mm, or about 60-100 mm. In some embodiments, treatment of a human CRPS patient with neridronic acid may decrease the VAS or EQ VAS pain score by at least about 10%, at least about 20%, at least about 30%, at least about 40%, at least about 50%, at least about 60%, at least about 70%, at least about 80%, or at least about 90%, as compared to baseline, or as compared to a placebo. The improvement may be observed at 1 day, 7 days, two weeks, 1 month, 6 weeks, 2 months, 3 months, 12 weeks, 4 months, 5 months, 6 months, 26 weeks, 7 months, 8 months, 9 months, 39 weeks, 10 months, 11 months, 12 months, 52 weeks, or longer.

In some embodiments, treatment of a human CRPS patient with neridronic acid may decrease the numeric rating scale (NRS) pain score, the current pain intensity, the average pain intensity, the pain intensity score, the pain intensity scores at each week, the pain intensity level of dynamic mechanical allodynia, or the worst pain intensity, measured using a 0-10 scale, by at least about 0.5, at least about 1, at least about 1.5, at least about 2, at least about 2.5, at least about 3, at least about 3.5, at least about 4, at least about 4.5, at least about 5, at least about 5.5, at least about 6, at least about 6.5, at least about 7, at least about 8, at least about 9, about 0.1-1, about 1-2, about 2-3, about 3-4, about 4-5, about 5-6, about 6-7, about 7-8, about 8-9, about 9-10, about 1-3, about 3-6, or about 6-10. In some embodiments, treatment of the human CRPS patient with neridronic acid may decrease the NRS pain score, the average pain intensity, the pain intensity score, the pain intensity scores at each week, the pain intensity level of dynamic mechanical allodynia, or the worst pain intensity, by at least about 10%, at least about 20%, at least about 30%, at least about 40%, at least about 50%, at least about 60%, at least about 70%, at least about 80%, or at least about 90%, as compared to baseline, or as compared to a placebo. The improvement may be observed at 1 day, 7 days, two weeks, 1 month, 6 weeks, 2 months, 3 months, 12 weeks, 4 months, 5 months, 6 months, 26 weeks, 7 months, 8 months, 9 months, 39 weeks, 10 months, 11 months, 12 months, 52 weeks, or longer.

In some embodiments, treatment a human CRPS patient with neridronic acid, such as by intravenous administration, may decrease the numeric rating scale (NRS) pain score by at least 30% from baseline in the average pain intensity at Week 12. In some embodiments, treatment of a human CRPS patient with neridronic acid, such as by intravenous administration, may decrease the numeric rating scale (NRS) pain score by at least 30% from baseline in the average pain intensity at Week 26. In some embodiments, the treatment with intravenous neridronic acid in the human beings with CRPS may last up to 60 days. In some embodiments, the treatment with intravenous neridronic acid consists 4 infusions of neridronic acid over 10 days.

In some embodiments, treatment of a human CRPS patient with neridronic acid may reduce the pain intensity level of dynamic mechanical allodynia (DMA), as compared to the baseline, by at least about 10%, at least about 20%, at least about 30%, at least about 40%, at least about 50%, at least about 60%, at least about 70%, at least about 80%, or at least about 90%. The improvement may be observed at 1 day, 7 days, two weeks, 1 month, 6 weeks, 2 months, 3 months, 12 weeks, 4 months, 5 months, 6 months, 26 weeks, 7 months, 8 months, 9 months, 39 weeks, 10 months, 11 months, 12 months, 52 weeks, or longer.

In some embodiments, treatment of a human CRPS patient with neridronic acid may increase the pressure pain threshold (PPT) ratio for the tenar muscle/abductor hallucis muscle, as compared to the baseline, by at least about 10%, at least about 20%, at least about 30%, at least about 40%, at least about 50%, at least about 60%, at least about 70%, at least about 80%, or at least about 90%. The improvement may be observed at 1 day, 7 days, two weeks, 1 month, 6 weeks, 2 months, 3 months, 12 weeks, 4 months, 5 months, 6 months, 26 weeks, 7 months, 8 months, 9 months, 39 weeks, 10 months, 11 months, 12 months, 52 weeks, or longer.

In some embodiment, treatment of a human CRPS patient with neridronic acid may decrease the ratio of the figure-of-eight measurements of the affected limb versus the unaffected limb, as compared to the baseline, by at least about 10%, at least about 20%, at least about 30%, at least about 40%, at least about 50%, at least about 60%, at least about 70%, at least about 80%, or at least about 90%. The improvement may be observed at 1 day, 7 days, two weeks, 1 month, 6 weeks, 2 months, 3 months, 12 weeks, 4 months, 5 months, 6 months, 26 weeks, 7 months, 8 months, 9 months, 39 weeks, 10 months, 11 months, 12 months, 52 weeks, or longer.

In some embodiments, treatment of a human CRPS patient with neridronic acid may decrease the Brief Pain Inventory (BPI) score or the Pain Interference Score, measured using a 0-10 scale, by at least about 0.1, at least about 0.5, at least about 1, at least about 1.5, at least about 2, at least about 2.5, at least about 3, at least about 3.5, at least about 4, at least about 4.5, at least about 5, at least about 5.5, at least about 6, at least about 6.5, at least about 7, at least about 8, at least about 9, about 0.1-1, about 1-2, about 2-3, about 3-4, about 4-5, about 5-6, about 6-7, about 7-8, about 8-9, about 9-10, about 1-3, about 3-6, or about 6-10. In some embodiments, treatment of a human CRPS patient with neridronic acid may decrease the BPI score or the Pain Interference Score by at least about 10%, at least about 20%, at least about 30%, at least about 40%, at least about 50%, at least about 60%, at least about 70%, at least about 80%, or at least about 90%, as compared to baseline, or as compared to a placebo. The improvement may be observed at 1 day, 7 days, two weeks, 1 month, 6 weeks, 2 months, 3 months, 12 weeks, 4 months, 5 months, 6 months, 26 weeks, 7 months, 8 months, 9 months, 39 weeks, 10 months, 11 months, 12 months, 52 weeks, or longer.

In some embodiments, treatment of a human CRPS patient with neridronic acid may result in a Patient Global Impression of Change (PGIC) of much improved or very much improved. The improvement may be observed at 1 day, 7 days, two weeks, 1 month, 6 weeks, 2 months, 3 months, 12 weeks, 4 months, 5 months, 6 months, 26 weeks, 7 months, 8 months, 9 months, 39 weeks, 10 months, 11 months, 12 months, 52 weeks, or longer.

In some embodiments, treatment of a human CRPS patient with neridronic acid may improve the patient's EuroQol-5 Dimension 5 Level (EQ-5D-5L) score, measured using a 0-1 scale, by at least about 0.1, at least about 0.15, at least about 0.2, at least about 0.25, at least about 0.3, at least about 0.35, at least about 0.4, at least about 0.45, at least about 0.5, at least about 0.55, at least about 0.6, at least about 0.65, at least about 0.7, at least about 0.8, at least about 0.9, about 0.01-0.1, about 0.1-0.2, about 0.2-0.3, about 0.3-0.4, about 0.4-0.5, about 0.5-0.6, about 0.6-0.7, about 0.7-0.8, about 0.8-0.9, about 0.9-0.10, about 0.1-0.3, about 0.3-0.6, or about 0.6-1. In some embodiments, treatment of a human CRPS patient with neridronic acid may improve the EQ-5D-5L score by at least about 40%, at least about 50%, at least about 60%, at least about 70%, at least about 80%, or at least about 90%, as compared to baseline, or as compared to a placebo. The improvement may be observed at 1 day, 7 days, two weeks, 1 month, 6 weeks, 2 months, 3 months, 12 weeks, 4 months, 5 months, 6 months, 26 weeks, 7 months, 8 months, 9 months, 39 weeks, 10 months, 11 months, 12 months, 52 weeks, or longer.

In some embodiments, treatment of a human CRPS patient with neridronic acid may decrease the Pain Anxiety Symptom Scale (PASS) Total Score, measured using a 0-100 scale, by at least about 1, at least about 5, at least about 10, at least about 15, at least about 20, at least about 25, at least about 30, at least about 35, at least about 40, at least about 45, at least about 50, at least about 55, at least about 60, at least about 65, at least about 70, at least about 80, at least about 90, about 1-10, about 10-20, about 20-30, about 30-40, about 40-50, about 50-60, about 60-70, about 70-80, about 80-90, about 90-100, about 1-30, about 30-60, or about 60-100. In some embodiments, treatment of a human CRPS patient with neridronic acid may decrease the PASS Total Score by at least about 10%, at least about 20%, at least about 30%, at least about 40%, at least about 50%, at least about 60%, at least about 70%, at least about 80%, or at least about 90%, as compared to baseline, or as compared to a placebo. The improvement may be observed at 1 day, 7 days, two weeks, 1 month, 6 weeks, 2 months, 3 months, 12 weeks, 4 months, 5 months, 6 months, 26 weeks, 7 months, 8 months, 9 months, 39 weeks, 10 months, 11 months, 12 months, 52 weeks, or longer.

In some embodiments, treatment of a human CRPS patient with neridronic acid may decrease the Center for Epidemiological Studies Depression (CES-D) Scale Total Score, measured using a 0-60 scale, by at least about 1, at least about 5, at least about 10, at least about 15, at least about 20, at least about 25, at least about 30, at least about 35, at least about 40, at least about 45, at least about 50, at least about 55, about 1-10, about 10-20, about 20-30, about 30-40, about 40-50, or about 50-60. In some embodiments, treatment of a human CRPS patient with neridronic acid may decrease the CES-D ScaleTotal Score by at least about 10%, at least about 20%, at least about 30%, at least about 40%, at least about 50%, at least about 60%, at least about 70%, at least about 80%, or at least about 90%, as compared to baseline, or as compared to a placebo. The improvement may be observed at 1 day, 7 days, two weeks, 1 month, 6 weeks, 2 months, 3 months, 12 weeks, 4 months, 5 months, 6 months, 26 weeks, 7 months, 8 months, 9 months, 39 weeks, 10 months, 11 months, 12 months, 52 weeks, or longer.

In some embodiments, treatment of a human CRPS patient with neridronic acid may decrease the Pain Disability Index (PDI), measured using a 0-70 scale, by at least about 1, at least about 5, at least about 10, at least about 15, at least about 20, at least about 25, at least about 30, at least about 35, at least about 40, at least about 45, at least about 50, at least about 55, at least about 60, at least about 65, about 1-10, about 10-20, about 20-30, about 30-40, about 40-50, about 50-60, or about 60-70. In some embodiments, treatment of a human CRPS patient with neridronic acid may decrease the PDI by at least about 10%, at least about 20%, at least about 30%, at least about 40%, at least about 50%, at least about 60%, at least about 70%, at least about 80%, or at least about 90%, as compared to baseline, or as compared to a placebo. The improvement may be observed at 1 day, 7 days, two weeks, 1 month, 6 weeks, 2 months, 3 months, 12 weeks, 4 months, 5 months, 6 months, 26 weeks, 7 months, 8 months, 9 months, 39 weeks, 10 months, 11 months, 12 months, 52 weeks, or longer.

In some embodiments, treatment of a human CRPS patient with neridronic acid may decrease Medical Outcomes Study (MOS) Sleep Scale: Sleep Problems Index, measured using a 0-100 scale, by at least about 1, at least about 5, at least about 10, at least about 15, at least about 20, at least about 25, at least about 30, at least about 35, at least about 40, at least about 45, at least about 50, at least about 55, at least about 60, at least about 65, at least about 70, at least about 80, at least about 90, about 1-10, about 10-20, about 20-30, about 30-40, about 40-50, about 50-60, about 60-70, about 70-80, about 80-90, about 90-100, about 1-30, about 30-60, or about 60-100. In some embodiments, treatment of a human CRPS patient with neridronic acid may decrease the MOS Sleep Scale Sleep Problems Index by at least about 10%, at least about 20%, at least about 30%, at least about 40%, at least about 50%, at least about 60%, at least about 70%, at least about 80%, or at least about 90%, as compared to baseline, or as compared to a placebo. The improvement may be observed at 1 day, 7 days, two weeks, 1 month, 6 weeks, 2 months, 3 months, 12 weeks, 4 months, 5 months, 6 months, 26 weeks, 7 months, 8 months, 9 months, 39 weeks, 10 months, 11 months, 12 months, 52 weeks, or longer.

In some embodiments, treatment of a human CRPS patient with neridronic acid may decrease the Complex Regional Pain Syndrome (CRPS) Severity Score measured using a 0-16 scale, by at least about 0.1, at least about 0.5, at least about 1, at least about 1.5, at least about 2, at least about 2.5, at least about 3, at least about 3.5, at least about 4, at least about 4.5, at least about 5, at least about 5.5, at least about 6, at least about 6.5, at least about 7, at least about 8, at least about 9, at least about 10, at least about 11, at least about 12, at least about 13, at least about 14, at least about 15, about 0.1-1, about 1-2, about 2-3, about 3-4, about 4-5, about 5-6, about 6-7, about 7-8, about 8-9, about 9-10, about 10-11, about 11-12, about 12-13, about 13-14, about 14-15, about 15-16, about 1-3, about 3-6, about 6-9, about 9-12, or about 12-16. In some embodiments, treatment of a human CRPS patient with neridronic acid may decrease the BPI score by at least about 10%, at least about 20%, at least about 30%, at least about 40%, at least about 50%, at least about 60%, at least about 70%, at least about 80%, or at least about 90%, as compared to baseline, or as compared to a placebo. The improvement may be observed at 1 day, about 7 days, about two weeks, about 1 month, about 6 weeks, about 2 months, about 3 months, about 12 weeks, about 4 months, about 5 months, about 6 months, about 26 weeks, about 7 months, about 8 months, about 9 months, about 39 weeks, about 10 months, about 11 months, about 12 months, about 52 weeks, or longer.

In some embodiments, treatment of a human CRPS patient with neridronic acid may achieve a reduction in pain that lasts at least about 1 day, about 7 days, about two weeks, about 1 month, about 6 weeks, about 2 months, about 3 months, about 12 weeks, about 4 months, about 5 months, about 6 months, about 26 weeks, about 7 months, about 8 months, about 9 months, about 39 weeks, about 10 months, about 11 months, about 12 months, about 52 weeks, or longer.

The relief of pain can be short-term, e.g. for a period of hours after administration of the dosage form, and/or relief of pain can be long-term, e.g. lasting for days, weeks, or even months after oral administration of zoledronic acid. In some embodiments, a mammal, such as a human being, experiences significant pain relief at least about 3 hours, at least about 6 hours, at least about 12 hours, at least about 24 hours, at least about 48 hours, at least about one week, at least about 2 weeks, or at least about 3 weeks after administration of an oral dosage form comprising zoledronic acid. In some embodiments, a mammal, such as a human being, experiences significant pain relief during at least part of the time from about 3 hours to about 2 weeks, about 3 hours to about 3 weeks, about 3 hours to about 24 hours, about 6 hours to about 2 weeks, or about 6 hours to about 24 hours, about 3 days to about 2 weeks, about 6 days to about 2 weeks, after administration of an oral dosage form comprising zoledronic acid. In some embodiments, a human being treated has significant pain relief at about one month, about three months, about six months, about nine months, about one year, about 5 years, or longer, after administration of the most recent dose In some embodiments, neridronic acid is administered to treat a human being who is suffering from CRPS, wherein the human being has a baseline pain intensity score of at least about 4 on an 11-point Numerical Rating Scale (NRS).

In some embodiments, neridronic acid is administered to treat a human being who is suffering from CRPS, wherein the human being has been on stable CRPS treatment for at least 1 month prior receiving neridronic acid.

In some embodiments, neridronic acid is administered to treat a human being who is suffering from CRPS, wherein the human being has failed trials of at least 2 treatments for CRPS, one of which is a pharmacologic treatment, before receiving neridronic acid.

In some embodiments, neridronic acid is administered to treat a human being who is suffering from CRPS, wherein the human being with vitamin D deficiency receives appropriate supplementation during the treatment period with neridronic acid.

In some embodiments, neridronic acid is administered to treat a human being who is suffering from CRPS, wherein the human being has a vitamin D level of at least 30 ng/mL (75 nmol/L).

In some embodiments, neridronic acid is administered to treat a human being who is suffering from CRPS, wherein the human being receives selective serotonin re-uptake inhibitor antidepressants (e.g., citalopram, escitalopram) or tricyclic antidepressants if the QT-interval values is low (e.g. lower than 470 milliseconds), and wherein the medication starts at least 1 month prior to treatment with neridronic acid, the dose is stable, and the dose is anticipated to remain stable at least throughout the treatment with neridronic acid, for example until at least 4 days after the last infusion of neridronic acid.

Edema

For the patient with the CRPS sign of edema on the CRPS severity score at baseline, the circumference of the hand or foot can be measured by the investigator, such as a doctor, with measurement tape using the figure-of-eight method known in the art at both the affected limb and the contralateral unaffected limb. Each measurement can be performed 3 times. The average of the 3 measurements is then used for further analysis. Thus, the ratio of the figure of eight measurements of the affected limb versus the unaffected limb can be calculated.

In some embodiments, treatment of a human CRPS patient with neridronic acid may reduce the ratio of the figure of eight measurements of the affected limb versus the unaffected limb at week 12 as compared to the baseline.

Location of CRPS

In some embodiments, neridronic acid is administered to treat a human being who is suffering from CRPS-I that affects the left side of the body. In some embodiments, neridronic acid is administered to treat a human being who is suffering from CRPS-I that affects the right side of the body. In some embodiments, neridronic acid is administered to treat a human being who is suffering from CRPS-I that affects the lower extremity or lower limb. In some embodiments, neridronic acid is administered to treat a human being who is suffering from CRPS-I that affects the upper extremity or upper limb. In some embodiments, the CRPS affects more than 1 limb. In some embodiments, the human being is selected for the location where the CRPS-I is located, e.g. left side, right side, upper extremity, upper limb, lower extremity, lower limb, etc.

In some embodiments, neridronic acid is administered to treat a human being who is suffering from CRPS-II that affects the left side of the body. In some embodiments, neridronic acid is administered to treat a human being who is suffering from CRPS-II that affects the right side of the body. In some embodiments, neridronic acid is administered to treat a human being who is suffering from CRPS-II that affects the lower extremity or lower limb. In some embodiments, neridronic acid is administered to treat a human being who is suffering from CRPS-II that affects the upper extremity or upper limb. In some embodiments, the CRPS affects more than 1 limb. In some embodiments, the human being is selected for the location where the CRPS-II is located, e.g. left side, right side, upper extremity, upper limb, lower extremity, lower limb, etc.

Neridronic acid may be more effective in treating CRPS in patients that have had the disease for less than two years and that have CRPS affecting 1 limb. Neridronic acid may be more effective in treating CRPS in patients that have had the disease for less than two years and that have CRPS affecting 2 limbs. Neridronic acid may be more effective in treating CRPS in patients that have had the disease for less than two years and that have CRPS affecting 3 limbs. Neridronic acid may be more effective in treating CRPS in patients that have had the disease for less than two years and that have CRPS affecting 4 limbs.

Neridronic acid may be more effective in treating CRPS in patients that have had the disease for more than two years and that have CRPS affecting 1 limb. Neridronic acid may be more effective in treating CRPS in patients that have had the disease for more than two years and that have CRPS affecting 2 limbs. Neridronic acid may be more effective in treating CRPS in patients that have had the disease for more than two years and that have CRPS affecting 3 limbs. Neridronic acid may be more effective in treating CRPS in patients that have had the disease for more than two years and that have CRPS affecting 4 limbs.

Comorbidities

In some embodiments, neridronic acid is administered to treat a human being who is suffering from CRPS, wherein the human being does not have a severe renal condition. In some embodiments, neridronic acid is administered to treat a human being who is suffering from CRPS, wherein the human being does not have a cardiovascular condition. In some embodiments, neridronic acid is administered to treat a human being who is suffering from CRPS, wherein the human being does not have a liver condition. In some embodiments, neridronic acid is administered to treat a human being who is suffering from CRPS, wherein the human being does not have a dental pathology. In some embodiments, neridronic acid is administered to treat a human being who is suffering from CRPS, wherein the human being does not have any severe medical condition. In some embodiments, neridronic acid is administered to treat a human being who is suffering from CRPS, wherein the human being does not have a severe renal, cardiovascular, liver and dental pathology or other severe medical condition. In some embodiments, neridronic acid is administered to treat a human being who is suffering from CRPS, wherein the human being does not have a history and/or diagnosis of peripheral neuropathy. In some embodiments, neridronic acid is administered to treat a human being who is suffering from CRPS, wherein the human being does not have a history and/or diagnosis of diabetic peripheral neuropathy. In some embodiments, neridronic acid is administered to treat a human being who is suffering from CRPS, wherein the human being does not have a history and/or diagnosis of a metabolic neuropathy. In some embodiments, neridronic acid is administered to treat a human being who is suffering from CRPS, wherein the human being does not have a history and/or diagnosis of a toxic neuropathy. In some embodiments, neridronic acid is administered to treat a human being who is suffering from CRPS, wherein the human being does not have renal impairment (e.g. estimated glomerular filtration rate [eGFR] less than 60 mL/min/1.73 m$^2$ using the 2009 Chronic Kidney Disease Epidemiology Collaboration [CKD-EPI] creatinine equation [Levey et al. 2009] or a urinary albumin creatinine ratio greater than 150 mg/g). In some embodiments, neridronic acid is administered to treat a human being who is suffering from CRPS, wherein the human being does not have renal impairment (e.g. estimated glomerular filtration rate [eGFR] less than 30 mL/min/1.73 m$^2$ using the 2009 Chronic Kidney Disease Epidemiology Collaboration [CKD-EPI] creatinine equation [Levey et al. 2009] or a urinary albumin creatinine ratio greater than 150 mg/g). In some embodiments, neridronic acid is administered to treat a human being who is suffering from CRPS, wherein the human being does not have a history of chronic kidney disease. In some embodiments, neridronic acid is administered to treat a human being who is suffering from CRPS, wherein the human being does not have a vitamin D deficiency, defined as a 25(OH)D level less than 30 ng/mL (75 nmol/L). In some embodiments, neridronic acid is administered to treat a human being who is suffering from CRPS, wherein the human being has inability to normalize 25(OH)D levels to at least 30 ng/mL (75 nmol/L) despite appropriate supplementation. In some embodiments, neridronic acid is administered to treat a human being who is suffering from CRPS, wherein the human being does not have low serum calcium. In some embodiments, neridronic acid is administered to treat a human being who is suffering from CRPS, wherein the human being does not have high serum calcium. In some embodiments, neridronic acid is administered to treat a human being who is suffering from CRPS, wherein the human being does not have low serum magnesium. In some embodiments, neridronic acid is administered to treat a human being who is suffering from CRPS, wherein the human being does not have high serum magnesium. In some embodiments, neridronic acid is administered to treat a human being who is suffering from CRPS, wherein the human being does not have low serum potassium. In some embodiments, neridronic acid is administered to treat a human being who is suffering from CRPS, wherein the human being does not have high serum potassium. In some embodiments, neridronic acid is administered to treat a human being who is suffering from CRPS, wherein the human being does not have history of hypocalcemia. In some embodiments, neridronic acid is administered to treat a human being who is suffering from CRPS, wherein the human being does not have a metabolic disorder that increases risk for hypocalcemia (e.g., hypoparathyroidism). In some embodiments, neridronic acid is administered to treat a human being who is suffering from CRPS, wherein the human being does not have concomitant use of (or anticipated need for) any new drug(s) with known potential to cause hypocalcemia (e.g., aminoglycosides, new treatment with or dose adjustment of loop diuretics), although the human being on a stable dose of loop diuretics may receive treatment with IMP as long as no dosage increases in the diuretic medication are anticipated and calcium levels are in the reference range. In some embodiments, neridronic acid is administered to treat a human being who is suffering from CRPS, wherein the human being does not have a corrected QT interval (e.g. according to Fridericia's formula; QTcF) greater than 470 milliseconds (ms). In some embodiments, neridronic acid is administered to treat a human being who is suffering from CRPS, wherein the human being has not been treated with medications within the last 30 days that have potential to prolong the QT interval. In some embodiments, neridronic acid is administered to treat a human being who is suffering from CRPS, wherein the human being does not have an anticipated need for a medication that has the potential to prolong the QT interval. In some embodiments, neridronic acid is administered to treat a human being who is suffering from CRPS, wherein the human being does not have a history of allergic or hypersensitivity reaction to neridronic acid. In some embodiments, neridronic acid is administered to treat a human being who is suffering from CRPS, wherein the human being does not have a history of allergic or hypersensitivity reaction to another bisphosphonate. In some embodiments, neridronic acid is administered to treat a human being who is suffering from CRPS, wherein the human being does not have a history of allergic or hypersensitivity reaction to acetaminophen. In some embodiments, neridronic acid is administered to treat a human being who is suffering from CRPS, wherein the human being does not have a history of allergic or hypersensitivity reaction to vitamin D supplements. In some embodiments, neridronic acid is administered to treat a human being who is suffering from CRPS, wherein the human being does not have a history of allergic or hypersensitivity reaction to calcium supplements. In some embodiments, neridronic acid is administered to treat a human being who is suffering from CRPS, wherein the human being has not had recent tooth extraction. In some embodiments, neridronic acid is administered to treat a human being who is suffering from CRPS, wherein the human being has not had another invasive dental procedure within 3 months prior to the treatment with neridronic acid. In some embodiments, neridronic acid is administered to treat a human being who is suffering from CRPS, wherein the human being does not have an unhealed or infected extraction site. In some embodiments, neridronic acid is administered to treat a human being who is suffering from CRPS, wherein the human being does not have a significant dental/periodontal disease that may pre-dispose to need for tooth extraction or another invasive dental procedures during the treatment with neridronic acid. In some embodiments, neridronic acid is administered to treat a human being who is suffering from CRPS, wherein the human being does not have evidence of denture-related gum trauma or improperly fitting dentures causing injury. In some embodiments, neridronic acid is administered to treat a human being who is suffering from CRPS, wherein the human being does not have significant dental/periodontal disease (e.g., impacted molars, severe tooth decay, and foci of infection) that may predispose to need for tooth extraction or other invasive dental procedures during the treatment for CRPS. In some embodiments, neridronic acid is administered to treat a human being who is suffering from CRPS, wherein the human being does not have indeterminate, suspicious or unreliable dental history. In some embodiments, neridronic acid is administered to treat a human being who is suffering from CRPS, wherein the human being does not have clinically unstable cardiac disease, including: unstable atrial fibrillation, symptomatic bradycardia, unstable congestive heart failure, active myocardial ischemia, or an indwelling pacemaker; evidence of complete left bundle branch block; complete atrioventricular block; history of Long QT Syndrome or a relative with this condition; or any other known risk factor for torsade de pointes. In some embodiments, neridronic acid is administered to treat a human being who is suffering from CRPS, wherein the human being does not receive medications with a known risk of torsades de pointes within 7 days prior to treatment with neridronic acid.

In some embodiments, neridronic acid is administered to treat a human being who is suffering from CRPS, wherein the human being does not have any prior use of a bisphosphonate for treatment of CRPS, any prior administration of a bisphosphonate within the previous year, anticipated requirement for treatment with a bisphosphonate for another condition such as osteoporosis during the treatment with neridronic acid, or administration of denosumab (Prolia®) or other bone turnover suppressing drugs within 6 months prior to the treatment with neridronic acid.

In some embodiments, neridronic acid is administered to treat a human being who is suffering from CRPS, wherein the human being does not have prior radiation therapy of the head or neck (e.g. within 1 year of treatment). In some embodiments, neridronic acid is administered to treat a human being who is suffering from CRPS, wherein the human being has not had recent treatment with high doses of systemic steroids. In some embodiments, neridronic acid is administered to treat a human being who is suffering from CRPS, wherein the human being does not receive concomitant high-dose steroid treatment during treatment.

In some embodiments, neridronic acid is administered to treat a human being who is suffering from CRPS, wherein the human being does not have a history of malignancy within 2 years before treatment with the exception of basal cell carcinoma.

In some embodiments, neridronic acid is administered to treat a human being who is suffering from CRPS, wherein the human being does not have daily intake of long- and short-acting or controlled-release opioid analgesics of more than 200 mg morphine equivalents. In some embodiments, neridronic acid is administered to treat a human being who is suffering from CRPS, wherein the human being does not receive a combination of a high-dose opioid and a benzodiazepine. In some embodiments, neridronic acid is administered to treat a human being who is suffering from CRPS, wherein the human being does not have or any other treatment regimen considered unstable or unsafe.

In some embodiments, neridronic acid is administered to treat a human being who is suffering from CRPS, wherein a nerve block is not, or has not been (e.g. within 6 weeks of the starting treatment), used on the human being. In some embodiments, neridronic acid is administered to treat a human being who is suffering from CRPS, wherein the human being does not have, or has not had (e.g. within 6 weeks of starting treatment), a ketamine infusion. In some embodiments, neridronic acid is administered to treat a human being who is suffering from CRPS, wherein the human being does not have, or has not had (e.g. within 6 weeks of starting treatment), intravenous immunoglobulin. In some embodiments, neridronic acid is administered to treat a human being who is suffering from CRPS, wherein the human being does not have, or has not had (e.g. within 6 weeks of starting treatment) acupuncture. In some embodiments, neridronic acid is administered to treat a human being who is suffering from CRPS, wherein the human being does not have, or has not had (e.g. within 6 weeks of starting treatment) electromagnetic field treatment. In some embodiments, neridronic acid is administered to treat a human being who is suffering from CRPS, wherein the human being does not have, or has not had (e.g. within 6 weeks of starting treatment), initiation/implementation of radiofrequency ablation. In some embodiments, neridronic acid is administered to treat a human being who is suffering from CRPS, wherein the human being does not have, or has not had (e.g. within 6 weeks of starting treatment), a sympathectomy procedure. In some embodiments, neridronic acid is administered to treat a human being who is suffering from CRPS, wherein the human being does not have, or has not had (e.g. within 6 weeks of the starting treatment), a peripheral nerve stimulation. In some embodiments, neridronic acid is administered to treat a human being who is suffering from CRPS, wherein the human being is not taking forbidden concomitant medications/therapies or is able to follow the rules of use of concomitant treatment. In some embodiments, neridronic acid is administered to treat a human being who is suffering from CRPS, wherein the human being does not have abnormal level of serum calcium.

In some embodiments, neridronic acid is administered to treat a human being who is suffering from CRPS, wherein the human being does not have current alcohol or drug abuse, or history of alcohol or drug abuse within 2 years of starting treatment.

In some embodiments, neridronic acid is administered to treat a human being who is suffering from CRPS, wherein the human being does not have any other severe medical condition. In some embodiments, neridronic acid is administered to treat a human being who is suffering from CRPS, wherein the human being does not have severe depression. In some embodiments, neridronic acid is administered to treat a human being who is suffering from CRPS, wherein the human being does not have a severe mood disorder other than depression. In some embodiments, neridronic acid is administered to treat a human being who is suffering from CRPS, wherein the human being is not a woman who is pregnant or breastfeeding. In some embodiments, neridronic acid is administered to treat a human being who is suffering from CRPS, wherein the human being is a woman of child-bearing potential who has a negative urine Beta-human chorionic gonadotropin (ß-HCG) pregnancy test, and is using 2 forms of medically acceptable contraception, including at least 1 highly effective method of contraception with a low failure rate, defined as less than 1% per year, and a second medically acceptable method, which can be used by her male partner. In some embodiments, neridronic acid is administered to treat a human being who is suffering from CRPS, wherein the human being does not have elevated aspartate aminotransferase (AST) greater than 2-fold that of the upper limit of normal (ULN). In some embodiments, neridronic acid is administered to treat a human being who is suffering from CRPS, wherein the human being does not have or alanine aminotransferase (ALT) greater than 2-fold that of the upper limit of normal (ULN). In some embodiments, neridronic acid is administered to treat a human being who is suffering from CRPS, wherein the human being does not have evidence or history of chronic liver disease.

Unless otherwise indicated, the term "recent" may refer to the last 30 days, 60 days, 90 days, 180 days, 270 days, or one year.

In some embodiments, neridronic acid is administered to treat a human being who is suffering from CRPS and back pain. In some embodiments, neridronic acid is administered to treat a human being who is suffering from CRPS and headache. In some embodiments, neridronic acid is administered to treat a human being who is suffering from CRPS and arthritis. In some embodiments, neridronic acid is administered to treat a human being who is suffering from CRPS and migraine. In some embodiments, neridronic acid is administered to treat a human being who is suffering from CRPS and arthralgia. In some embodiments, neridronic acid is administered to treat a human being who is suffering from CRPS and osteoarthritis. In some embodiments, the method is effective to treat CRPS. In some embodiments, the method is effective to treat back pain, headache, arthritis, migraine, arthralgia, and/or osteoarthritis.

In some embodiments, neridronic acid is administered to treat a human being who is suffering from CRPS and a concomitant psychiatric disorder, such as anxiety, depression (including moderate or severe depression), insomnia, etc. In some embodiments, neridronic acid is administered to treat a human being who is suffering from CRPS and anxiety. In some embodiments, neridronic acid is administered to treat a human being who is suffering from CRPS and depression. In some embodiments, neridronic acid is administered to treat a human being who is suffering from CRPS and moderate depression. In some embodiments, neridronic acid is administered to treat a human being who is suffering from CRPS and insomnia.

In some embodiments, the neridronic acid is administered to a human being who has undergone a recent regular dental examination.

Medication

In some embodiments, neridronic acid is administered to treat a human being who is suffering from CRPS, wherein the human being is not being treated with several concomitant medications/therapies such as high-dose opioids, drugs potentially causing hypocalcemia, bisphosphonates, calcitonin, denosumab, anti-angiogenic drugs, NSAIDS, systemic steroids, etc. In some embodiments, neridronic acid is administered to treat a human being who is suffering from CRPS, wherein the human being is not being treated with high-dose opioids. In some embodiments, neridronic acid is administered to treat a human being who is suffering from CRPS, wherein the human being is not being treated with a drug potentially causing hypocalcemia. In some embodiments, neridronic acid is administered to treat a human being who is suffering from CRPS, wherein the human being is not being treated with another bisphosphonate. In some embodiments, neridronic acid is administered to treat a human being who is suffering from CRPS, wherein the human being is not being treated with calcitonin. In some embodiments, neridronic acid is administered to treat a human being who is suffering from CRPS, wherein the human being is not being treated with denosumab. In some embodiments, neridronic acid is administered to treat a human being who is suffering from CRPS, wherein the human being is not being treated with anti-angiogenic drugs. In some embodiments, neridronic acid is administered to treat a human being who is suffering from CRPS, wherein the human being is not being treated with NSAIDS. In some embodiments, neridronic acid is administered to treat a human being who is suffering from CRPS, wherein the human being is not being treated with systemic steroids. In some embodiments, neridronic acid is administered to treat a human being who is suffering from CRPS, wherein the human being has not been treated with another bisphosphonate within the previous year. In some embodiments, neridronic acid is administered to treat a human being who is suffering from CRPS, wherein the human being is not being treated with denosumab. In some embodiments, neridronic acid is administered to treat a human being who is suffering from CRPS, wherein the human being is not being treated with a bone turnover suppressing drug. In some embodiments, neridronic acid is administered to treat a human being who is suffering from CRPS, wherein the human being does not require treatment with oral or intravenous bisphosphonate for another condition such as osteoporosis during the treatment for CRPS within 6 months. In some embodiments, neridronic acid is administered to treat a human being who is suffering from CRPS, wherein the human being does not require administration of denosumab (Prolia®) or other drugs affecting bone turnover or bone metabolism within 6 months.

In some embodiments, neridronic acid is co-administered with a birth control medication or method to treat a human being who is suffering from CRPS. In some embodiments, neridronic acid is co-administered with vitamin D to treat a human being who is suffering from CRPS.

In some embodiments, neridronic acid may be used to reduce the use of non-steroidal anti-inflammatory drug (NSAIDs), opioids, or other pain medications, for a patient suffering from pain, inflammation, a similar condition, or any condition described herein. For example, use of NSAIDs, opioids, or other pain medications may be reduced by at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, or at least about 90%, up to about 100%, as compared to the use of NSAIDs, opioids or other pain medications without administration of the osteoclast inhibitor. Use of the opioids, NSAIDs, or other pain medications may be reduced by at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, or at least about 90%, up to about 100%, as compared to the use of NSAIDS, opioids, or other pain medications at baseline.

The reduction in the use of NSAIDs, opioids, or other pain medications may be observed at about one week, about two weeks, about three weeks, about one month, about two months, about three months, about four months, about five months, about six months, about seven months, about eight months, about nine months, about 10 months, about 11 months, or about one year or more, after the administration of osteoclast inhibitor.

The effectiveness of the use of neridronic acid to treat CRPS may be affected by gender, age, and/or race. In some embodiments, neridronic acid is administered to treat a female human being who is suffering from CRPS. In some embodiments, neridronic acid is administered to treat a male human being who is suffering from CRPS. In some embodiments, neridronic acid is administered to treat a human being who is suffering from CRPS, Examples of selections of patients receiving neridronic acid are summarized in Tables I-X below, such as a symptom for which CRPS human patient receiving neridronic acid is selected, a precipitating event for which CRPS human patient receiving neridronic acid to treat CRPS is selected, a duration of CRPS when neridronic is first administered for which human patient is selected, and a duration of condition at treatment start for which CRPS human patient receiving neridronic acid is selected.

TABLE I

| Symptom for which CRPS human patient receiving neridronic acid is selected | Precipitating event for which CRPS human patient receiving neridronic acid to treat CRPS is selected |
|---|---|
| hyperesthesia | surgery |
| hyperalgesia | surgery |
| pinprick hyperalgesia | surgery |
| allodynia | surgery |
| temperature asymmetry | surgery |
| skin color asymmetry | surgery |
| sweating asymmetry | surgery |
| asymmetric edema | surgery |
| trophic changes | surgery |
| motor changes | surgery |
| edema | surgery |
| dystrophic changes | surgery |
| skin changes | surgery |
| nail changes | surgery |
| hair changes | surgery |
| motor abnormalities | surgery |
| hyperesthesia | fracture |
| hyperalgesia | fracture |
| pinprick hyperalgesia | fracture |
| allodynia | fracture |
| temperature asymmetry | fracture |
| skin color asymmetry | fracture |
| sweating asymmetry | fracture |
| asymmetric edema | fracture |
| trophic changes | fracture |
| motor changes | fracture |
| edema | fracture |
| dystrophic changes | fracture |
| skin changes | fracture |
| nail changes | fracture |
| hair changes | fracture |
| motor abnormalities | fracture |
| hyperesthesia | sprain |
| hyperalgesia | sprain |

TABLE I-continued

| Symptom for which CRPS human patient receiving neridronic acid is selected | Precipitating event for which CRPS human patient receiving neridronic acid to treat CRPS is selected |
|---|---|
| pinprick hyperalgesia | sprain |
| allodynia | sprain |
| temperature asymmetry | sprain |
| skin color asymmetry | sprain |
| sweating asymmetry | sprain |
| asymmetric edema | sprain |
| trophic changes | sprain |
| motor changes | sprain |
| edema | sprain |
| dystrophic changes | sprain |
| skin changes | sprain |
| nail changes | sprain |
| hair changes | sprain |
| motor abnormalities | sprain |
| hyperesthesia | crush |
| hyperalgesia | crush |
| pinprick hyperalgesia | crush |
| allodynia | crush |
| temperature asymmetry | crush |
| skin color asymmetry | crush |
| sweating asymmetry | crush |
| asymmetric edema | crush |
| trophic changes | crush |
| motor changes | crush |
| edema | crush |
| dystrophic changes | crush |
| skin changes | crush |
| nail changes | crush |
| hair changes | crush |
| motor abnormalities | crush |
| hyperesthesia | contusion |
| hyperalgesia | contusion |
| Pinprick hyperalgesia | contusion |
| allodynia | contusion |
| temperature asymmetry | contusion |
| skin color asymmetry | contusion |
| sweating asymmetry | contusion |
| asymmetric edema | contusion |
| trophic changes | contusion |
| motor changes | contusion |
| edema | contusion |
| dystrophic changes | contusion |
| skin changes | contusion |
| nail changes | contusion |
| hair changes | contusion |
| motor abnormalities | contusion |
| hyperesthesia | dislocation |
| hyperalgesia | dislocation |
| pinprick hyperalgesia | dislocation |
| allodynia | dislocation |
| temperature asymmetry | dislocation |
| skin color asymmetry | dislocation |
| sweating asymmetry | dislocation |
| asymmetric edema | dislocation |
| trophic changes | dislocation |
| motor changes | dislocation |
| edema | dislocation |
| dystrophic changes | dislocation |
| skin changes | dislocation |
| nail changes | dislocation |
| hair changes | dislocation |
| motor abnormalities | dislocation |
| hyperesthesia | scratch |
| hyperalgesia | scratch |
| pinprick hyperalgesia | scratch |
| allodynia | scratch |
| temperature asymmetry | scratch |
| skin color asymmetry | scratch |
| sweating asymmetry | scratch |
| asymmetric edema | scratch |
| trophic changes | scratch |
| motor changes | scratch |
| edema | scratch |
| dystrophic changes | scratch |
| skin changes | scratch |
| nail changes | scratch |
| hair changes | scratch |
| motor abnormalities | scratch |
| hyperesthesia | skin puncture |
| hyperalgesia | skin puncture |
| pinprick hyperalgesia | skin puncture |
| allodynia | skin puncture |
| temperature asymmetry | skin puncture |
| skin color asymmetry | skin puncture |
| sweating asymmetry | skin puncture |
| asymmetric edema | skin puncture |
| trophic changes | skin puncture |
| motor changes | skin puncture |
| edema | skin puncture |
| dystrophic changes | skin puncture |
| skin changes | skin puncture |
| nail changes | skin puncture |
| hair changes | skin puncture |
| motor abnormalities | skin puncture |

TABLE II

| Duration of CRPS when neridronic is first administered for which human patient is selected | Precipitating event for which human patient receiving neridronic acid to treat CRPS is selected |
|---|---|
| 0-3 months | surgery |
| 0-3 months | fracture |
| 0-3 months | sprain |
| 0-3 months | crush |
| 0-3 months | contusion |
| 0-3 months | dislocation |
| 0-3 months | scratch |
| 0-3 months | skin puncture |
| 3-6 months | surgery |
| 3-6 months | fracture |
| 3-6 months | sprain |
| 3-6 months | crush |
| 3-6 months | contusion |
| 3-6 months | dislocation |
| 3-6 months | scratch |
| 3-6 months | skin puncture |
| 6-9 months | surgery |
| 6-9 months | fracture |
| 6-9 months | sprain |
| 6-9 months | crush |
| 6-9 months | contusion |
| 6-9 months | dislocation |
| 6-9 months | scratch |
| 6-9 months | skin puncture |
| 9-12 months | surgery |
| 9-12 months | fracture |
| 9-12 months | sprain |
| 9-12 months | crush |
| 9-12 months | contusion |
| 9-12 months | dislocation |
| 9-12 months | scratch |
| 9-12 months | skin puncture |
| 1-2 years | surgery |
| 1-2 years | fracture |
| 1-2 years | sprain |
| 1-2 years | crush |
| 1-2 years | contusion |
| 1-2 years | dislocation |
| 1-2 years | scratch |
| 1-2 years | skin puncture |
| 2-4 years | surgery |
| 2-4 years | fracture |
| 2-4 years | sprain |
| 2-4 years | crush |
| 2-4 years | contusion |

TABLE II-continued

| Duration of CRPS when neridronic is first administered for which human patient is selected | Precipitating event for which human patient receiving neridronic acid to treat CRPS is selected |
|---|---|
| 2-4 years | dislocation |
| 2-4 years | scratch |
| 2-4 years | skin puncture |
| 4-6 years | surgery |
| 4-6 years | fracture |
| 4-6 years | sprain |
| 4-6 years | crush |
| 4-6 years | contusion |
| 4-6 years | dislocation |
| 4-6 years | scratch |
| 4-6 years | skin puncture |
| 6-8 years | surgery |
| 6-8 years | fracture |
| 6-8 years | sprain |
| 6-8 years | crush |
| 6-8 years | contusion |
| 6-8 years | dislocation |
| 6-8 years | scratch |
| 6-8 years | skin puncture |
| 8-10 years | surgery |
| 8-10 years | fracture |
| 8-10 years | sprain |
| 8-10 years | crush |
| 8-10 years | contusion |
| 8-10 years | dislocation |
| 8-10 years | scratch |
| 8-10 years | skin puncture |
| 6-10 years | surgery |
| 6-10 years | fracture |
| 6-10 years | sprain |
| 6-10 years | crush |
| 6-10 years | contusion |
| 6-10 years | dislocation |
| 6-10 years | scratch |
| less than 2 years | skin puncture |
| less than 2 years | surgery |
| less than 2 years | fracture |
| less than 2 years | sprain |
| less than 2 years | crush |
| less than 2 years | contusion |
| less than 2 years | dislocation |
| less than 2 years | scratch |
| less than 2 years | skin puncture |
| more than 2 years | surgery |
| more than 2 years | fracture |
| more than 2 years | sprain |
| more than 2 years | crush |
| more than 2 years | contusion |
| more than 2 years | dislocation |
| more than 2 years | scratch |
| more than 2 years | skin puncture |

TABLE III

| Symptom for which CRPS human patient receiving neridronic acid is selected | Pain level (NRS) at start of treatment |
|---|---|
| hyperesthesia | at least 4 |
| hyperalgesia | at least 4 |
| pinprick hyperalgesia | at least 4 |
| allodynia | at least 4 |
| temperature asymmetry | at least 4 |
| skin color asymmetry | at least 4 |
| sweating asymmetry | at least 4 |
| asymmetric edema | at least 4 |
| trophic changes | at least 4 |
| motor changes | at least 4 |
| edema | at least 4 |
| dystrophic changes | at least 4 |
| skin changes | at least 4 |
| nail changes | at least 4 |
| hair changes | at least 4 |
| motor abnormalities | at least 4 |
| hyperesthesia | at least 5 |
| hyperalgesia | at least 5 |
| pinprick hyperalgesia | at least 5 |
| allodynia | at least 5 |
| temperature asymmetry | at least 5 |
| skin color asymmetry | at least 5 |
| sweating asymmetry | at least 5 |
| asymmetric edema | at least 5 |
| trophic changes | at least 5 |
| motor changes | at least 5 |
| edema | at least 5 |
| dystrophic changes | at least 5 |
| skin changes | at least 5 |
| nail changes | at least 5 |
| hair changes | at least 5 |
| motor abnormalities | at least 5 |
| hyperesthesia | at least 6 |
| hyperalgesia | at least 6 |
| pinprick hyperalgesia | at least 6 |
| allodynia | at least 6 |
| temperature asymmetry | at least 6 |
| skin color asymmetry | at least 6 |
| sweating asymmetry | at least 6 |
| asymmetric edema | at least 6 |
| trophic changes | at least 6 |
| motor changes | at least 6 |
| edema | at least 6 |
| dystrophic changes | at least 6 |
| skin changes | at least 6 |
| nail changes | at least 6 |
| hair changes | at least 6 |
| motor abnormalities | at least 6 |
| hyperesthesia | at least 7 |
| hyperalgesia | at least 7 |
| pinprick hyperalgesia | at least 7 |
| allodynia | at least 7 |
| temperature asymmetry | at least 7 |
| skin color asymmetry | at least 7 |
| sweating asymmetry | at least 7 |
| asymmetric edema | at least 7 |
| trophic changes | at least 7 |
| motor changes | at least 7 |
| edema | at least 7 |
| dystrophic changes | at least 7 |
| skin changes | at least 7 |
| nail changes | at least 7 |
| hair changes | at least 7 |
| motor abnormalities | at least 7 |
| hyperesthesia | at least 8 |
| hyperalgesia | at least 8 |
| pinprick hyperalgesia | at least 8 |
| allodynia | at least 8 |
| temperature asymmetry | at least 8 |
| skin color asymmetry | at least 8 |
| sweating asymmetry | at least 8 |
| asymmetric edema | at least 8 |
| trophic changes | at least 8 |
| motor changes | at least 8 |
| edema | at least 8 |
| dystrophic changes | at least 8 |
| skin changes | at least 8 |
| nail changes | at least 8 |
| hair changes | at least 8 |
| motor abnormalities | at least 8 |
| hyperesthesia | at least 9 |
| hyperalgesia | at least 9 |
| pinprick hyperalgesia | at least 9 |
| allodynia | at least 9 |
| temperature asymmetry | at least 9 |
| skin color asymmetry | at least 9 |
| sweating asymmetry | at least 9 |
| asymmetric edema | at least 9 |
| trophic changes | at least 9 |
| motor changes | at least 9 |

TABLE III-continued

| Symptom for which CRPS human patient receiving neridronic acid is selected | Pain level (NRS) at start of treatment |
|---|---|
| edema | at least 9 |
| dystrophic changes | at least 9 |
| skin changes | at least 9 |
| nail changes | at least 9 |
| hair changes | at least 9 |
| motor abnormalities | at least 9 |
| hyperesthesia | 4-5 |
| hyperalgesia | 4-5 |
| pinprick hyperalgesia | 4-5 |
| allodynia | 4-5 |
| temperature asymmetry | 4-5 |
| skin color asymmetry | 4-5 |
| sweating asymmetry | 4-5 |
| asymmetric edema | 4-5 |
| trophic changes | 4-5 |
| motor changes | 4-5 |
| edema | 4-5 |
| dystrophic changes | 4-5 |
| skin changes | 4-5 |
| nail changes | 4-5 |
| hair changes | 4-5 |
| motor abnormalities | 4-5 |
| hyperesthesia | 5-6 |
| hyperalgesia | 5-6 |
| pinprick hyperalgesia | 5-6 |
| allodynia | 5-6 |
| temperature asymmetry | 5-6 |
| skin color asymmetry | 5-6 |
| sweating asymmetry | 5-6 |
| asymmetric edema | 5-6 |
| trophic changes | 5-6 |
| motor changes | 5-6 |
| edema | 5-6 |
| dystrophic changes | 5-6 |
| skin changes | 5-6 |
| nail changes | 5-6 |
| hair changes | 5-6 |
| motor abnormalities | 5-6 |
| hyperesthesia | 6-7 |
| hyperalgesia | 6-7 |
| pinprick hyperalgesia | 6-7 |
| allodynia | 6-7 |
| temperature asymmetry | 6-7 |
| skin color asymmetry | 6-7 |
| sweating asymmetry | 6-7 |
| asymmetric edema | 6-7 |
| trophic changes | 6-7 |
| motor changes | 6-7 |
| edema | 6-7 |
| dystrophic changes | 6-7 |
| skin changes | 6-7 |
| nail changes | 6-7 |
| hair changes | 6-7 |
| motor abnormalities | 6-7 |
| hyperesthesia | 7-8 |
| hyperalgesia | 7-8 |
| pinprick hyperalgesia | 7-8 |
| allodynia | 7-8 |
| temperature asymmetry | 7-8 |
| skin color asymmetry | 7-8 |
| sweating asymmetry | 7-8 |
| asymmetric edema | 7-8 |
| trophic changes | 7-8 |
| motor changes | 7-8 |
| edema | 7-8 |
| dystrophic changes | 7-8 |
| skin changes | 7-8 |
| nail changes | 7-8 |
| hair changes | 7-8 |
| motor abnormalities | 7-8 |
| hyperesthesia | 8-9 |
| hyperalgesia | 8-9 |
| pinprick hyperalgesia | 8-9 |
| allodynia | 8-9 |
| temperature asymmetry | 8-9 |
| skin color asymmetry | 8-9 |
| sweating asymmetry | 8-9 |
| asymmetric edema | 8-9 |
| trophic changes | 8-9 |
| motor changes | 8-9 |
| edema | 8-9 |
| dystrophic changes | 8-9 |
| skin changes | 8-9 |
| nail changes | 8-9 |
| hair changes | 8-9 |
| motor abnormalities | 8-9 |
| hyperesthesia | 9-10 |
| hyperalgesia | 9-10 |
| pinprick hyperalgesia | 9-10 |
| allodynia | 9-10 |
| temperature asymmetry | 9-10 |
| skin color asymmetry | 9-10 |
| sweating asymmetry | 9-10 |
| asymmetric edema | 9-10 |
| trophic changes | 9-10 |
| motor changes | 9-10 |
| edema | 9-10 |
| dystrophic changes | 9-10 |
| skin changes | 9-10 |
| nail changes | 9-10 |
| hair changes | 9-10 |
| motor abnormalities | 9-10 |
| hyperesthesia | 4-6 |
| hyperalgesia | 4-6 |
| pinprick hyperalgesia | 4-6 |
| allodynia | 4-6 |
| temperature asymmetry | 4-6 |
| skin color asymmetry | 4-6 |
| sweating asymmetry | 4-6 |
| asymmetric edema | 4-6 |
| trophic changes | 4-6 |
| motor changes | 4-6 |
| edema | 4-6 |
| dystrophic changes | 4-6 |
| skin changes | 4-6 |
| nail changes | 4-6 |
| hair changes | 4-6 |
| motor abnormalities | 4-6 |
| hyperesthesia | 6-8 |
| hyperalgesia | 6-8 |
| pinprick hyperalgesia | 6-8 |
| allodynia | 6-8 |
| temperature asymmetry | 6-8 |
| skin color asymmetry | 6-8 |
| sweating asymmetry | 6-8 |
| asymmetric edema | 6-8 |
| trophic changes | 6-8 |
| motor changes | 6-8 |
| edema | 6-8 |
| dystrophic changes | 6-8 |
| skin changes | 6-8 |
| nail changes | 6-8 |
| hair changes | 6-8 |
| motor abnormalities | 6-8 |
| hyperesthesia | 8-10 |
| hyperalgesia | 8-10 |
| pinprick hyperalgesia | 8-10 |
| allodynia | 8-10 |
| temperature asymmetry | 8-10 |
| skin color asymmetry | 8-10 |
| sweating asymmetry | 8-10 |
| asymmetric edema | 8-10 |
| trophic changes | 8-10 |
| motor changes | 8-10 |
| edema | 8-10 |
| dystrophic changes | 8-10 |
| skin changes | 8-10 |
| nail changes | 8-10 |
| hair changes | 8-10 |
| motor abnormalities | 8-10 |

TABLE IV

| Limb affected by CRPS | Pain level (NRS) at start of treatment |
|---|---|
| hand | at least 4 |
| hand | at least 5 |
| hand | at least 6 |
| hand | at least 7 |
| hand | at least 8 |
| hand | at least 9 |
| hand | 4-5 |
| hand | 5-6 |
| hand | 6-7 |
| hand | 7-8 |
| hand | 8-9 |
| hand | 9-10 |
| hand | 4-6 |
| hand | 6-8 |
| hand | 8-10 |
| arm | at least 4 |
| arm | at least 5 |
| arm | at least 6 |
| arm | at least 7 |
| arm | at least 8 |
| arm | at least 9 |
| arm | 4-5 |
| arm | 5-6 |
| arm | 6-7 |
| arm | 7-8 |
| arm | 8-9 |
| arm | 9-10 |
| arm | 4-6 |
| arm | 6-8 |
| arm | 8-10 |
| lower arm | at least 4 |
| lower arm | at least 5 |
| lower arm | at least 6 |
| lower arm | at least 7 |
| lower arm | at least 8 |
| lower arm | at least 9 |
| lower arm | 4-5 |
| lower arm | 5-6 |
| lower arm | 6-7 |
| lower arm | 7-8 |
| lower arm | 8-9 |
| lower arm | 9-10 |
| lower arm | 4-6 |
| lower arm | 6-8 |
| lower arm | 8-10 |
| upper arm | at least 4 |
| upper arm | at least 5 |
| upper arm | at least 6 |
| upper arm | at least 7 |
| upper arm | at least 8 |
| upper arm | at least 9 |
| upper arm | 4-5 |
| upper arm | 5-6 |
| upper arm | 6-7 |
| upper arm | 7-8 |
| upper arm | 8-9 |
| upper arm | 9-10 |
| upper arm | 4-6 |
| upper arm | 6-8 |
| upper arm | 8-10 |
| foot | at least 4 |
| foot | at least 5 |
| foot | at least 6 |
| foot | at least 7 |
| foot | at least 8 |
| foot | at least 9 |
| foot | 4-5 |
| foot | 5-6 |
| foot | 6-7 |
| foot | 7-8 |
| foot | 8-9 |
| foot | 9-10 |
| foot | 4-6 |
| foot | 6-8 |
| foot | 8-10 |
| leg | at least 4 |
| leg | at least 5 |
| leg | at least 6 |
| leg | at least 7 |
| leg | at least 8 |
| leg | at least 9 |
| leg | 4-5 |
| leg | 5-6 |
| leg | 6-7 |
| leg | 7-8 |
| leg | 8-9 |
| leg | 9-10 |
| leg | 4-6 |
| leg | 6-8 |
| leg | 8-10 |
| lower leg | at least 4 |
| lower leg | at least 5 |
| lower leg | at least 6 |
| lower leg | at least 7 |
| lower leg | at least 8 |
| lower leg | at least 9 |
| lower leg | 4-5 |
| lower leg | 5-6 |
| lower leg | 6-7 |
| lower leg | 7-8 |
| lower leg | 8-9 |
| lower leg | 9-10 |
| lower leg | 4-6 |
| lower leg | 6-8 |
| lower leg | 8-10 |
| upper leg | at least 4 |
| upper leg | at least 5 |
| upper leg | at least 6 |
| upper leg | at least 7 |
| upper leg | at least 8 |
| upper leg | at least 9 |
| upper leg | 4-5 |
| upper leg | 5-6 |
| upper leg | 6-7 |
| upper leg | 7-8 |
| upper leg | 8-9 |
| upper leg | 9-10 |
| upper leg | 4-6 |
| upper leg | 6-8 |
| upper leg | 8-10 |

TABLE V

| Duration of CRPS when neridronic is first administered for which human patient is selected | Pain level (NRS) at start of treatment |
|---|---|
| 0-3 months | at least 4 |
| 0-3 months | at least 5 |
| 0-3 months | at least 6 |
| 0-3 months | at least 7 |
| 0-3 months | at least 8 |
| 0-3 months | at least 9 |
| 0-3 months | 4-5 |
| 0-3 months | 5-6 |
| 0-3 months | 6-7 |
| 0-3 months | 7-8 |
| 0-3 months | 8-9 |
| 0-3 months | 9-10 |
| 0-3 months | 4-6 |
| 0-3 months | 6-8 |
| 0-3 months | 8-10 |
| 3-6 months | at least 4 |
| 3-6 months | at least 5 |
| 3-6 months | at least 6 |
| 3-6 months | at least 7 |
| 3-6 months | at least 8 |
| 3-6 months | at least 9 |
| 3-6 months | 4-5 |
| 3-6 months | 5-6 |
| 3-6 months | 6-7 |
| 3-6 months | 7-8 |

TABLE V-continued

| Duration of CRPS when neridronic is first administered for which human patient is selected | Pain level (NRS) at start of treatment |
|---|---|
| 3-6 months | 8-9 |
| 3-6 months | 9-10 |
| 3-6 months | 4-6 |
| 3-6 months | 6-8 |
| 3-6 months | 8-10 |
| 6-9 months | at least 4 |
| 6-9 months | at least 5 |
| 6-9 months | at least 6 |
| 6-9 months | at least 7 |
| 6-9 months | at least 8 |
| 6-9 months | at least 9 |
| 6-9 months | 4-5 |
| 6-9 months | 5-6 |
| 6-9 months | 6-7 |
| 6-9 months | 7-8 |
| 6-9 months | 8-9 |
| 6-9 months | 9-10 |
| 6-9 months | 4-6 |
| 6-9 months | 6-8 |
| 6-9 months | 8-10 |
| 9-12 months | at least 4 |
| 9-12 months | at least 5 |
| 9-12 months | at least 6 |
| 9-12 months | at least 7 |
| 9-12 months | at least 8 |
| 9-12 months | at least 9 |
| 9-12 months | 4-5 |
| 9-12 months | 5-6 |
| 9-12 months | 6-7 |
| 9-12 months | 7-8 |
| 9-12 months | 8-9 |
| 9-12 months | 9-10 |
| 9-12 months | 4-6 |
| 9-12 months | 6-8 |
| 9-12 months | 8-10 |
| 1-2 years | at least 4 |
| 1-2 years | at least 5 |
| 1-2 years | at least 6 |
| 1-2 years | at least 7 |
| 1-2 years | at least 8 |
| 1-2 years | at least 9 |
| 1-2 years | 4-5 |
| 1-2 years | 5-6 |
| 1-2 years | 6-7 |
| 1-2 years | 7-8 |
| 1-2 years | 8-9 |
| 1-2 years | 9-10 |
| 1-2 years | 4-6 |
| 1-2 years | 6-8 |
| 1-2 years | 8-10 |
| 2-4 years | at least 4 |
| 2-4 years | at least 5 |
| 2-4 years | at least 6 |
| 2-4 years | at least 7 |
| 2-4 years | at least 8 |
| 2-4 years | at least 9 |
| 2-4 years | 4-5 |
| 2-4 years | 5-6 |
| 2-4 years | 6-7 |
| 2-4 years | 7-8 |
| 2-4 years | 8-9 |
| 2-4 years | 9-10 |
| 2-4 years | 4-6 |
| 2-4 years | 6-8 |
| 2-4 years | 8-10 |
| 4-6 years | at least 4 |
| 4-6 years | at least 5 |
| 4-6 years | at least 6 |
| 4-6 years | at least 7 |
| 4-6 years | at least 8 |
| 4-6 years | at least 9 |
| 4-6 years | 4-5 |
| 4-6 years | 5-6 |
| 4-6 years | 6-7 |
| 4-6 years | 7-8 |
| 4-6 years | 8-9 |
| 4-6 years | 9-10 |
| 4-6 years | 4-6 |
| 4-6 years | 6-8 |
| 4-6 years | 8-10 |
| 6-10 years | at least 4 |
| 6-10 years | at least 5 |
| 6-10 years | at least 6 |
| 6-10 years | at least 7 |
| 6-10 years | at least 8 |
| 6-10 years | at least 9 |
| 6-10 years | 4-5 |
| 6-10 years | 5-6 |
| 6-10 years | 6-7 |
| 6-10 years | 7-8 |
| 6-10 years | 8-9 |
| 6-10 years | 9-10 |
| 6-10 years | 4-6 |
| 6-10 years | 6-8 |
| 6-10 years | 8-10 |
| less than 2 years | at least 4 |
| less than 2 years | at least 5 |
| less than 2 years | at least 6 |
| less than 2 years | at least 7 |
| less than 2 years | at least 8 |
| less than 2 years | at least 9 |
| less than 2 years | 4-5 |
| less than 2 years | 5-6 |
| less than 2 years | 6-7 |
| less than 2 years | 7-8 |
| less than 2 years | 8-9 |
| less than 2 years | 9-10 |
| less than 2 years | 4-6 |
| less than 2 years | 6-8 |
| less than 2 years | 8-10 |
| more than 2 years | at least 4 |
| more than 2 years | at least 5 |
| more than 2 years | at least 6 |
| more than 2 years | at least 7 |
| more than 2 years | at least 8 |
| more than 2 years | at least 9 |
| more than 2 years | 4-5 |
| more than 2 years | 5-6 |
| more than 2 years | 6-7 |
| more than 2 years | 7-8 |
| more than 2 years | 8-9 |
| more than 2 years | 9-10 |
| more than 2 years | 4-6 |
| more than 2 years | 6-8 |
| more than 2 years | 8-10 |

TABLE VI

| Precipitating event for which human patient receiving neridronic acid to treat CRPS is selected | Pain level (NRS) at start of treatment |
|---|---|
| surgery | at least 4 |
| surgery | at least 5 |
| surgery | at least 6 |
| surgery | at least 7 |
| surgery | at least 8 |
| surgery | at least 9 |
| surgery | 4-5 |
| surgery | 5-6 |
| surgery | 6-7 |
| surgery | 7-8 |
| surgery | 8-9 |
| surgery | 9-10 |
| surgery | 4-6 |
| surgery | 6-8 |
| surgery | 8-10 |
| fracture | at least 4 |
| fracture | at least 5 |
| fracture | at least 6 |
| fracture | at least 7 |

TABLE VI-continued

| Precipitating event for which human patient receiving neridronic acid to treat CRPS is selected | Pain level (NRS) at start of treatment |
|---|---|
| fracture | at least 8 |
| fracture | at least 9 |
| fracture | 4-5 |
| fracture | 5-6 |
| fracture | 6-7 |
| fracture | 7-8 |
| fracture | 8-9 |
| fracture | 9-10 |
| fracture | 4-6 |
| fracture | 6-8 |
| fracture | 8-10 |
| sprain | at least 4 |
| sprain | at least 5 |
| sprain | at least 6 |
| sprain | at least 7 |
| sprain | at least 8 |
| sprain | at least 9 |
| sprain | 4-5 |
| sprain | 5-6 |
| sprain | 6-7 |
| sprain | 7-8 |
| sprain | 8-9 |
| sprain | 9-10 |
| sprain | 4-6 |
| sprain | 6-8 |
| sprain | 8-10 |
| crush | at least 4 |
| crush | at least 5 |
| crush | at least 6 |
| crush | at least 7 |
| crush | at least 8 |
| crush | at least 9 |
| crush | 4-5 |
| crush | 5-6 |
| crush | 6-7 |
| crush | 7-8 |
| crush | 8-9 |
| crush | 9-10 |
| crush | 4-6 |
| crush | 6-8 |
| crush | 8-10 |
| contusion | at least 4 |
| contusion | at least 5 |
| contusion | at least 6 |
| contusion | at least 7 |
| contusion | at least 8 |
| contusion | at least 9 |
| contusion | 4-5 |
| contusion | 5-6 |
| contusion | 6-7 |
| contusion | 7-8 |
| contusion | 8-9 |
| contusion | 9-10 |
| contusion | 4-6 |
| contusion | 6-8 |
| contusion | 8-10 |
| dislocation | at least 4 |
| dislocation | at least 5 |
| dislocation | at least 6 |
| dislocation | at least 7 |
| dislocation | at least 8 |
| dislocation | at least 9 |
| dislocation | 4-5 |
| dislocation | 5-6 |
| dislocation | 6-7 |
| dislocation | 7-8 |
| dislocation | 8-9 |
| dislocation | 9-10 |
| dislocation | 4-6 |
| dislocation | 6-8 |
| dislocation | 8-10 |
| scratch | at least 4 |
| scratch | at least 5 |
| scratch | at least 6 |
| scratch | at least 7 |
| scratch | at least 8 |
| scratch | at least 9 |
| scratch | 4-5 |
| scratch | 5-6 |
| scratch | 6-7 |
| scratch | 7-8 |
| scratch | 8-9 |
| scratch | 9-10 |
| scratch | 4-6 |
| scratch | 6-8 |
| scratch | 8-10 |
| skin puncture | at least 4 |
| skin puncture | at least 5 |
| skin puncture | at least 6 |
| skin puncture | at least 7 |
| skin puncture | at least 8 |
| skin puncture | at least 9 |
| skin puncture | 4-5 |
| skin puncture | 5-6 |
| skin puncture | 6-7 |
| skin puncture | 7-8 |
| skin puncture | 8-9 |
| skin puncture | 9-10 |
| skin puncture | 4-6 |
| skin puncture | 6-8 |
| skin puncture | 8-10 |

TABLE VII

| Comorbidities suffered by CRPS patient being treated | Pain level (NRS) at start of treatment |
|---|---|
| back pain | at least 4 |
| back pain | at least 5 |
| back pain | at least 6 |
| back pain | at least 7 |
| back pain | at least 8 |
| back pain | at least 9 |
| back pain | 4-5 |
| back pain | 5-6 |
| back pain | 6-7 |
| back pain | 7-8 |
| back pain | 8-9 |
| back pain | 9-10 |
| back pain | 4-6 |
| back pain | 6-8 |
| back pain | 8-10 |
| headache | at least 4 |
| headache | at least 5 |
| headache | at least 6 |
| headache | at least 7 |
| headache | at least 8 |
| headache | at least 9 |
| headache | 4-5 |
| headache | 5-6 |
| headache | 6-7 |
| headache | 7-8 |
| headache | 8-9 |
| headache | 9-10 |
| headache | 4-6 |
| headache | 6-8 |
| headache | 8-10 |
| arthritis | at least 4 |
| arthritis | at least 5 |
| arthritis | at least 6 |
| arthritis | at least 7 |
| arthritis | at least 8 |
| arthritis | at least 9 |
| arthritis | 4-5 |
| arthritis | 5-6 |
| arthritis | 6-7 |
| arthritis | 7-8 |
| arthritis | 8-9 |
| arthritis | 9-10 |

TABLE VII-continued

| Comorbidities suffered by CRPS patient being treated | Pain level (NRS) at start of treatment |
|---|---|
| arthritis | 4-6 |
| arthritis | 6-8 |
| arthritis | 8-10 |
| migraine | at least 4 |
| migraine | at least 5 |
| migraine | at least 6 |
| migraine | at least 7 |
| migraine | at least 8 |
| migraine | at least 9 |
| migraine | 4-5 |
| migraine | 5-6 |
| migraine | 6-7 |
| migraine | 7-8 |
| migraine | 8-9 |
| migraine | 9-10 |
| migraine | 4-6 |
| migraine | 6-8 |
| migraine | 8-10 |
| arthralgia | at least 4 |
| arthralgia | at least 5 |
| arthralgia | at least 6 |
| arthralgia | at least 7 |
| arthralgia | at least 8 |
| arthralgia | at least 9 |
| arthralgia | 4-5 |
| arthralgia | 5-6 |
| arthralgia | 6-7 |
| arthralgia | 7-8 |
| arthralgia | 8-9 |
| arthralgia | 9-10 |
| arthralgia | 4-6 |
| arthralgia | 6-8 |
| arthralgia | 8-10 |
| osteoarthritis | at least 4 |
| osteoarthritis | at least 5 |
| osteoarthritis | at least 6 |
| osteoarthritis | at least 7 |
| osteoarthritis | at least 8 |
| osteoarthritis | at least 9 |
| osteoarthritis | 4-5 |
| osteoarthritis | 5-6 |
| osteoarthritis | 6-7 |
| osteoarthritis | 7-8 |
| osteoarthritis | 8-9 |
| osteoarthritis | 9-10 |
| osteoarthritis | 4-6 |
| osteoarthritis | 6-8 |
| osteoarthritis | 8-10 |

TABLE VIII

| Symptom for which CRPS human patient receiving neridronic acid is selected | Duration of CRPS at Treatment Start for which CRPS human patient receiving neridronic acid is selected |
|---|---|
| hyperesthesia | 0-3 months |
| hyperalgesia | 0-3 months |
| Disproportionate pain | 0-3 months |
| allodynia | 0-3 months |
| temperature asymmetry | 0-3 months |
| skin color asymmetry | 0-3 months |
| sweating asymmetry | 0-3 months |
| asymmetric edema | 0-3 months |
| trophic changes | 0-3 months |
| motor changes | 0-3 months |
| edema | 0-3 months |
| dystrophic changes | 0-3 months |
| skin changes | 0-3 months |
| nail changes | 0-3 months |
| hair changes | 0-3 months |
| motor abnormalities | 0-3 months |
| prinpick hyperalgesia | 0-3 months |
| hyperesthesia | 3-6 months |
| hyperalgesia | 3-6 months |
| Disproportionate pain | 3-6 months |
| allodynia | 3-6 months |
| temperature asymmetry | 3-6 months |
| skin color asymmetry | 3-6 months |
| sweating asymmetry | 3-6 months |
| asymmetric edema | 3-6 months |
| trophic changes | 3-6 months |
| motor changes | 3-6 months |
| edema | 3-6 months |
| dystrophic changes | 3-6 months |
| skin changes | 3-6 months |
| nail changes | 3-6 months |
| hair changes | 3-6 months |
| motor abnormalities | 3-6 months |
| pinprick hyperalgesia | 3-6 months |
| hyperesthesia | 6-9 months |
| hyperalgesia | 6-9 months |
| Disproportionate pain | 6-9 months |
| allodynia | 6-9 months |
| temperature asymmetry | 6-9 months |
| skin color asymmetry | 6-9 months |
| sweating asymmetry | 6-9 months |
| asymmetric edema | 6-9 months |
| trophic changes | 6-9 months |
| motor changes | 6-9 months |
| edema | 6-9 months |
| dystrophic changes | 6-9 months |
| skin changes | 6-9 months |
| nail changes | 6-9 months |
| hair changes | 6-9 months |
| motor abnormalities | 6-9 months |
| pinprick hyperalgesia | 6-9 months |
| hyperesthesia | 9-12 months |
| hyperalgesia | 9-12 months |
| Disproportionate pain | 9-12 months |
| allodynia | 9-12 months |
| temperature asymmetry | 9-12 months |
| skin color asymmetry | 9-12 months |
| sweating asymmetry | 9-12 months |
| asymmetric edema | 9-12 months |
| trophic changes | 9-12 months |
| motor changes | 9-12 months |
| edema | 9-12 months |
| dystrophic changes | 9-12 months |
| skin changes | 9-12 months |
| nail changes | 9-12 months |
| hair changes | 9-12 months |
| motor abnormalities | 9-12 months |
| pinprick hyperalgesia | 9-12 months |
| hyperesthesia | 1-2 years |
| hyperalgesia | 1-2 years |
| allodynia | 1-2 years |
| Disproportionate pain | 1-2 years |
| temperature asymmetry | 1-2 years |
| skin color asymmetry | 1-2 years |
| sweating asymmetry | 1-2 years |
| asymmetric edema | 1-2 years |
| trophic changes | 1-2 years |
| motor changes | 1-2 years |
| edema | 1-2 years |
| dystrophic changes | 1-2 years |
| skin changes | 1-2 years |
| nail changes | 1-2 years |
| hair changes | 1-2 years |
| motor abnormalities | 1-2 years |
| pinprick hyperalgesia | 1-2 years |
| hyperesthesia | 2-4 years |
| hyperalgesia | 2-4 years |
| Disproportionate pain | 2-4 years |
| allodynia | 2-4 years |
| temperature asymmetry | 2-4 years |
| skin color asymmetry | 2-4 years |
| sweating asymmetry | 2-4 years |
| asymmetric edema | 2-4 years |

TABLE VIII-continued

| Symptom for which CRPS human patient receiving neridronic acid is selected | Duration of CRPS at Treatment Start for which CRPS human patient receiving neridronic acid is selected |
|---|---|
| trophic changes | 2-4 years |
| motor changes | 2-4 years |
| edema | 2-4 years |
| dystrophic changes | 2-4 years |
| skin changes | 2-4 years |
| nail changes | 2-4 years |
| hair changes | 2-4 years |
| motor abnormalities | 2-4 years |
| pinprick hyperalgesia | 2-4 years |
| hyperesthesia | 4-6 years |
| hyperalgesia | 4-6 years |
| Disproportionate pain | 4-6 years |
| allodynia | 4-6 years |
| temperature asymmetry | 4-6 years |
| skin color asymmetry | 4-6 years |
| sweating asymmetry | 4-6 years |
| asymmetric edema | 4-6 years |
| trophic changes | 4-6 years |
| motor changes | 4-6 years |
| edema | 4-6 years |
| dystrophic changes | 4-6 years |
| skin changes | 4-6 years |
| nail changes | 4-6 years |
| hair changes | 4-6 years |
| motor abnormalities | 4-6 years |
| pinprick hyperalgesia | 4-6 years |
| hyperesthesia | 6-8 years |
| hyperalgesia | 6-8 years |
| Disproportionate pain | 6-8 years |
| allodynia | 6-8 years |
| temperature asymmetry | 6-8 years |
| skin color asymmetry | 6-8 years |
| sweating asymmetry | 6-8 years |
| asymmetric edema | 6-8 years |
| trophic changes | 6-8 years |
| motor changes | 6-8 years |
| edema | 6-8 years |
| dystrophic changes | 6-8 years |
| skin changes | 6-8 years |
| nail changes | 6-8 years |
| hair changes | 6-8 years |
| motor abnormalities | 6-8 years |
| pinprick hyperalgesia | 6-8 years |
| hyperesthesia | 8-10 years |
| hyperalgesia | 8-10 years |
| Disproportionate pain | 8-10 years |
| allodynia | 8-10 years |
| temperature asymmetry | 8-10 years |
| skin color asymmetry | 8-10 years |
| sweating asymmetry | 8-10 years |
| asymmetric edema | 8-10 years |
| trophic changes | 8-10 years |
| motor changes | 8-10 years |
| edema | 8-10 years |
| dystrophic changes | 8-10 years |
| skin changes | 8-10 years |
| nail changes | 8-10 years |
| hair changes | 8-10 years |
| motor abnormalities | 8-10 years |
| pinprick hyperalgesia | 8-10 years |
| hyperesthesia | 6-10 years |
| hyperalgesia | 6-10 years |
| Disproportionate pain | 6-10 years |
| allodynia | 6-10 years |
| temperature asymmetry | 6-10 years |
| skin color asymmetry | 6-10 years |
| sweating asymmetry | 6-10 years |
| asymmetric edema | 6-10 years |
| trophic changes | 6-10 years |
| motor changes | 6-10 years |
| edema | 6-10 years |
| dystrophic changes | 6-10 years |
| skin changes | 6-10 years |
| nail changes | 6-10 years |
| hair changes | 6-10 years |
| motor abnormalities | 6-10 years |
| pinprick hyperalgesia | 6-10 years |
| hyperesthesia | less than 2 years |
| hyperalgesia | less than 2 years |
| Disproportionate pain | less than 2 years |
| allodynia | less than 2 years |
| temperature asymmetry | less than 2 years |
| skin color asymmetry | less than 2 years |
| sweating asymmetry | less than 2 years |
| asymmetric edema | less than 2 years |
| trophic changes | less than 2 years |
| motor changes | less than 2 years |
| edema | less than 2 years |
| dystrophic changes | less than 2 years |
| skin changes | less than 2 years |
| nail changes | less than 2 years |
| hair changes | less than 2 years |
| motor abnormalities | less than 2 years |
| pinprick hyperalgesia | less than 2 years |
| hyperesthesia | at least 2 years |
| hyperalgesia | at least 2 years |
| Disproportionate pain | at least 2 years |
| allodynia | at least 2 years |
| temperature asymmetry | at least 2 years |
| skin color asymmetry | at least 2 years |
| sweating asymmetry | at least 2 years |
| asymmetric edema | at least 2 years |
| trophic changes | at least 2 years |
| motor changes | at least 2 years |
| edema | at least 2 years |
| dystrophic changes | at least 2 years |
| skin changes | at least 2 years |
| nail changes | at least 2 years |
| hair changes | at least 2 years |
| motor abnormalities | at least 2 years |
| pinprick hyperalgesia | at least 2 years |

TABLE IX

| Co-morbidity for which CRPS human patient receiving neridronic acid is selected | Duration of CRPS at Treatment Start for which CRPS human patient receiving neridronic acid is selected |
|---|---|
| back pain | 0-3 months |
| headache | 0-3 months |
| arthritis | 0-3 months |
| migraine | 0-3 months |
| arthralgia | 0-3 months |
| osteoarthritis | 0-3 months |
| psychiatric disorder | 0-3 months |
| anxiety | 0-3 months |
| depression (including moderate depression or severe depression) | 0-3 months |
| insomnia | 0-3 months |
| back pain | 3-6 months |
| headache | 3-6 months |
| arthritis | 3-6 months |
| migraine | 3-6 months |
| arthralgia | 3-6 months |
| osteoarthritis | 3-6 months |
| psychiatric disorder | 3-6 months |
| anxiety | 3-6 months |
| depression (including moderate depression or severe depression) | 3-6 months |
| insomnia | 3-6 months |
| back pain | 6-9 months |
| headache | 6-9 months |
| arthritis | 6-9 months |
| migraine | 6-9 months |
| arthralgia | 6-9 months |
| osteoarthritis | 6-9 months |
| psychiatric disorder | 6-9 months |

TABLE IX-continued

| Co-morbidity for which CRPS human patient receiving neridronic acid is selected | Duration of CRPS at Treatment Start for which CRPS human patient receiving neridronic acid is selected |
|---|---|
| anxiety | 6-9 months |
| depression (including moderate depression or severe depression) | 6-9 months |
| insomnia | 6-9 months |
| back pain | 9-12 months |
| headache | 9-12 months |
| arthritis | 9-12 months |
| migraine | 9-12 months |
| arthralgia | 9-12 months |
| osteoarthritis | 9-12 months |
| psychiatric disorder | 9-12 months |
| anxiety | 9-12 months |
| depression (including moderate depression or severe depression) | 9-12 months |
| insomnia | 9-12 months |
| back pain | 1-2 years |
| headache | 1-2 years |
| arthritis | 1-2 years |
| migraine | 1-2 years |
| arthralgia | 1-2 years |
| osteoarthritis | 1-2 years |
| psychiatric disorder | 1-2 years |
| anxiety | 1-2 years |
| depression (including moderate depression or severe depression) | 1-2 years |
| insomnia | 1-2 years |
| back pain | 2-4 years |
| headache | 2-4 years |
| arthritis | 2-4 years |
| migraine | 2-4 years |
| arthralgia | 2-4 years |
| osteoarthritis | 2-4 years |
| psychiatric disorder | 2-4 years |
| anxiety | 2-4 years |
| depression (including moderate depression or severe depression) | 2-4 years |
| insomnia | 2-4 years |
| back pain | 2-4 years |
| headache | 4-6 years |
| arthritis | 4-6 years |
| migraine | 4-6 years |
| arthralgia | 4-6 years |
| osteoarthritis | 4-6 years |
| psychiatric disorder | 4-6 years |
| anxiety | 4-6 years |
| depression (including moderate depression or severe depression) | 4-6 years |
| insomnia | 4-6 years |
| back pain | 6-8 years |
| headache | 6-8 years |
| arthritis | 6-8 years |
| migraine | 6-8 years |
| arthralgia | 6-8 years |
| osteoarthritis | 6-8 years |
| psychiatric disorder | 6-8 years |
| anxiety | 6-8 years |
| depression (including moderate depression or severe depression) | 6-8 years |
| insomnia | 6-8 years |
| back pain | 8-10 years |
| headache | 8-10 years |
| arthritis | 8-10 years |
| migraine | 8-10 years |
| arthralgia | 8-10 years |
| osteoarthritis | 8-10 years |
| psychiatric disorder | 8-10 years |
| anxiety | 8-10 years |
| depression (including moderate depression or severe depression) | 8-10 years |
| insomnia | 8-10 years |
| back pain | 6-10 years |
| headache | 6-10 years |
| arthritis | 6-10 years |
| migraine | 6-10 years |
| arthralgia | 6-10 years |
| osteoarthritis | 6-10 years |
| psychiatric disorder | 6-10 years |
| anxiety | 6-10 years |
| depression (including moderate depression or severe depression) | 6-10 years |
| insomnia | 6-10 years |
| back pain | less than 2 years |
| headache | less than 2 years |
| arthritis | less than 2 years |
| migraine | less than 2 years |
| arthralgia | less than 2 years |
| osteoarthritis | less than 2 years |
| psychiatric disorder | less than 2 years |
| anxiety | less than 2 years |
| depression (including moderate depression or severe depression) | less than 2 years |
| insomnia | less than 2 years |
| back pain | at least 2 years |
| headache | at least 2 years |
| arthritis | at least 2 years |
| migraine | at least 2 years |
| arthralgia | at least 2 years |
| osteoarthritis | at least 2 years |
| psychiatric disorder | at least 2 years |
| anxiety | at least 2 years |
| depression (including moderate depression or severe depression) | at least 2 years |
| insomnia | at least 2 years |

TABLE X

| Symptom for which CRPS human patient receiving neridronic acid is selected | Precipitating event for which CRPS human patient receiving neridronic acid is selected | Duration of CRPS at Treatment Start for which CRPS human patient receiving neridronic acid is selected |
|---|---|---|
| hyperesthesia | surgery | 0-3 months |
| hyperalgesia | surgery | 0-3 months |
| pinprick hyperalgesia | surgery | 0-3 months |
| allodynia | surgery | 0-3 months |
| temperature asymmetry | surgery | 0-3 months |
| skin color asymmetry | surgery | 0-3 months |
| sweating asymmetry | surgery | 0-3 months |
| asymmetric edema | surgery | 0-3 months |
| trophic changes | surgery | 0-3 months |
| motor changes | surgery | 0-3 months |
| edema | surgery | 0-3 months |
| dystrophic changes | surgery | 0-3 months |
| skin changes | surgery | 0-3 months |
| nail changes | surgery | 0-3 months |
| hair changes | surgery | 0-3 months |
| motor abnormalities | surgery | 0-3 months |
| hyperesthesia | fracture | 0-3 months |
| hyperalgesia | fracture | 0-3 months |
| pinprick hyperalgesia | fracture | 0-3 months |
| allodynia | fracture | 0-3 months |
| temperature asymmetry | fracture | 0-3 months |
| skin color asymmetry | fracture | 0-3 months |
| sweating asymmetry | fracture | 0-3 months |
| asymmetric edema | fracture | 0-3 months |
| trophic changes | fracture | 0-3 months |
| motor changes | fracture | 0-3 months |
| edema | fracture | 0-3 months |
| dystrophic changes | fracture | 0-3 months |
| skin changes | fracture | 0-3 months |
| nail changes | fracture | 0-3 months |
| hair changes | fracture | 0-3 months |
| motor abnormalities | fracture | 0-3 months |
| hyperesthesia | sprain | 0-3 months |
| hyperalgesia | sprain | 0-3 months |
| pinprick hyperalgesia | sprain | 0-3 months |
| allodynia | sprain | 0-3 months |

TABLE X-continued

| Symptom for which CRPS human patient receiving neridronic acid is selected | Precipitating event for which CRPS human patient receiving neridronic acid is selected | Duration of CRPS at Treatment Start for which CRPS human patient receiving neridronic acid is selected |
|---|---|---|
| temperature asymmetry | sprain | 0-3 months |
| skin color asymmetry | sprain | 0-3 months |
| sweating asymmetry | sprain | 0-3 months |
| asymmetric edema | sprain | 0-3 months |
| trophic changes | sprain | 0-3 months |
| motor changes | sprain | 0-3 months |
| edema | sprain | 0-3 months |
| dystrophic changes | sprain | 0-3 months |
| skin changes | sprain | 0-3 months |
| nail changes | sprain | 0-3 months |
| hair changes | sprain | 0-3 months |
| motor abnormalities | sprain | 0-3 months |
| hyperesthesia | crush | 0-3 months |
| hyperalgesia | crush | 0-3 months |
| pinprick hyperalgesia | crush | 0-3 months |
| allodynia | crush | 0-3 months |
| temperature asymmetry | crush | 0-3 months |
| skin color asymmetry | crush | 0-3 months |
| sweating asymmetry | crush | 0-3 months |
| asymmetric edema | crush | 0-3 months |
| trophic changes | crush | 0-3 months |
| motor changes | crush | 0-3 months |
| edema | crush | 0-3 months |
| dystrophic changes | crush | 0-3 months |
| skin changes | crush | 0-3 months |
| nail changes | crush | 0-3 months |
| hair changes | crush | 0-3 months |
| motor abnormalities | crush | 0-3 months |
| hyperesthesia | contusion | 0-3 months |
| hyperalgesia | contusion | 0-3 months |
| pinprick hyperalgesia | contusion | 0-3 months |
| allodynia | contusion | 0-3 months |
| temperature asymmetry | contusion | 0-3 months |
| skin color asymmetry | contusion | 0-3 months |
| sweating asymmetry | contusion | 0-3 months |
| asymmetric edema | contusion | 0-3 months |
| trophic changes | contusion | 0-3 months |
| motor changes | contusion | 0-3 months |
| edema | contusion | 0-3 months |
| dystrophic changes | contusion | 0-3 months |
| skin changes | contusion | 0-3 months |
| nail changes | contusion | 0-3 months |
| hair changes | contusion | 0-3 months |
| motor abnormalities | contusion | 0-3 months |
| hyperesthesia | dislocation | 0-3 months |
| hyperalgesia | dislocation | 0-3 months |
| pinprick hyperalgesia | dislocation | 0-3 months |
| allodynia | dislocation | 0-3 months |
| temperature asymmetry | dislocation | 0-3 months |
| skin color asymmetry | dislocation | 0-3 months |
| sweating asymmetry | dislocation | 0-3 months |
| asymmetric edema | dislocation | 0-3 months |
| trophic changes | dislocation | 0-3 months |
| motor changes | dislocation | 0-3 months |
| edema | dislocation | 0-3 months |
| dystrophic changes | dislocation | 0-3 months |
| skin changes | dislocation | 0-3 months |
| nail changes | dislocation | 0-3 months |
| hair changes | dislocation | 0-3 months |
| motor abnormalities | dislocation | 0-3 months |
| hyperesthesia | scratch | 0-3 months |
| hyperalgesia | scratch | 0-3 months |
| pinprick hyperalgesia | scratch | 0-3 months |
| allodynia | scratch | 0-3 months |
| temperature asymmetry | scratch | 0-3 months |
| skin color asymmetry | scratch | 0-3 months |
| sweating asymmetry | scratch | 0-3 months |
| asymmetric edema | scratch | 0-3 months |
| trophic changes | scratch | 0-3 months |
| motor changes | scratch | 0-3 months |
| edema | scratch | 0-3 months |
| dystrophic changes | scratch | 0-3 months |
| skin changes | scratch | 0-3 months |
| nail changes | scratch | 0-3 months |
| hair changes | scratch | 0-3 months |
| motor abnormalities | scratch | 0-3 months |
| hyperesthesia | skin puncture | 0-3 months |
| hyperalgesia | skin puncture | 0-3 months |
| pinprick hyperalgesia | skin puncture | 0-3 months |
| allodynia | skin puncture | 0-3 months |
| temperature asymmetry | skin puncture | 0-3 months |
| skin color asymmetry | skin puncture | 0-3 months |
| sweating asymmetry | skin puncture | 0-3 months |
| asymmetric edema | skin puncture | 0-3 months |
| trophic changes | skin puncture | 0-3 months |
| motor changes | skin puncture | 0-3 months |
| edema | skin puncture | 0-3 months |
| dystrophic changes | skin puncture | 0-3 months |
| skin changes | skin puncture | 0-3 months |
| nail changes | skin puncture | 0-3 months |
| hair changes | skin puncture | 0-3 months |
| motor abnormalities | skin puncture | 0-3 months |
| hyperesthesia | surgery | 3-6 months |
| hyperalgesia | surgery | 3-6 months |
| pinprick hyperalgesia | surgery | 3-6 months |
| allodynia | surgery | 3-6 months |
| temperature asymmetry | surgery | 3-6 months |
| skin color asymmetry | surgery | 3-6 months |
| sweating asymmetry | surgery | 3-6 months |
| asymmetric edema | surgery | 3-6 months |
| trophic changes | surgery | 3-6 months |
| motor changes | surgery | 3-6 months |
| edema | surgery | 3-6 months |
| dystrophic changes | surgery | 3-6 months |
| skin changes | surgery | 3-6 months |
| nail changes | surgery | 3-6 months |
| hair changes | surgery | 3-6 months |
| motor abnormalities | surgery | 3-6 months |
| hyperesthesia | fracture | 3-6 months |
| hyperalgesia | fracture | 3-6 months |
| pinprick hyperalgesia | fracture | 3-6 months |
| allodynia | fracture | 3-6 months |
| temperature asymmetry | fracture | 3-6 months |
| skin color asymmetry | fracture | 3-6 months |
| sweating asymmetry | fracture | 3-6 months |
| asymmetric edema | fracture | 3-6 months |
| trophic changes | fracture | 3-6 months |
| motor changes | fracture | 3-6 months |
| edema | fracture | 3-6 months |
| dystrophic changes | fracture | 3-6 months |
| skin changes | fracture | 3-6 months |
| nail changes | fracture | 3-6 months |
| hair changes | fracture | 3-6 months |
| motor abnormalities | fracture | 3-6 months |
| hyperesthesia | sprain | 3-6 months |
| hyperalgesia | sprain | 3-6 months |
| pinprick hyperalgesia | sprain | 3-6 months |
| allodynia | sprain | 3-6 months |
| temperature asymmetry | sprain | 3-6 months |
| skin color asymmetry | sprain | 3-6 months |
| sweating asymmetry | sprain | 3-6 months |
| asymmetric edema | sprain | 3-6 months |
| trophic changes | sprain | 3-6 months |
| motor changes | sprain | 3-6 months |
| edema | sprain | 3-6 months |
| dystrophic changes | sprain | 3-6 months |
| skin changes | sprain | 3-6 months |
| nail changes | sprain | 3-6 months |
| hair changes | sprain | 3-6 months |
| motor abnormalities | sprain | 3-6 months |
| hyperesthesia | crush | 3-6 months |
| hyperalgesia | crush | 3-6 months |
| pinprick hyperalgesia | crush | 3-6 months |
| allodynia | crush | 3-6 months |
| temperature asymmetry | crush | 3-6 months |
| skin color asymmetry | crush | 3-6 months |

TABLE X-continued

| Symptom for which CRPS human patient receiving neridronic acid is selected | Precipitating event for which CRPS human patient receiving neridronic acid is selected | Duration of CRPS at Treatment Start for which CRPS human patient receiving neridronic acid is selected |
| --- | --- | --- |
| sweating asymmetry | crush | 3-6 months |
| asymmetric edema | crush | 3-6 months |
| trophic changes | crush | 3-6 months |
| motor changes | crush | 3-6 months |
| edema | crush | 3-6 months |
| dystrophic changes | crush | 3-6 months |
| skin changes | crush | 3-6 months |
| nail changes | crush | 3-6 months |
| hair changes | crush | 3-6 months |
| motor abnormalities | crush | 3-6 months |
| hyperesthesia | contusion | 3-6 months |
| hyperalgesia | contusion | 3-6 months |
| pinprick hyperalgesia | contusion | 3-6 months |
| allodynia | contusion | 3-6 months |
| temperature asymmetry | contusion | 3-6 months |
| skin color asymmetry | contusion | 3-6 months |
| sweating asymmetry | contusion | 3-6 months |
| asymmetric edema | contusion | 3-6 months |
| trophic changes | contusion | 3-6 months |
| motor changes | contusion | 3-6 months |
| edema | contusion | 3-6 months |
| dystrophic changes | contusion | 3-6 months |
| skin changes | contusion | 3-6 months |
| nail changes | contusion | 3-6 months |
| hair changes | contusion | 3-6 months |
| motor abnormalities | contusion | 3-6 months |
| hyperesthesia | dislocation | 3-6 months |
| hyperalgesia | dislocation | 3-6 months |
| pinprick hyperalgesia | dislocation | 3-6 months |
| allodynia | dislocation | 3-6 months |
| temperature asymmetry | dislocation | 3-6 months |
| skin color asymmetry | dislocation | 3-6 months |
| sweating asymmetry | dislocation | 3-6 months |
| asymmetric edema | dislocation | 3-6 months |
| trophic changes | dislocation | 3-6 months |
| motor changes | dislocation | 3-6 months |
| edema | dislocation | 3-6 months |
| dystrophic changes | dislocation | 3-6 months |
| skin changes | dislocation | 3-6 months |
| nail changes | dislocation | 3-6 months |
| hair changes | dislocation | 3-6 months |
| motor abnormalities | dislocation | 3-6 months |
| hyperesthesia | scratch | 3-6 months |
| hyperalgesia | scratch | 3-6 months |
| pinprick hyperalgesia | scratch | 3-6 months |
| allodynia | scratch | 3-6 months |
| temperature asymmetry | scratch | 3-6 months |
| skin color asymmetry | scratch | 3-6 months |
| sweating asymmetry | scratch | 3-6 months |
| asymmetric edema | scratch | 3-6 months |
| trophic changes | scratch | 3-6 months |
| motor changes | scratch | 3-6 months |
| edema | scratch | 3-6 months |
| dystrophic changes | scratch | 3-6 months |
| skin changes | scratch | 3-6 months |
| nail changes | scratch | 3-6 months |
| hair changes | scratch | 3-6 months |
| motor abnormalities | scratch | 3-6 months |
| hyperesthesia | skin puncture | 3-6 months |
| hyperalgesia | skin puncture | 3-6 months |
| pinprick hyperalgesia | skin puncture | 3-6 months |
| allodynia | skin puncture | 3-6 months |
| temperature asymmetry | skin puncture | 3-6 months |
| skin color asymmetry | skin puncture | 3-6 months |
| sweating asymmetry | skin puncture | 3-6 months |
| asymmetric edema | skin puncture | 3-6 months |
| trophic changes | skin puncture | 3-6 months |
| motor changes | skin puncture | 3-6 months |
| edema | skin puncture | 3-6 months |
| dystrophic changes | skin puncture | 3-6 months |
| skin changes | skin puncture | 3-6 months |
| nail changes | skin puncture | 3-6 months |
| hair changes | skin puncture | 3-6 months |
| motor abnormalities | skin puncture | 3-6 months |
| hyperesthesia | surgery | 6-9 months |
| hyperalgesia | surgery | 6-9 months |
| pinprick hyperalgesia | surgery | 6-9 months |
| allodynia | surgery | 6-9 months |
| temperature asymmetry | surgery | 6-9 months |
| skin color asymmetry | surgery | 6-9 months |
| sweating asymmetry | surgery | 6-9 months |
| asymmetric edema | surgery | 6-9 months |
| trophic changes | surgery | 6-9 months |
| motor changes | surgery | 6-9 months |
| edema | surgery | 6-9 months |
| dystrophic changes | surgery | 6-9 months |
| skin changes | surgery | 6-9 months |
| nail changes | surgery | 6-9 months |
| hair changes | surgery | 6-9 months |
| motor abnormalities | surgery | 6-9 months |
| hyperesthesia | fracture | 6-9 months |
| hyperalgesia | fracture | 6-9 months |
| pinprick hyperalgesia | fracture | 6-9 months |
| allodynia | fracture | 6-9 months |
| temperature asymmetry | fracture | 6-9 months |
| skin color asymmetry | fracture | 6-9 months |
| sweating asymmetry | fracture | 6-9 months |
| asymmetric edema | fracture | 6-9 months |
| trophic changes | fracture | 6-9 months |
| motor changes | fracture | 6-9 months |
| edema | fracture | 6-9 months |
| dystrophic changes | fracture | 6-9 months |
| skin changes | fracture | 6-9 months |
| nail changes | fracture | 6-9 months |
| hair changes | fracture | 6-9 months |
| motor abnormalities | fracture | 6-9 months |
| hyperesthesia | sprain | 6-9 months |
| hyperalgesia | sprain | 6-9 months |
| pinprick hyperalgesia | sprain | 6-9 months |
| allodynia | sprain | 6-9 months |
| temperature asymmetry | sprain | 6-9 months |
| skin color asymmetry | sprain | 6-9 months |
| sweating asymmetry | sprain | 6-9 months |
| asymmetric edema | sprain | 6-9 months |
| trophic changes | sprain | 6-9 months |
| motor changes | sprain | 6-9 months |
| edema | sprain | 6-9 months |
| dystrophic changes | sprain | 6-9 months |
| skin changes | sprain | 6-9 months |
| nail changes | sprain | 6-9 months |
| hair changes | sprain | 6-9 months |
| motor abnormalities | sprain | 6-9 months |
| hyperesthesia | crush | 6-9 months |
| hyperalgesia | crush | 6-9 months |
| pinprick hyperalgesia | crush | 6-9 months |
| allodynia | crush | 6-9 months |
| temperature asymmetry | crush | 6-9 months |
| skin color asymmetry | crush | 6-9 months |
| sweating asymmetry | crush | 6-9 months |
| asymmetric edema | crush | 6-9 months |
| trophic changes | crush | 6-9 months |
| motor changes | crush | 6-9 months |
| edema | crush | 6-9 months |
| dystrophic changes | crush | 6-9 months |
| skin changes | crush | 6-9 months |
| nail changes | crush | 6-9 months |
| hair changes | crush | 6-9 months |
| motor abnormalities | crush | 6-9 months |
| hyperesthesia | contusion | 6-9 months |
| hyperalgesia | contusion | 6-9 months |
| pinprick hyperalgesia | contusion | 6-9 months |
| allodynia | contusion | 6-9 months |
| temperature asymmetry | contusion | 6-9 months |
| skin color asymmetry | contusion | 6-9 months |
| sweating asymmetry | contusion | 6-9 months |
| asymmetric edema | contusion | 6-9 months |

TABLE X-continued

| Symptom for which CRPS human patient receiving neridronic acid is selected | Precipitating event for which CRPS human patient receiving neridronic acid is selected | Duration of CRPS at Treatment Start for which CRPS human patient receiving neridronic acid is selected |
|---|---|---|
| trophic changes | contusion | 6-9 months |
| motor changes | contusion | 6-9 months |
| edema | contusion | 6-9 months |
| dystrophic changes | contusion | 6-9 months |
| skin changes | contusion | 6-9 months |
| nail changes | contusion | 6-9 months |
| hair changes | contusion | 6-9 months |
| motor abnormalities | contusion | 6-9 months |
| hyperesthesia | dislocation | 6-9 months |
| hyperalgesia | dislocation | 6-9 months |
| pinprick hyperalgesia | dislocation | 6-9 months |
| allodynia | dislocation | 6-9 months |
| temperature asymmetry | dislocation | 6-9 months |
| skin color asymmetry | dislocation | 6-9 months |
| sweating asymmetry | dislocation | 6-9 months |
| asymmetric edema | dislocation | 6-9 months |
| trophic changes | dislocation | 6-9 months |
| motor changes | dislocation | 6-9 months |
| edema | dislocation | 6-9 months |
| dystrophic changes | dislocation | 6-9 months |
| skin changes | dislocation | 6-9 months |
| nail changes | dislocation | 6-9 months |
| hair changes | dislocation | 6-9 months |
| motor abnormalities | dislocation | 6-9 months |
| hyperesthesia | scratch | 6-9 months |
| hyperalgesia | scratch | 6-9 months |
| pinprick hyperalgesia | scratch | 6-9 months |
| allodynia | scratch | 6-9 months |
| temperature asymmetry | scratch | 6-9 months |
| skin color asymmetry | scratch | 6-9 months |
| sweating asymmetry | scratch | 6-9 months |
| asymmetric edema | scratch | 6-9 months |
| trophic changes | scratch | 6-9 months |
| motor changes | scratch | 6-9 months |
| edema | scratch | 6-9 months |
| dystrophic changes | scratch | 6-9 months |
| skin changes | scratch | 6-9 months |
| nail changes | scratch | 6-9 months |
| hair changes | scratch | 6-9 months |
| motor abnormalities | scratch | 6-9 months |
| hyperesthesia | skin puncture | 6-9 months |
| hyperalgesia | skin puncture | 6-9 months |
| pinprick hyperalgesia | skin puncture | 6-9 months |
| allodynia | skin puncture | 6-9 months |
| temperature asymmetry | skin puncture | 6-9 months |
| skin color asymmetry | skin puncture | 6-9 months |
| sweating asymmetry | skin puncture | 6-9 months |
| asymmetric edema | skin puncture | 6-9 months |
| trophic changes | skin puncture | 6-9 months |
| motor changes | skin puncture | 6-9 months |
| edema | skin puncture | 6-9 months |
| dystrophic changes | skin puncture | 6-9 months |
| skin changes | skin puncture | 6-9 months |
| nail changes | skin puncture | 6-9 months |
| hair changes | skin puncture | 6-9 months |
| motor abnormalities | skin puncture | 6-9 months |
| hyperesthesia | surgery | 9-12 months |
| hyperalgesia | surgery | 9-12 months |
| pinprick hyperalgesia | surgery | 9-12 months |
| allodynia | surgery | 9-12 months |
| temperature asymmetry | surgery | 9-12 months |
| skin color asymmetry | surgery | 9-12 months |
| sweating asymmetry | surgery | 9-12 months |
| asymmetric edema | surgery | 9-12 months |
| trophic changes | surgery | 9-12 months |
| motor changes | surgery | 9-12 months |
| edema | surgery | 9-12 months |
| dystrophic changes | surgery | 9-12 months |
| skin changes | surgery | 9-12 months |
| nail changes | surgery | 9-12 months |
| hair changes | surgery | 9-12 months |
| motor abnormalities | surgery | 9-12 months |
| hyperesthesia | fracture | 9-12 months |
| hyperalgesia | fracture | 9-12 months |
| pinprick hyperalgesia | fracture | 9-12 months |
| allodynia | fracture | 9-12 months |
| temperature asymmetry | fracture | 9-12 months |
| skin color asymmetry | fracture | 9-12 months |
| sweating asymmetry | fracture | 9-12 months |
| asymmetric edema | fracture | 9-12 months |
| trophic changes | fracture | 9-12 months |
| motor changes | fracture | 9-12 months |
| edema | fracture | 9-12 months |
| dystrophic changes | fracture | 9-12 months |
| skin changes | fracture | 9-12 months |
| nail changes | fracture | 9-12 months |
| hair changes | fracture | 9-12 months |
| motor abnormalities | fracture | 9-12 months |
| hyperesthesia | sprain | 9-12 months |
| hyperalgesia | sprain | 9-12 months |
| pinprick hyperalgesia | sprain | 9-12 months |
| allodynia | sprain | 9-12 months |
| temperature asymmetry | sprain | 9-12 months |
| skin color asymmetry | sprain | 9-12 months |
| sweating asymmetry | sprain | 9-12 months |
| asymmetric edema | sprain | 9-12 months |
| trophic changes | sprain | 9-12 months |
| motor changes | sprain | 9-12 months |
| edema | sprain | 9-12 months |
| dystrophic changes | sprain | 9-12 months |
| skin changes | sprain | 9-12 months |
| nail changes | sprain | 9-12 months |
| hair changes | sprain | 9-12 months |
| motor abnormalities | sprain | 9-12 months |
| hyperesthesia | crush | 9-12 months |
| hyperalgesia | crush | 9-12 months |
| pinprick hyperalgesia | crush | 9-12 months |
| allodynia | crush | 9-12 months |
| temperature asymmetry | crush | 9-12 months |
| skin color asymmetry | crush | 9-12 months |
| sweating asymmetry | crush | 9-12 months |
| asymmetric edema | crush | 9-12 months |
| trophic changes | crush | 9-12 months |
| motor changes | crush | 9-12 months |
| edema | crush | 9-12 months |
| dystrophic changes | crush | 9-12 months |
| skin changes | crush | 9-12 months |
| nail changes | crush | 9-12 months |
| hair changes | crush | 9-12 months |
| motor abnormalities | crush | 9-12 months |
| hyperesthesia | contusion | 9-12 months |
| hyperalgesia | contusion | 9-12 months |
| pinprick hyperalgesia | contusion | 9-12 months |
| allodynia | contusion | 9-12 months |
| temperature asymmetry | contusion | 9-12 months |
| skin color asymmetry | contusion | 9-12 months |
| sweating asymmetry | contusion | 9-12 months |
| asymmetric edema | contusion | 9-12 months |
| trophic changes | contusion | 9-12 months |
| motor changes | contusion | 9-12 months |
| edema | contusion | 9-12 months |
| dystrophic changes | contusion | 9-12 months |
| skin changes | contusion | 9-12 months |
| nail changes | contusion | 9-12 months |
| hair changes | contusion | 9-12 months |
| motor abnormalities | contusion | 9-12 months |
| hyperesthesia | dislocation | 9-12 months |
| hyperalgesia | dislocation | 9-12 months |
| pinprick hyperalgesia | dislocation | 9-12 months |
| allodynia | dislocation | 9-12 months |
| temperature asymmetry | dislocation | 9-12 months |
| skin color asymmetry | dislocation | 9-12 months |
| sweating asymmetry | dislocation | 9-12 months |
| asymmetric edema | dislocation | 9-12 months |
| trophic changes | dislocation | 9-12 months |
| motor changes | dislocation | 9-12 months |

TABLE X-continued

| Symptom for which CRPS human patient receiving neridronic acid is selected | Precipitating event for which CRPS human patient receiving neridronic acid is selected | Duration of CRPS at Treatment Start for which CRPS human patient receiving neridronic acid is selected |
|---|---|---|
| edema | dislocation | 9-12 months |
| dystrophic changes | dislocation | 9-12 months |
| skin changes | dislocation | 9-12 months |
| nail changes | dislocation | 9-12 months |
| hair changes | dislocation | 9-12 months |
| motor abnormalities | dislocation | 9-12 months |
| hyperesthesia | scratch | 9-12 months |
| hyperalgesia | scratch | 9-12 months |
| Pinprick hyperalgesia | scratch | 9-12 months |
| allodynia | scratch | 9-12 months |
| temperature asymmetry | scratch | 9-12 months |
| skin color asymmetry | scratch | 9-12 months |
| sweating asymmetry | scratch | 9-12 months |
| asymmetric edema | scratch | 9-12 months |
| trophic changes | scratch | 9-12 months |
| motor changes | scratch | 9-12 months |
| edema | scratch | 9-12 months |
| dystrophic changes | scratch | 9-12 months |
| skin changes | scratch | 9-12 months |
| nail changes | scratch | 9-12 months |
| hair changes | scratch | 9-12 months |
| motor abnormalities | scratch | 9-12 months |
| hyperesthesia | skin puncture | 9-12 months |
| hyperalgesia | skin puncture | 9-12 months |
| pinprick hyperalgesia | skin puncture | 9-12 months |
| allodynia | skin puncture | 9-12 months |
| temperature asymmetry | skin puncture | 9-12 months |
| skin color asymmetry | skin puncture | 9-12 months |
| sweating asymmetry | skin puncture | 9-12 months |
| asymmetric edema | skin puncture | 9-12 months |
| trophic changes | skin puncture | 9-12 months |
| motor changes | skin puncture | 9-12 months |
| edema | skin puncture | 9-12 months |
| dystrophic changes | skin puncture | 9-12 months |
| skin changes | skin puncture | 9-12 months |
| nail changes | skin puncture | 9-12 months |
| hair changes | skin puncture | 9-12 months |
| motor abnormalities | skin puncture | 9-12 months |
| hyperesthesia | surgery | 1-2 years |
| hyperalgesia | surgery | 1-2 years |
| pinprick hyperalgesia | surgery | 1-2 years |
| allodynia | surgery | 1-2 years |
| temperature asymmetry | surgery | 1-2 years |
| skin color asymmetry | surgery | 1-2 years |
| sweating asymmetry | surgery | 1-2 years |
| asymmetric edema | surgery | 1-2 years |
| trophic changes | surgery | 1-2 years |
| motor changes | surgery | 1-2 years |
| edema | surgery | 1-2 years |
| dystrophic changes | surgery | 1-2 years |
| skin changes | surgery | 1-2 years |
| nail changes | surgery | 1-2 years |
| hair changes | surgery | 1-2 years |
| motor abnormalities | surgery | 1-2 years |
| hyperesthesia | fracture | 1-2 years |
| hyperalgesia | fracture | 1-2 years |
| pinprick hyperalgesia | fracture | 1-2 years |
| allodynia | fracture | 1-2 years |
| temperature asymmetry | fracture | 1-2 years |
| skin color asymmetry | fracture | 1-2 years |
| sweating asymmetry | fracture | 1-2 years |
| asymmetric edema | fracture | 1-2 years |
| trophic changes | fracture | 1-2 years |
| motor changes | fracture | 1-2 years |
| edema | fracture | 1-2 years |
| dystrophic changes | fracture | 1-2 years |
| skin changes | fracture | 1-2 years |
| nail changes | fracture | 1-2 years |
| hair changes | fracture | 1-2 years |
| motor abnormalities | fracture | 1-2 years |
| hyperesthesia | sprain | 1-2 years |
| hyperalgesia | sprain | 1-2 years |
| pinprick hyperalgesia | sprain | 1-2 years |
| allodynia | sprain | 1-2 years |
| temperature asymmetry | sprain | 1-2 years |
| skin color asymmetry | sprain | 1-2 years |
| sweating asymmetry | sprain | 1-2 years |
| asymmetric edema | sprain | 1-2 years |
| trophic changes | sprain | 1-2 years |
| motor changes | sprain | 1-2 years |
| edema | sprain | 1-2 years |
| dystrophic changes | sprain | 1-2 years |
| skin changes | sprain | 1-2 years |
| nail changes | sprain | 1-2 years |
| hair changes | sprain | 1-2 years |
| motor abnormalities | sprain | 1-2 years |
| hyperesthesia | crush | 1-2 years |
| hyperalgesia | crush | 1-2 years |
| pinprick hyperalgesia | crush | 1-2 years |
| allodynia | crush | 1-2 years |
| temperature asymmetry | crush | 1-2 years |
| skin color asymmetry | crush | 1-2 years |
| sweating asymmetry | crush | 1-2 years |
| asymmetric edema | crush | 1-2 years |
| trophic changes | crush | 1-2 years |
| motor changes | crush | 1-2 years |
| edema | crush | 1-2 years |
| dystrophic changes | crush | 1-2 years |
| skin changes | crush | 1-2 years |
| nail changes | crush | 1-2 years |
| hair changes | crush | 1-2 years |
| motor abnormalities | crush | 1-2 years |
| hyperesthesia | contusion | 1-2 years |
| hyperalgesia | contusion | 1-2 years |
| pinprick hyperalgesia | contusion | 1-2 years |
| allodynia | contusion | 1-2 years |
| temperature asymmetry | contusion | 1-2 years |
| skin color asymmetry | contusion | 1-2 years |
| sweating asymmetry | contusion | 1-2 years |
| asymmetric edema | contusion | 1-2 years |
| trophic changes | contusion | 1-2 years |
| motor changes | contusion | 1-2 years |
| edema | contusion | 1-2 years |
| dystrophic changes | contusion | 1-2 years |
| skin changes | contusion | 1-2 years |
| nail changes | contusion | 1-2 years |
| hair changes | contusion | 1-2 years |
| motor abnormalities | contusion | 1-2 years |
| hyperesthesia | dislocation | 1-2 years |
| hyperalgesia | dislocation | 1-2 years |
| pinprick hyperalgesia | dislocation | 1-2 years |
| allodynia | dislocation | 1-2 years |
| temperature asymmetry | dislocation | 1-2 years |
| skin color asymmetry | dislocation | 1-2 years |
| sweating asymmetry | dislocation | 1-2 years |
| asymmetric edema | dislocation | 1-2 years |
| trophic changes | dislocation | 1-2 years |
| motor changes | dislocation | 1-2 years |
| edema | dislocation | 1-2 years |
| dystrophic changes | dislocation | 1-2 years |
| skin changes | dislocation | 1-2 years |
| nail changes | dislocation | 1-2 years |
| hair changes | dislocation | 1-2 years |
| motor abnormalities | dislocation | 1-2 years |
| hyperesthesia | scratch | 1-2 years |
| hyperalgesia | scratch | 1-2 years |
| pinprick hyperalgesia | scratch | 1-2 years |
| allodynia | scratch | 1-2 years |
| temperature asymmetry | scratch | 1-2 years |
| skin color asymmetry | scratch | 1-2 years |
| sweating asymmetry | scratch | 1-2 years |
| asymmetric edema | scratch | 1-2 years |
| trophic changes | scratch | 1-2 years |
| motor changes | scratch | 1-2 years |
| edema | scratch | 1-2 years |
| dystrophic changes | scratch | 1-2 years |

TABLE X-continued

| Symptom for which CRPS human patient receiving neridronic acid is selected | Precipitating event for which CRPS human patient receiving neridronic acid is selected | Duration of CRPS at Treatment Start for which CRPS human patient receiving neridronic acid is selected |
|---|---|---|
| skin changes | scratch | 1-2 years |
| nail changes | scratch | 1-2 years |
| hair changes | scratch | 1-2 years |
| motor abnormalities | scratch | 1-2 years |
| hyperesthesia | skin puncture | 1-2 years |
| hyperalgesia | skin puncture | 1-2 years |
| pinprick hyperalgesia | skin puncture | 1-2 years |
| allodynia | skin puncture | 1-2 years |
| temperature asymmetry | skin puncture | 1-2 years |
| skin color asymmetry | skin puncture | 1-2 years |
| sweating asymmetry | skin puncture | 1-2 years |
| asymmetric edema | skin puncture | 1-2 years |
| trophic changes | skin puncture | 1-2 years |
| motor changes | skin puncture | 1-2 years |
| edema | skin puncture | 1-2 years |
| dystrophic changes | skin puncture | 1-2 years |
| skin changes | skin puncture | 1-2 years |
| nail changes | skin puncture | 1-2 years |
| hair changes | skin puncture | 1-2 years |
| motor abnormalities | skin puncture | 1-2 years |
| hyperesthesia | surgery | 2-4 years |
| hyperalgesia | surgery | 2-4 years |
| pinprick hyperalgesia | surgery | 2-4 years |
| allodynia | surgery | 2-4 years |
| temperature asymmetry | surgery | 2-4 years |
| skin color asymmetry | surgery | 2-4 years |
| sweating asymmetry | surgery | 2-4 years |
| asymmetric edema | surgery | 2-4 years |
| trophic changes | surgery | 2-4 years |
| motor changes | surgery | 2-4 years |
| edema | surgery | 2-4 years |
| dystrophic changes | surgery | 2-4 years |
| skin changes | surgery | 2-4 years |
| nail changes | surgery | 2-4 years |
| hair changes | surgery | 2-4 years |
| motor abnormalities | surgery | 2-4 years |
| hyperesthesia | fracture | 2-4 years |
| hyperalgesia | fracture | 2-4 years |
| pinprick hyperalgesia | fracture | 2-4 years |
| allodynia | fracture | 2-4 years |
| temperature asymmetry | fracture | 2-4 years |
| skin color asymmetry | fracture | 2-4 years |
| sweating asymmetry | fracture | 2-4 years |
| asymmetric edema | fracture | 2-4 years |
| trophic changes | fracture | 2-4 years |
| motor changes | fracture | 2-4 years |
| edema | fracture | 2-4 years |
| dystrophic changes | fracture | 2-4 years |
| skin changes | fracture | 2-4 years |
| nail changes | fracture | 2-4 years |
| hair changes | fracture | 2-4 years |
| motor abnormalities | fracture | 2-4 years |
| hyperesthesia | sprain | 2-4 years |
| hyperalgesia | sprain | 2-4 years |
| pinprick hyperalgesia | sprain | 2-4 years |
| allodynia | sprain | 2-4 years |
| temperature asymmetry | sprain | 2-4 years |
| skin color asymmetry | sprain | 2-4 years |
| sweating asymmetry | sprain | 2-4 years |
| asymmetric edema | sprain | 2-4 years |
| trophic changes | sprain | 2-4 years |
| motor changes | sprain | 2-4 years |
| edema | sprain | 2-4 years |
| dystrophic changes | sprain | 2-4 years |
| skin changes | sprain | 2-4 years |
| nail changes | sprain | 2-4 years |
| hair changes | sprain | 2-4 years |
| motor abnormalities | sprain | 2-4 years |
| hyperesthesia | crush | 2-4 years |
| hyperalgesia | crush | 2-4 years |
| pinprick hyperalgesia | crush | 2-4 years |
| allodynia | crush | 2-4 years |
| temperature asymmetry | crush | 2-4 years |
| skin color asymmetry | crush | 2-4 years |
| sweating asymmetry | crush | 2-4 years |
| asymmetric edema | crush | 2-4 years |
| trophic changes | crush | 2-4 years |
| motor changes | crush | 2-4 years |
| edema | crush | 2-4 years |
| dystrophic changes | crush | 2-4 years |
| skin changes | crush | 2-4 years |
| nail changes | crush | 2-4 years |
| hair changes | crush | 2-4 years |
| motor abnormalities | crush | 2-4 years |
| hyperesthesia | contusion | 2-4 years |
| hyperalgesia | contusion | 2-4 years |
| pinprick hyperalgesia | contusion | 2-4 years |
| allodynia | contusion | 2-4 years |
| temperature asymmetry | contusion | 2-4 years |
| skin color asymmetry | contusion | 2-4 years |
| sweating asymmetry | contusion | 2-4 years |
| asymmetric edema | contusion | 2-4 years |
| trophic changes | contusion | 2-4 years |
| motor changes | contusion | 2-4 years |
| edema | contusion | 2-4 years |
| dystrophic changes | contusion | 2-4 years |
| skin changes | contusion | 2-4 years |
| nail changes | contusion | 2-4 years |
| hair changes | contusion | 2-4 years |
| motor abnormalities | contusion | 2-4 years |
| hyperesthesia | dislocation | 2-4 years |
| hyperalgesia | dislocation | 2-4 years |
| pinprick hyperalgesia | dislocation | 2-4 years |
| allodynia | dislocation | 2-4 years |
| temperature asymmetry | dislocation | 2-4 years |
| skin color asymmetry | dislocation | 2-4 years |
| sweating asymmetry | dislocation | 2-4 years |
| asymmetric edema | dislocation | 2-4 years |
| trophic changes | dislocation | 2-4 years |
| motor changes | dislocation | 2-4 years |
| edema | dislocation | 2-4 years |
| dystrophic changes | dislocation | 2-4 years |
| skin changes | dislocation | 2-4 years |
| nail changes | dislocation | 2-4 years |
| hair changes | dislocation | 2-4 years |
| motor abnormalities | dislocation | 2-4 years |
| hyperesthesia | scratch | 2-4 years |
| hyperalgesia | scratch | 2-4 years |
| pinprick hyperalgesia | scratch | 2-4 years |
| allodynia | scratch | 2-4 years |
| temperature asymmetry | scratch | 2-4 years |
| skin color asymmetry | scratch | 2-4 years |
| sweating asymmetry | scratch | 2-4 years |
| asymmetric edema | scratch | 2-4 years |
| trophic changes | scratch | 2-4 years |
| motor changes | scratch | 2-4 years |
| edema | scratch | 2-4 years |
| dystrophic changes | scratch | 2-4 years |
| skin changes | scratch | 2-4 years |
| nail changes | scratch | 2-4 years |
| hair changes | scratch | 2-4 years |
| motor abnormalities | scratch | 2-4 years |
| hyperesthesia | skin puncture | 2-4 years |
| hyperalgesia | skin puncture | 2-4 years |
| pinprick hyperalgesia | skin puncture | 2-4 years |
| allodynia | skin puncture | 2-4 years |
| temperature asymmetry | skin puncture | 2-4 years |
| skin color asymmetry | skin puncture | 2-4 years |
| sweating asymmetry | skin puncture | 2-4 years |
| asymmetric edema | skin puncture | 2-4 years |
| trophic changes | skin puncture | 2-4 years |
| motor changes | skin puncture | 2-4 years |
| edema | skin puncture | 2-4 years |
| dystrophic changes | skin puncture | 2-4 years |
| skin changes | skin puncture | 2-4 years |
| nail changes | skin puncture | 2-4 years |

TABLE X-continued

| Symptom for which CRPS human patient receiving neridronic acid is selected | Precipitating event for which CRPS human patient receiving neridronic acid is selected | Duration of CRPS at Treatment Start for which CRPS human patient receiving neridronic acid is selected |
|---|---|---|
| hair changes | skin puncture | 2-4 years |
| motor abnormalities | skin puncture | 2-4 years |
| hyperesthesia | surgery | 4-6 years |
| hyperalgesia | surgery | 4-6 years |
| pinprick hyperalgesia | surgery | 4-6 years |
| allodynia | surgery | 4-6 years |
| temperature asymmetry | surgery | 4-6 years |
| skin color asymmetry | surgery | 4-6 years |
| sweating asymmetry | surgery | 4-6 years |
| asymmetric edema | surgery | 4-6 years |
| trophic changes | surgery | 4-6 years |
| motor changes | surgery | 4-6 years |
| edema | surgery | 4-6 years |
| dystrophic changes | surgery | 4-6 years |
| skin changes | surgery | 4-6 years |
| nail changes | surgery | 4-6 years |
| hair changes | surgery | 4-6 years |
| motor abnormalities | surgery | 4-6 years |
| hyperesthesia | fracture | 4-6 years |
| hyperalgesia | fracture | 4-6 years |
| pinprick hyperalgesia | fracture | 4-6 years |
| allodynia | fracture | 4-6 years |
| temperature asymmetry | fracture | 4-6 years |
| skin color asymmetry | fracture | 4-6 years |
| sweating asymmetry | fracture | 4-6 years |
| asymmetric edema | fracture | 4-6 years |
| trophic changes | fracture | 4-6 years |
| motor changes | fracture | 4-6 years |
| edema | fracture | 4-6 years |
| dystrophic changes | fracture | 4-6 years |
| skin changes | fracture | 4-6 years |
| nail changes | fracture | 4-6 years |
| hair changes | fracture | 4-6 years |
| motor abnormalities | fracture | 4-6 years |
| hyperesthesia | sprain | 4-6 years |
| hyperalgesia | sprain | 4-6 years |
| pinprick hyperalgesia | sprain | 4-6 years |
| allodynia | sprain | 4-6 years |
| temperature asymmetry | sprain | 4-6 years |
| skin color asymmetry | sprain | 4-6 years |
| sweating asymmetry | sprain | 4-6 years |
| asymmetric edema | sprain | 4-6 years |
| trophic changes | sprain | 4-6 years |
| motor changes | sprain | 4-6 years |
| edema | sprain | 4-6 years |
| dystrophic changes | sprain | 4-6 years |
| skin changes | sprain | 4-6 years |
| nail changes | sprain | 4-6 years |
| hair changes | sprain | 4-6 years |
| motor abnormalities | sprain | 4-6 years |
| hyperesthesia | crush | 4-6 years |
| hyperalgesia | crush | 4-6 years |
| pinprick hyperalgesia | crush | 4-6 years |
| allodynia | crush | 4-6 years |
| temperature asymmetry | crush | 4-6 years |
| skin color asymmetry | crush | 4-6 years |
| sweating asymmetry | crush | 4-6 years |
| asymmetric edema | crush | 4-6 years |
| trophic changes | crush | 4-6 years |
| motor changes | crush | 4-6 years |
| edema | crush | 4-6 years |
| dystrophic changes | crush | 4-6 years |
| skin changes | crush | 4-6 years |
| nail changes | crush | 4-6 years |
| hair changes | crush | 4-6 years |
| motor abnormalities | crush | 4-6 years |
| hyperesthesia | contusion | 4-6 years |
| hyperalgesia | contusion | 4-6 years |
| pinprick hyperalgesia | contusion | 4-6 years |
| allodynia | contusion | 4-6 years |
| temperature asymmetry | contusion | 4-6 years |
| skin color asymmetry | contusion | 4-6 years |
| sweating asymmetry | contusion | 4-6 years |
| asymmetric edema | contusion | 4-6 years |
| trophic changes | contusion | 4-6 years |
| motor changes | contusion | 4-6 years |
| edema | contusion | 4-6 years |
| dystrophic changes | contusion | 4-6 years |
| skin changes | contusion | 4-6 years |
| nail changes | contusion | 4-6 years |
| hair changes | contusion | 4-6 years |
| motor abnormalities | contusion | 4-6 years |
| hyperesthesia | dislocation | 4-6 years |
| hyperalgesia | dislocation | 4-6 years |
| pinprick hyperalgesia | dislocation | 4-6 years |
| allodynia | dislocation | 4-6 years |
| temperature asymmetry | dislocation | 4-6 years |
| skin color asymmetry | dislocation | 4-6 years |
| sweating asymmetry | dislocation | 4-6 years |
| asymmetric edema | dislocation | 4-6 years |
| trophic changes | dislocation | 4-6 years |
| motor changes | dislocation | 4-6 years |
| edema | dislocation | 4-6 years |
| dystrophic changes | dislocation | 4-6 years |
| skin changes | dislocation | 4-6 years |
| nail changes | dislocation | 4-6 years |
| hair changes | dislocation | 4-6 years |
| motor abnormalities | dislocation | 4-6 years |
| hyperesthesia | scratch | 4-6 years |
| hyperalgesia | scratch | 4-6 years |
| pinprick hyperalgesia | scratch | 4-6 years |
| allodynia | scratch | 4-6 years |
| temperature asymmetry | scratch | 4-6 years |
| skin color asymmetry | scratch | 4-6 years |
| sweating asymmetry | scratch | 4-6 years |
| asymmetric edema | scratch | 4-6 years |
| trophic changes | scratch | 4-6 years |
| motor changes | scratch | 4-6 years |
| edema | scratch | 4-6 years |
| dystrophic changes | scratch | 4-6 years |
| skin changes | scratch | 4-6 years |
| nail changes | scratch | 4-6 years |
| hair changes | scratch | 4-6 years |
| motor abnormalities | scratch | 4-6 years |
| hyperesthesia | skin puncture | 4-6 years |
| hyperalgesia | skin puncture | 4-6 years |
| pinprick hyperalgesia | skin puncture | 4-6 years |
| allodynia | skin puncture | 4-6 years |
| temperature asymmetry | skin puncture | 4-6 years |
| skin color asymmetry | skin puncture | 4-6 years |
| sweating asymmetry | skin puncture | 4-6 years |
| asymmetric edema | skin puncture | 4-6 years |
| trophic changes | skin puncture | 4-6 years |
| motor changes | skin puncture | 4-6 years |
| edema | skin puncture | 4-6 years |
| dystrophic changes | skin puncture | 4-6 years |
| skin changes | skin puncture | 4-6 years |
| nail changes | skin puncture | 4-6 years |
| hair changes | skin puncture | 4-6 years |
| motor abnormalities | skin puncture | 4-6 years |
| hyperesthesia | surgery | 6-10 years |
| hyperalgesia | surgery | 6-10 years |
| pinprick hyperalgesia | surgery | 6-10 years |
| allodynia | surgery | 6-10 years |
| temperature asymmetry | surgery | 6-10 years |
| skin color asymmetry | surgery | 6-10 years |
| sweating asymmetry | surgery | 6-10 years |
| asymmetric edema | surgery | 6-10 years |
| trophic changes | surgery | 6-10 years |
| motor changes | surgery | 6-10 years |
| edema | surgery | 6-10 years |
| dystrophic changes | surgery | 6-10 years |
| skin changes | surgery | 6-10 years |
| nail changes | surgery | 6-10 years |
| hair changes | surgery | 6-10 years |
| motor abnormalities | surgery | 6-10 years |

TABLE X-continued

| Symptom for which CRPS human patient receiving neridronic acid is selected | Precipitating event for which CRPS human patient receiving neridronic acid is selected | Duration of CRPS at Treatment Start for which CRPS human patient receiving neridronic acid is selected |
|---|---|---|
| hyperesthesia | fracture | 6-10 years |
| hyperalgesia | fracture | 6-10 years |
| pinprick hyperalgesia | fracture | 6-10 years |
| allodynia | fracture | 6-10 years |
| temperature asymmetry | fracture | 6-10 years |
| skin color asymmetry | fracture | 6-10 years |
| sweating asymmetry | fracture | 6-10 years |
| asymmetric edema | fracture | 6-10 years |
| trophic changes | fracture | 6-10 years |
| motor changes | fracture | 6-10 years |
| edema | fracture | 6-10 years |
| dystrophic changes | fracture | 6-10 years |
| skin changes | fracture | 6-10 years |
| nail changes | fracture | 6-10 years |
| hair changes | fracture | 6-10 years |
| motor abnormalities | fracture | 6-10 years |
| hyperesthesia | sprain | 6-10 years |
| hyperalgesia | sprain | 6-10 years |
| pinprick hyperalgesia | sprain | 6-10 years |
| allodynia | sprain | 6-10 years |
| temperature asymmetry | sprain | 6-10 years |
| skin color asymmetry | sprain | 6-10 years |
| sweating asymmetry | sprain | 6-10 years |
| asymmetric edema | sprain | 6-10 years |
| trophic changes | sprain | 6-10 years |
| motor changes | sprain | 6-10 years |
| edema | sprain | 6-10 years |
| dystrophic changes | sprain | 6-10 years |
| skin changes | sprain | 6-10 years |
| nail changes | sprain | 6-10 years |
| hair changes | sprain | 6-10 years |
| motor abnormalities | sprain | 6-10 years |
| hyperesthesia | crush | 6-10 years |
| hyperalgesia | crush | 6-10 years |
| pinprick hyperalgesia | crush | 6-10 years |
| allodynia | crush | 6-10 years |
| temperature asymmetry | crush | 6-10 years |
| skin color asymmetry | crush | 6-10 years |
| sweating asymmetry | crush | 6-10 years |
| asymmetric edema | crush | 6-10 years |
| trophic changes | crush | 6-10 years |
| motor changes | crush | 6-10 years |
| edema | crush | 6-10 years |
| dystrophic changes | crush | 6-10 years |
| skin changes | crush | 6-10 years |
| nail changes | crush | 6-10 years |
| hair changes | crush | 6-10 years |
| motor abnormalities | crush | 6-10 years |
| hyperesthesia | contusion | 6-10 years |
| hyperalgesia | contusion | 6-10 years |
| pinprick hyperalgesia | contusion | 6-10 years |
| allodynia | contusion | 6-10 years |
| temperature asymmetry | contusion | 6-10 years |
| skin color asymmetry | contusion | 6-10 years |
| sweating asymmetry | contusion | 6-10 years |
| asymmetric edema | contusion | 6-10 years |
| trophic changes | contusion | 6-10 years |
| motor changes | contusion | 6-10 years |
| edema | contusion | 6-10 years |
| dystrophic changes | contusion | 6-10 years |
| skin changes | contusion | 6-10 years |
| nail changes | contusion | 6-10 years |
| hair changes | contusion | 6-10 years |
| motor abnormalities | contusion | 6-10 years |
| hyperesthesia | dislocation | 6-10 years |
| hyperalgesia | dislocation | 6-10 years |
| pinprick hyperalgesia | dislocation | 6-10 years |
| allodynia | dislocation | 6-10 years |
| temperature asymmetry | dislocation | 6-10 years |
| skin color asymmetry | dislocation | 6-10 years |
| sweating asymmetry | dislocation | 6-10 years |
| asymmetric edema | dislocation | 6-10 years |
| trophic changes | dislocation | 6-10 years |
| motor changes | dislocation | 6-10 years |
| edema | dislocation | 6-10 years |
| dystrophic changes | dislocation | 6-10 years |
| skin changes | dislocation | 6-10 years |
| nail changes | dislocation | 6-10 years |
| hair changes | dislocation | 6-10 years |
| motor abnormalities | dislocation | 6-10 years |
| hyperesthesia | scratch | 6-10 years |
| hyperalgesia | scratch | 6-10 years |
| pinprick hyperalgesia | scratch | 6-10 years |
| allodynia | scratch | 6-10 years |
| temperature asymmetry | scratch | 6-10 years |
| skin color asymmetry | scratch | 6-10 years |
| sweating asymmetry | scratch | 6-10 years |
| asymmetric edema | scratch | 6-10 years |
| trophic changes | scratch | 6-10 years |
| motor changes | scratch | 6-10 years |
| edema | scratch | 6-10 years |
| dystrophic changes | scratch | 6-10 years |
| skin changes | scratch | 6-10 years |
| nail changes | scratch | 6-10 years |
| hair changes | scratch | 6-10 years |
| motor abnormalities | scratch | 6-10 years |
| hyperesthesia | skin puncture | 6-10 years |
| hyperalgesia | skin puncture | 6-10 years |
| pinprick hyperalgesia | skin puncture | 6-10 years |
| allodynia | skin puncture | 6-10 years |
| temperature asymmetry | skin puncture | 6-10 years |
| skin color asymmetry | skin puncture | 6-10 years |
| sweating asymmetry | skin puncture | 6-10 years |
| asymmetric edema | skin puncture | 6-10 years |
| trophic changes | skin puncture | 6-10 years |
| motor changes | skin puncture | 6-10 years |
| edema | skin puncture | 6-10 years |
| dystrophic changes | skin puncture | 6-10 years |
| skin changes | skin puncture | 6-10 years |
| nail changes | skin puncture | 6-10 years |
| hair changes | skin puncture | 6-10 years |
| motor abnormalities | skin puncture | 6-10 years |

Unless otherwise indicated, any reference to a compound herein, such as neridronic acid, by structure, name, or any other means, includes pharmaceutically acceptable salts, such as the disodium salt; alternate solid forms, such as polymorphs, solvates, hydrates, etc.; tautomers; or any other chemical species that may rapidly convert to a compound described herein under conditions in which the compounds are used as described herein. Unless otherwise indicated, a phrase such as "administering neridronic acid," includes administering any form of neridronic acid, such as those recited above.

In some embodiments, neridronic acid is administered in a dosage form comprising a salt form, such as a salt of a monoanion or neridronic acid (e.g. a monosodium salt or a monopotassium salt), a dianion of neridronic acid (e.g. a disodium or a dipotassium salt), a trianion of neridronic acid (e.g. a trisodium salt or a tripotassium salt), a tetranion (e.g. a tetrasodium salt or a tetrapotassium salt), or a mixture thereof (with respect to cation, valence of the neridronate, or a combination thereof). In some embodiments, neridronic acid is administered in a sodium salt form, such as a monosodium salt, a disodium salt, a trisodium salt, etc. In some circumstances, use of the disodium salt may be desirable. For example, the disodium salt is much more soluble in water than the acid form. As a result, in some processes, the disodium salt can be easier to work with than the acid form. Additionally, the sodium salt may be more bioavailable and/or more rapidly absorbed when taken orally as compared to the acid form.

In some embodiments, neridronic acid may be in the form of a molecular complex. For example, molecular complexes of zoledronic acid include cocrystals, salts, and solvates such as hydrates and mixed solvates of an acid or a salt form, and mixtures containing such materials. Molecular complexes of neridronic acid may be in amorphous forms or polymorphs.

Of particular interest are compositions, or complexes comprising neridronic acid and the standard amino acids or natural existing amino acids, such as alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, valine, etc. Some examples of useful molecular complexes include, but are not limited to, complexes of neridronic acid with sodium cation, ammonium, ammonia, L-lysine, DL-lysine, nicotinamide, adenine, glycine, and selenocysteine.

In some embodiments, neridronic acid may be used to effect a reduction in the levels of pro-inflammatory cytokines in the patient with CRPS. In some embodiments greater pain relief may be obtained in patients with greater baseline levels of pro-inflammatory cytokines when treated with neridronic acid. In some embodiments, greater pain relief may be obtained in patients who experience a reduction or a greater reduction in the levels of pro-inflammatory cytokines when treated with neridronic acid. Pro-inflammatory cytokines include but are not limited to IL-1, IL-2, IL-3, IL-6, IL-8, IL-10, IL-12, tumor necrosis alpha (TNF-alpha), interferon gamma, etc.

The oral bioavailability of neridronic acid may be enhanced by orally administering the neridronic acid in a salt form, such as a disodium salt form In some embodiments, a single dose of the neridronic acid is administered in an amount that results in an AUC of neridronic acid that is about 1,000-2,000 ng·h/mL, about 2,000-3,000 ng·h/mL, about 3,000-4,000 ng·h/mL, about 4,000-5,000 ng·h/mL, about 5,000-6,000 ng·h/mL, about 6,000-7,000 ng·h/mL, about 7,000-8,000 ng·h/mL, about 8,000-9,000 ng·h/mL, about 9,000-10,000 ng·h/mL, about 10,000-11,000 ng·h/mL, about 11,000-12,000 ng·h/mL, about 12,000-13,000 ng·h/mL, about 13,000-14,000 ng·h/mL, about 14,000-15,000 ng·h/mL, about 15,000-16,000 ng·h/mL, about 16,000-17,000 ng·h/mL, about 17,000-18,000 ng·h/mL, about 18,000-19,000 ng·h/mL, about 19,000-20,000 ng·h/mL, about 20,000-21,000 ng·h/mL, about 21,000-22,000 ng·h/mL, about 22,000-23,000 ng·h/mL, about 23,000-24,000 ng·h/mL, about 24,000-25,000 ng·h/mL, about 25,000-26,000 ng·h/mL, about 26,000-27,000 ng·h/mL, about 27,000-28,000 ng·h/mL, about 28,000-29,000 ng·h/mL, about 29,000-30,000 ng·h/mL, about 1,000-5,000 ng·h/mL, about 5,000-10,000 ng·h/mL, about 10,000-15,000 ng·h/mL, about 15,000-20,000 ng·h/mL, about 20,000-25,000 ng·h/mL, about 25,000-30,000 ng·h/mL, about 1,000-10,000 ng·h/mL, about 10,000-20,000 ng·h/mL, about 20,000-30,000 ng·h/mL, about 1,000-15,000 ng·h/mL, about 15,000-30,000 ng·h/mL, or about 1,000-30,000 ng·h/mL.

Unless otherwise indicated, the AUC refers to the AUC calculated to the last measured concentration ($AUC_{(0-t)}$) and extrapolated to infinity ($AUC_{(0-inf)}$).

In some embodiments, molecular complex comprising neridronic acid is administered in an amount that results in an AUC of neridronic acid, measured over the entire course of treatment, of about 10,000-30,000 ng·h/mL about 30,000-100,000 ng·h/mL about 30,000-50,000 ng·h/mL, about 30,000-40,000 ng·h/mL, about 40,000-50,000 ng·h/mL, about 50,000-60,000 ng·h/mL, about 60,000-70,000 ng·h/mL, about 50,000-70,000 ng·h/mL, about 70,000-80,000 ng·h/mL, about 80,000-90,000 ng·h/mL, about 90,000-100,000 ng·h/mL, about 70,000-100,000 ng·h/mL, about 100,000-200,0000 ng·h/mL, about 200,000-300,0000 ng·h/mL, about 300,000-400,0000 ng·h/mL, about 400,000-500,0000 ng·h/mL, or any AUC in a range bounded by any of these values.

In some embodiments, neridronic acid is administered at an interval of about every 1, 2, 3, 4, 5, 6, 7, 8, 9, 10, 11, 12, 13, or 14 days; or 15, 16, 17, 18, 19, 20, or 21 days; or 22, 23, 24, 25, 26, 27, 28, 29, 30, or 31 days; or 32, 33, 34, 35, 36, 37, 38, 39, 40, 41, 42, 43, 44, or 45; or 46, 47, 48, 49, 50, 51, 52, 53, 54, 55, 56, 57, 58, 59, or 60 days; or 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90 days; or 91, 92, 93, 94, 95, 96, 97, 98, 99, 100, 101, 102, 103, 104, 105, 106, 107, 108, 109, 110, 111, 112, 113, 114, 115, 116, 117, 118, 119, or 120 days.

The C-terminal telopeptide (CTX) is one of the products from type I collagen degradation by osteoclasts during bone resorption. Thus, CTX serum levels may be used as a biomarker to indicate and monitor bone breakdown, resorption, and loss. In some embodiments, neridronic acid may be used to inhibit osteoclast activity and/or lower CTX serum levels in a human CRPS patient, for example, by at least about 5%, at least about 10%, at least about 15%, at least about 20%, at least about 25%, at least about 30%, at least about 35%, at least about 40%, at least about 45%, at least about 50%, at least about 55%, at least about 60%, at least about 70%, at least about 75%, at least about 80%, at least about 85%, at least about 90%, at least about 95%, at least about 99%, at least about 100%, about 60%-70%, about 70%-80%, about 80%-90%, about 85-95%, about 80%-85%, about 85%-90%, about 90%-95%, or any other reduction in osteoclast activity or CTX serum levels in a range bounded by, or between, any of these values.

In some embodiments, treating a human CRPS patient with neridronic acid may result in lower serum alkaline phosphatase (ALP) levels. For example, the reduction of ALP levels by at least about 20%, at least about 40%, at least about 50%, at least about 60%, at least about 80%, about 50-60%, about 60-80%, about 80-90%, about 90-95%, or any other reduction in ALP levels in a range bounded by, or between, any of these values from baseline, within 12 months, 18 months, or up to at least 5 years from the time of the last oral administration of zoledronic acid or other bisphosphonates.

Neridronic acid or another bisphosphonate may be combined with a pharmaceutical carrier selected on the basis of the chosen route of administration and standard pharmaceutical practice as described, for example, in Remington's Pharmaceutical Sciences, 2005, the disclosure of which is hereby incorporated herein by reference, in its entirety. The relative proportions of active ingredient and carrier may be determined, for example, by the solubility and chemical nature of the compounds, chosen route of administration and standard pharmaceutical practice.

Neridronic acid or another bisphosphonate may be administered by any means that may result in the contact of the active agent(s) with the desired site or site(s) of action in the body of a patient. The compounds may be administered by any conventional means available for use in conjunction with pharmaceuticals, either as individual therapeutic agents or in a combination of therapeutic agents. For example, they may be administered as the sole active agents in a pharmaceutical composition, or they can be used in combination with other therapeutically active ingredients.

Neridronic acid or another bisphosphonate may be administered to a human patient in a variety of forms adapted to the chosen route of administration, e.g., orally, rectally, or parenterally. Parenteral administration in this respect includes, but is not limited to, administration by the following routes: pulmonary, intrathecal, intravenous, intramuscular, subcutaneous, intraocular, intrasynovial, transepithelial including transdermal, sublingual and buccal; topically; nasal inhalation via insufflation; and rectal systemic.

The effective amount of neridronic acid or another bisphosphonate will vary depending on various factors known to the treating physicians, such as the severity of the condition to be treated, route of administration, formulation and dosage forms, physical characteristics of the bisphosphonate compound used, and age, weight and response of the individual patients.

Any suitable dose of neridronic acid may be administered to a human CRPS patient. For intravenous administration, a single dose may contain about 20-200 mg, about 50-150 mg, about 20-30 mg, about 30-40 mg, about 40-50 mg, about 50-60 mg, about 60-70 mg, about 70-80 mg, about 80-90 mg, about 90-100 mg, about 100-110 mg, about 110-120 mg, about 120-130 mg, about 130-140 mg, about 140-150 mg, about 50-100 mg, about 100-150 mg, about 50-80 mg, about 80-120 mg, about 120-150 mg, about 62.5 mg, or about 100 mg of neridronic acid. The dose may be repeated once, twice, three times, four times, five times, six times, seven times, eight times, nine times, 10 times, or possibly more, for a total dose of about 20-2000 mg, about 20-100 mg, about 100-200 mg, about 200-300 mg, about 300-400 mg, about 400-500 mg, about 500-600 mg, about 600-700 mg, about 700-800 mg, about 800-900 mg, about 900-1,000 mg, about 1,000-1,100 mg, about 1,100-1,200 mg, about 1,200-1,300 mg, about 1,300-1,400 mg, about 1,400-1,500 mg, about 1,500-1,600 mg, about 1,600-1,700 mg, about 1,700-1,800 mg, about 1,800 mg-1,900 mg, about 1,800-1,900 mg, about 1,900-2,000 mg, about 300-500 mg, about 100-500 mg, about 500-1,000 mg, about 1,000-1,500 mg, or about 1,500-2,000 mg of neridronic acid.

In some embodiments, the neridronic acid is administered to human beings by 4 intravenous infusions within 10 Days. In some embodiments, the neridronic acid is administered to human beings by 8 intravenous infusions within 52 weeks. In some embodiments, the neridronic acid is administered to human beings by 4 intravenous infusions within 10 days in a first period of 26 weeks, followed by 4 additional intravenous infusions within 10 days in a second period of total 52 weeks.

For oral administration to a human CRPS patient, a single dose may contain about 1-20 mg, about 20-40 mg, about 40-60 mg, about 60-80 mg, about 80-100 mg, about 100-120 mg, about 120-140 mg, about 140-160 mg, about 160-180 mg, about 180-200 mg, about 200-250 mg, about 250-300 mg, about 300-350 mg, about 350-400 mg, about 400-500 mg, about 500-600 mg, about 600-700 mg, about 700-800 mg, about 800-1,000 mg, about 100-200 mg, about 200-300 mg, about 300-400 mg, about 200-500 mg, about 500-800 mg, or about 800-1,000 mg of neridronic acid. The dose may be repeated once, twice, three times, four times, five times, six times, seven times, eight times, nine times, 10 times, 11 times, 12 times, 13 times, 14 times, 15 times, 16 times, 17 times, 18 times, 19 times, 20 times, 21 times, 22 times, 23 times, 24 times, 25 times, 26 times, 27 times, 28 times, 29 times, 30 times, 31 times, 32 times, 33 times, 34 times, 35 times, 36 times, 37 times, 38 times, 39 times, 40 times, 41 times, 42 times, 43 times, 44 times, 45 times, 46 times, 47 times, 48 times, 49 times, 50 times, 51 times, 52 times, 53 times, 54 times, 55 times, 56 times, 57 times, 58 times, 59 times, 60 times, 61 times, 62 times, 63 times, 64 times, 65 times, 66 times, 67 times, 68 times, 69 times, 70 times, 71 times, 72 times, 73 times, 74 times, 75 times, 76 times, 77 times, 78 times, 79 times, 80 times, 81 times, 82 times, 83 times, 84 times, 85 times, 86 times, 87 times, 88 times, 89 times, or 90 times, or possibly more. The dose may be repeated at an interval of one day, about two days, about three days, about four days, about five days, about six days, about seven days, about eight days, about nine days, about 10 days, about 11 days, about 12 days, about 13 days, about 14 days, about 15 days, about 16 days, about 17 days, about 18 days, about 19 days, about 20 days, about 21 days, about 22 days, about 23 days, about 24 days, about 25 days, about 26 days, about 27 days, about 28 days, about 29 days, about 30 days, about 30, about 31 days, approximately monthly, about two months, about three months, about four months, about five months, about six months, about yearly, etc. The total dose may be about 4,000-5,000 mg, about 5,000-6,000 mg, about 6,000-7,000 mg, about 7,000-8,000 mg, about 8,000-9,000 mg, about 9,000-10,000 mg, about 10,000-11,000 mg, about 11,000-12,000 mg, about 12,000-13,000 mg, about 13,000-14,000 mg, about 14,000-15,000 mg, about 15,000-16,000 mg, about 16,000-17,000 mg, about 17,000-18,000 mg, about 18,000-19,000 mg, about 19,000-20,000 mg, about 20,000-21,000 mg, about 21,000-22,000 mg, about 22,000-23,000 mg, about 23,000-24,000 mg, about 24,000-25,000, about mg 25,000-26,000 mg, about 26,000-27,000 mg, about 27,000-28,000 mg, about 28,000-29,000 mg, about 29,000-30,000 mg, about 30,000-31,000 mg, about 31,000-32,000 mg, about 32,000-33,000 mg, about 33,000-34,000 mg, about 34,000-35,000 mg, about 35,000-36,000 mg, about 36,000-37,000 mg, about 37,000-38,000 mg, about 38,000-39,000 mg, about 39,000-40,000 mg, about 4,000-10,000 mg, about 10,000-15,000 mg, about 15,000-20,000 mg, about 20,000-25,000 mg, about 25,000-30,000 mg, about 30,000-35,000 mg, about 35,000-40,000 mg, about 10,000-20,000 mg, about 20,000-30,000 mg, about 30,000-40,000 mg, about 4,000-15,000 mg, or about 15,000-30,000 mg of neridronic acid.

With respect to oral administration of neridronic acid, for the treatment of CRPS, or any other condition recited herein, it may helpful if the mammal or human being to which the osteoclast inhibitor is administered does not eat food or drink beverage, (other than any water required to swallow the oral dosage form) for at least about 1 hour, at least about 2 hours, at least about 4 hours, at least about 6 hours, at least about 8 hours, at least about 10 hours, or at least about 12 hours before the osteoclast inhibitor is administered. It may also be helpful if the mammal or human being to which the osteoclast inhibitor is administered does not eat food or drink beverage for at least about 30 minutes, at least about 1 hour, at least about 2 hours, at least about 3 hours, or at least about 4 hours after the osteoclast inhibitor is administered. In some embodiments, a human being to which the zoledronic acid is administered avoids lying down, or remains upright or sits upright, for at least about 30 minutes or about 1 hour after receiving a dosage form containing the osteoclast inhibitor. Avoiding food or beverage before or after oral administration of the osteoclast inhibitor can improve the bioavailability of the osteoclast inhibitor.

Neridronic acid, may be formulated for oral administration, for example, with an inert diluent or with an edible carrier, or it may be enclosed in hard or soft shell gelatin capsules, compressed into tablets, or incorporated directly with the food of the diet. For oral therapeutic administration, the active compound may be incorporated with an excipient and used in the form of ingestible tablets, buccal tablets, coated tablets, troches, capsules, elixirs, dispersions, suspensions, solutions, syrups, wafers, patches, and the like.

Tablets, troches, pills, capsules and the like may also contain one or more of the following: a binder such as gum tragacanth, acacia, corn starch or gelatin; an excipient, such as dicalcium phosphate; a disintegrating agent such as corn starch, potato starch, alginic acid and the like; a lubricant such as magnesium stearate; a sweetening agent such as sucrose, lactose or saccharin; or a flavoring agent such as peppermint, oil of wintergreen or cherry flavoring. When the unit dosage form is a capsule, it may contain, in addition to materials of the above type, a liquid carrier. Various other materials may be present as coating, for instance, tablets, pills, or capsules may be coated with shellac, sugar or both. A syrup or elixir may contain the active compound, sucrose as a sweetening agent, methyl and propylparabens as preservatives, a dye and flavoring, such as cherry or orange flavor. It may be desirable for material in a dosage form or pharmaceutical composition to be pharmaceutically pure and substantially non-toxic in the amounts employed.
Example of a Product Kit Including Product Label Information One example of a product kit including product labeling information is described below, which is not to be construed as limitations.

A product kit contains the following dosage forms.

(1) Neridronate 25 mg Solution for Injection:

This dosage form is in a solution in a 2 ml vial comprising 27 mg of sodium neridronate, which is molar equivalent to 25 mg of neridronic acid; sodium chloride; sodium citrate dihydrate, citric acid monohydrate; and water, and is for injections. This dosage form also contains 417.74 mmol (or 9.6 mg) of sodium per dose. This dosage form is a clear and colorless solution for injection in 1×2 mL vial for intramuscular and intravenous use.

(2) Neridronate 100 mg Concentrate for Solution for Infusion:

This dosage form is in a solution in an 8 ml vial comprising 108 mg of sodium neridronate, which is molar equivalent to 100 mg of neridronic acid; sodium chloride; sodium citrate dehydrate; citric acid monohydrate; and water for injections. This dosage form also contains 1670.98 mmol (or 38.42 mg) of sodium per dose. This dosage form is a clear and colorless solution in a pack of 2 vials of 8 mL for intravenous use.

The dosage form comprising neridronic acid is used in adults and children under 18 years of age for treatment of CRPS and an inherited disease characterized by fragility of the skeleton, a decrease in bone mass and a predisposition to fractures (osteogenesis imperfecta or "glass bones disease").

The dosage form comprising neridronic acid is also used in adults for treatment of a bone disease that causes enlargement and deformation (Paget's bone disease); and a bone disease characterized by pain and swelling, reduction of bone mass, movement disorders, stiffness of the joints, abnormal constriction or dilatation of blood vessels, soft tissue degeneration (algodystrophy).

This medicine can be given either to adults for injection in a muscle or in a vein, and to children only by injection into a vein.

A patient is advised not to take the dosage forms containing neridronic acid if the patient has any one of the following conditions: (1) the patient is allergic to neridronic acid, a bisphosphonate, or any of the other ingredients of in the dosage form (listed below); (2) the patient suffers from severe kidney disease (severe renal failure); and (3) the patient is breastfeeding (see below).

A patient is advised to notify the doctor before taking the dosage forms containing neridronic acid if the patient (1) have been diagnosed with a tumor and are taking bisphosphonates, medicines to treat bone disease; (2) undergoes chemotherapy or radiotherapy sessions to treat tumors; (3) are taking medicines to treat inflammation (corticosteroids); (4) suffers from fragile bones (osteoporosis); (5) has a poor dental health condition, has a gum disease, has a dental extraction; (6) is using, have recently used any other medicines; (7) is taking aminoglycosides used to treat infections; or (8) is pregnant. In these cases a disease known as osteonecrosis of the jaw could develop. In this case, during treatment with neridronic acid, avoid, if possible, undergoing invasive dental procedures. It may also be necessary that the patient undergo preventive dental treatment before starting treatment with this dosage form containing neridronic acid.

The effective dose amount varies for different disease, age, body weight, and etc. The recommended dose amounts for different diseases, ages and body weights are listed below.

For an adult patient at least 18 years of age who has Osteogenesis imperfecta, the recommended dose ranges from 25 mg to 100 mg intravenously, depending on body weight, in a single administration by slow infusion, after diluted in 250-500 mL of 0.9% sodium chloride solution. The approximate dosage is 2 mg/kg of body weight every 3 months. The total dose can be divided into 25-mg intramuscular doses for up to 4 consecutive days every 3 months.

For a patient under 18 years of age who has Osteogenesis imperfecta, the recommended dose is 2 mg/kg body weight (with maximum dose of 100 mg) after diluted in 250-500 mL of 0.9% sodium chloride solution, by slow intravenous infusion (for at least 2 hours) every 3 months.

For a patient who has Paget's bone disease, the most commonly recommended dose is 100 mg per day intravenously, for 2 consecutive days, by slow infusion (for at least 2 hours) after diluted in 250-500 mL of saline solution. Lower doses may be sufficient for less severe forms of the disease. The total dose can also be fractionated into intramuscular doses of 25 mg/day to be administered on consecutive days up to a maximum of 8 days. The dose cycle can be repeated after at least 6 months, when the therapeutic effect on the bone turnover (serum alkaline phosphatasemia) of the first cycle is fully expressed.

For a patient who has Complex Regional Pain Syndrome, the recommended dose is 100 mg daily intravenously, every 3 days for a total of 400 mg of neridronate, given as a slow intravenous infusion (for at least 2 hours) after diluted in 250-500 ml of saline solution.

The symptoms of overdose may consist of lowering blood calcium levels. Significant lowering of calcium levels in the blood can be corrected by intravenous administration of calcium gluconate. A patient is advised to contact a doctor or go to a nearest hospital immediately if too much of the dosage form is taken. It is advised not to take a double dose to make up for a forgotten dose.

Possible side effects include increase body temperature; Influenza-like syndrome with fever, malaise, chills and pain in the bones and/or muscles, in which cases no specific treatment is needed and the symptoms disappear within a few hours or days; lowering calcium levels in the blood;

lowering levels of phosphate in the blood; skin rash; hives; dizziness; pain at the injection site, which decreases after a few minutes (when administered in a muscle; atypical fracture of the femur (long leg bone), particularly in patients who have long been treated with the dosage form comprising neridronic acid for osteoporosis; inflammation to the eyes such as eye pain, redness, intolerance to light, tearing, visual fog, secretion (conjunctivitis, anterior uveitis, episcleritis); and/or although very rare, ear pain, ear secretions and/or ear infection, and which could be signs of bone damage to the ear.

The dosage forms in the kit does not require any special storage conditions, but must keep out of the sight and reach of children. It is advised not to use the dosage form after the expiration date which refers to the last day of that month, and not to throw away any remaining dosage forms via wastewater or household waste to protect environment.

In example 1 below, zoledronic acid was administered in the disodium salt form as disodium zoledronate tetrahydrate. No bioavailability enhancing agents were used in the test compositions. It is believed that the test for zoledronic acid is applicable to neridronic acid.

Example 1. Treatment of Complex Regional Pain Syndrome with Orally Administered Zoledronic Acid The effect of orally administered zoledronic acid was examined in the rat tibia fracture model of complex regional pain syndrome (CRPS). CRPS was induced in the rats by fracturing the right distal tibias of the animals and casting the fractured hindpaws for 4 weeks, as described in Guo T Z et al. (Pain. 2004; 108: 95-107). This animal model has been shown to replicate the inciting trauma (such as a fracture, a surgery, a crushing injury, a cutting injury, a scratch, or a puncture injury), natural history, signs, symptoms, and pathologic changes observed in human CRPS patients (Kingery W S et al., Pain. 2003; 104:75-84).

Animals were orally administered either vehicle (control) or zoledronic acid, in a dosage of 18 mg/m$^2$/day (3 mg/kg/day) for 28 days, starting on the day of fracture and casting. Drug was dissolved in distilled water and administered by gavage. Animals were fasted for 4 hours before and 2 hours after dosing. At the end of the 28-day period, casts were removed, and on the following day, the rats were tested for hindpaw pain, edema, and warmth.

Pain Assessments

Pain was assessed by measuring hyperalgesia, and weight bearing.

To measure hyperalgesia, an up-down von Frey testing paradigm was used. Rats were placed in a clear plastic cylinder (20 cm in diameter) with a wire mesh bottom and allowed to acclimate for 15 minutes. The paw was tested with one of a series of eight von Frey hairs ranging in stiffness from 0.41 g to 15.14 g. The von Frey hair was applied against the hindpaw plantar skin at approximately midsole, taking care to avoid the tori pads. The fiber was pushed until it slightly bowed and then it was jiggled in that position for 6 seconds. Stimuli were presented at an interval of several seconds. Hindpaw withdrawal from the fiber was considered a positive response. The initial fiber presentation was 2.1 g and the fibers were presented according to the up-down method of Dixon to generate six responses in the immediate vicinity of the 50% threshold. Stimuli were presented at an interval of several seconds.

An incapacitance device (IITC Inc. Life Science, Woodland, Calif., USA) was used to measure hindpaw weight bearing, a postural effect of pain. The rats were manually held in a vertical position over the apparatus with the hindpaws resting on separate metal scale plates and the entire weight of the rat was supported on the hindpaws. The duration of each measurement was 6 seconds and 10 consecutive measurements were taken at 60-second intervals. Eight readings (excluding the highest and lowest ones) were averaged to calculate the bilateral hindpaw weight-bearing values. Weight bearing data were analyzed as the ratio between right (fracture) and left hindpaw weight bearing values ((2R/(R+L))×100%).

Edema Assessment

A laser sensor technique was used to determine the dorsal-ventral thickness of the hindpaw. Before baseline testing the bilateral hindpaws were tattooed with a 2 to 3 mm spot on the dorsal skin over the midpoint of the third metatarsal. For laser measurements each rat was briefly anesthetized with isoflurane and then held vertically so the hindpaw rested on a table top below the laser. The paw was gently held flat on the table with a small metal rod applied to the top of the ankle joint. Using optical triangulation, a laser with a distance measuring sensor was used to determine the distance to the table top and to the top of the hindpaw at the tattoo site and the difference was used to calculate the dorsal-ventral paw thickness. The measurement sensor device used in these experiments (4381 Precicura, Limab, Goteborg, Sweden) has a measurement range of 200 mm with a 0.01 mm resolution.

Hindpaw Temperature Measurement

The temperature of the hindpaw was measured using a fine wire thermocouple (Omega, Stanford, Conn., USA) applied to the paw skin. Six sites were tested per hindpaw. The six measurements for each hindpaw were averaged for the mean temperature.

Results

As illustrated in FIG. 1, treatment with orally administered zoledronic acid reversed pain, restored weight bearing, and prevented edema as compared to vehicle treated animals.

Figure 2:
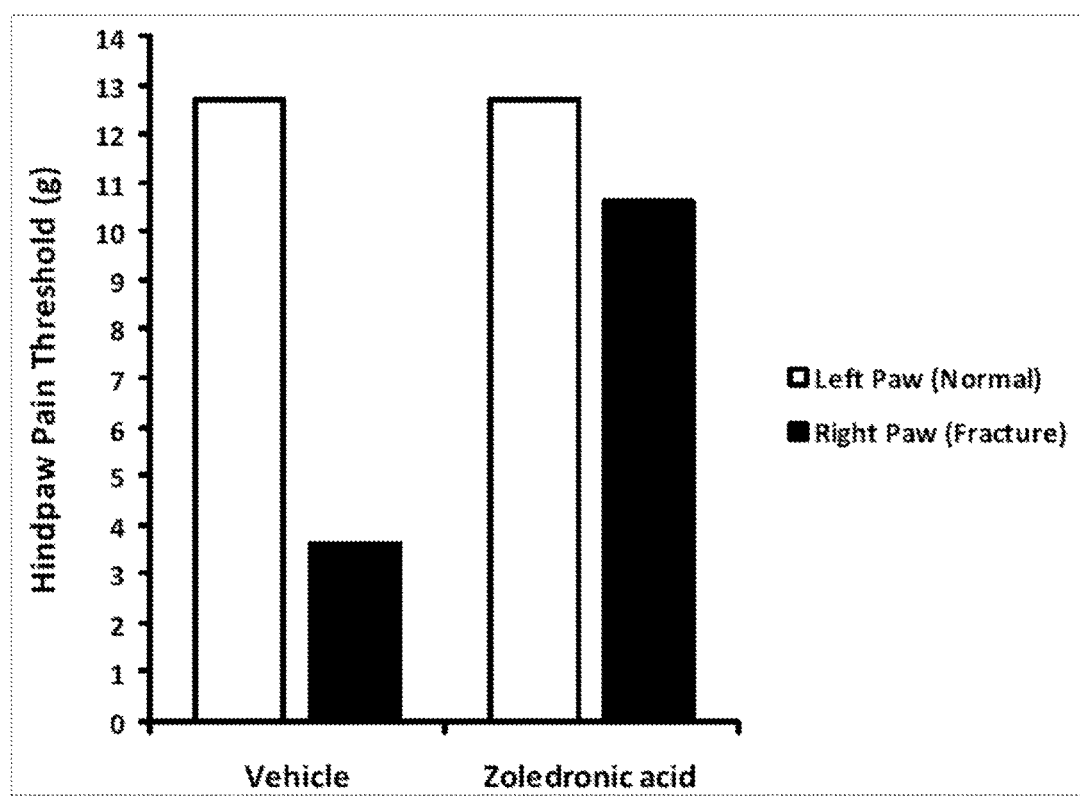
FIG. 2 depicts hindpaw pain thresholds for vehicle and zoledronic acid treated rats in a rat model of complex regional pain syndrome.

As illustrated in FIG. 2, von Frey pain thresholds for the right (fracture) hindpaw were reduced by 72% versus the contralateral (normal) hindpaw in vehicle treated animals. Zoledronate treatment reversed fracture induced pain by 77% as compared to vehicle treatment.

Figure 3:
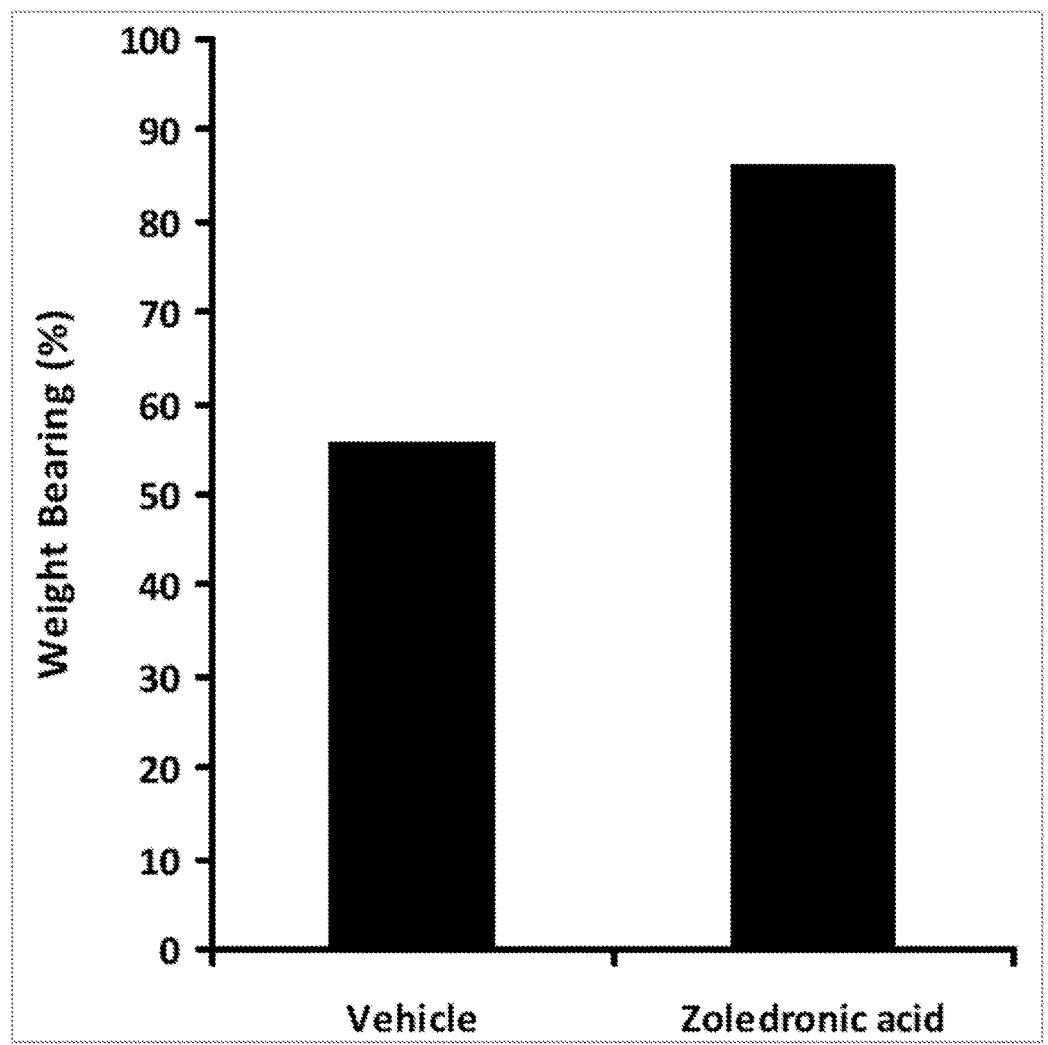
FIG. 3 depicts weight bearing for vehicle and zoledronic acid treated rats in a rat model of complex regional pain syndrome.

As illustrated in FIG. 3, reduction in weight bearing, a postural effect of pain, was significantly higher in the vehicle treated group as compared to the zoledronic acid treated group. Weight bearing on the fracture hindlimb was reduced to 55% of normal in the vehicle treated group. Zoledronate treatment significantly restored hindlimb weight bearing as compared to vehicle treatment (86% of normal).

Figure 4:
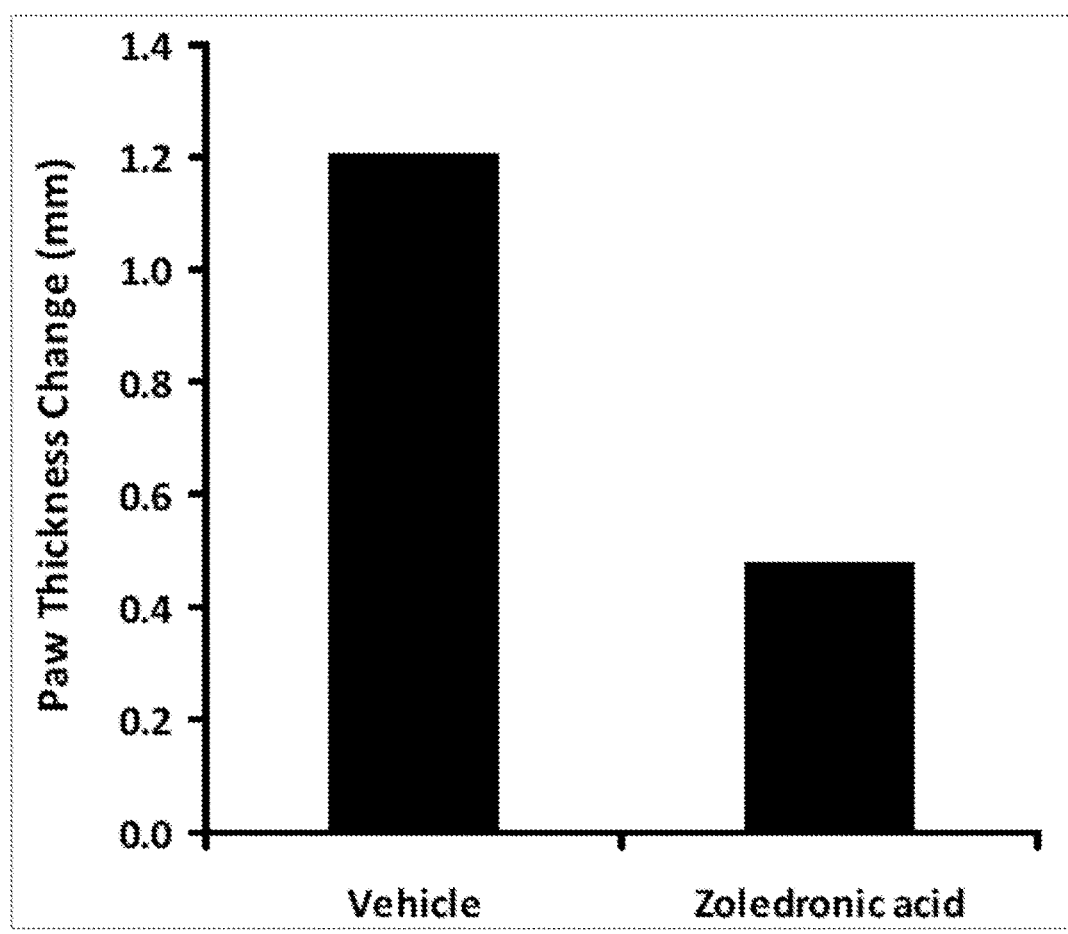
FIG. 4 depicts paw thickness change for vehicle and zoledronic acid treated rats in a rat model of complex regional pain syndrome.

As illustrated in FIG. 4, the expected increase in hindpaw thickness was greater in the vehicle treated group as compared to the zoledronic acid treated group, reflecting the development of edema. Zoledronate treatment reduced hindpaw edema by 60% versus vehicle treatment.

Zoledronic acid reduced hindpaw warmth by 5% versus vehicle treatment.

The daily dose in the above experiment was 18 mg/m$^2$/day. Under current FDA guidelines, the reference body surface area of a human adult is 1.62 m$^2$. Thus, a daily dose of 18 mg/m$^2$ corresponds to a monthly dose of about 500-560 mg/m$^2$ or a human dose of about 800-900 mg.

The following embodiments are contemplated:

Embodiment 1

A method of treating pain in a human being suffering from complex regional pain syndrome (CRPS) comprising administering neridronic acid in an acid form or a salt form to the human being with the result that the human being experiences pain relief as a result of receiving the neridronic acid.

Embodiment 2

A method of treating pain in a human being suffering from complex regional pain syndrome (CRPS) and back pain comprising administering neridronic acid in an acid form or a salt form to the human being with the result that the human being experiences pain relief as a result of receiving the neridronic acid.

Embodiment 3

A method of treating pain in a human being suffering from complex regional pain syndrome and arthritis comprising administering neridronic acid in an acid form or a salt form to the human being with the result that the human being experiences pain relief as a result of receiving the neridronic acid.

Embodiment 4

A method of treating pain in a human being suffering from complex regional pain syndrome and osteoarthritis comprising administering neridronic acid in an acid form or a salt form to the human being with the result that the human being experiences pain relief as a result of receiving the neridronic acid.

Embodiment 5

A method of treating pain in a human being suffering from complex regional pain syndrome and headache comprising administering neridronic acid in an acid form or a salt form to the human being with the result that the human being experiences pain relief as a result of receiving the neridronic acid.

Embodiment 6

A method of treating pain in a human being suffering from complex regional pain syndrome and migraine comprising administering neridronic acid in an acid form or a salt form to the human being with the result that the human being experiences pain relief as a result of receiving the neridronic acid.

Embodiment 7

The method of embodiment 1, 2, 3, 4, 5, or 6, wherein the CRPS is CRPS Type-I.

Embodiment 8

The method of embodiment 1, 2, 3, 4, 5, or 6, wherein the CRPS is CRPS Type-II.

Embodiment 9

The method of embodiment 1, 2, 3, 4, 5, or 6, wherein the CRPS is warm CRPS.

Embodiment 10

The method of embodiment 1, 2, 3, 4, 5, or 6, wherein the CRPS is cold CRPS.

Embodiment 11

The method of embodiment 1, 2, 3, 4, 5, or 6, wherein the CRPS is triggered by a traumatic event.

Embodiment 12

The method of embodiment 11, wherein the traumatic event is fracture.

Embodiment 13

The method of embodiment 11, wherein the traumatic event is surgery.

Embodiment 14

The method of embodiment 11, wherein the traumatic event is a soft tissue injury.

Embodiment 15

The method of embodiment 11, wherein the traumatic event is a bone injury.

Embodiment 16

The method of embodiment 11, wherein the traumatic event is a nerve injury.

Embodiment 17

The method of embodiment 11, wherein the traumatic event is a sprain.

Embodiment 18

The method of embodiment 11, wherein the traumatic event is a crush.

Embodiment 19

The method of embodiment 11, wherein the traumatic event is a contusion.

Embodiment 20

The method of embodiment 11, wherein the traumatic event is a dislocation.

Embodiment 21

The method of embodiment 11, wherein the traumatic event is a scratch.

Embodiment 22

The method of embodiment 11, wherein the traumatic event is a skin puncture.

Embodiment 23

The method of embodiment 1, 2, 3, 4, 5, 6, 7, 8, 9, 10, 11, 12, 13, 14, 15, 16, 17, 18, 19, 20, 21, or 22, wherein, on the day before the neridronic acid is first administered, the human being has an average pain intensity score of at least 4 on the 0-10 NRS.

Embodiment 24

The method of embodiment 23, wherein, on the day before the neridronic acid is first administered, the human being has an average pain intensity score of at least 5 on the 0-10 NRS.

Embodiment 25

The method of embodiment 23, wherein, on the day before the neridronic acid is first administered, the human being has an average pain intensity score of at least 6 on the 0-10 NRS.

Embodiment 26

The method of embodiment 23, wherein, on the day before the neridronic acid is first administered, the human being has an average pain intensity score of at least 7 on the 0-10 NRS.

Embodiment 27

The method of embodiment 23, wherein, on the day before the neridronic acid is first administered, the human being has an average pain intensity score of at least 8 on the 0-10 NRS.

Embodiment 28

The method of embodiment 23, wherein, on the day before the neridronic acid is first administered, the human being has an average pain intensity score of at least 9 on the 0-10 NRS.

Embodiment 29

The method of embodiment 1, 2, 3, 4, 5, 6, 7, 8, 9, 10, 11, 12, 13, 14, 15, 16, 17, 18, 19, 20, 21, 22, 23, 24, 25, 26, 27, or 28, wherein at 12 weeks from the first day that the neridronic acid is administered to the human being, the human being has an average pain intensity score that is at least about 10% lower than it was at baseline.

Embodiment 30

The method of embodiment 29, wherein at 12 weeks from the first day that the neridronic acid is administered to the human being, the human being has an average pain intensity score that is at least about 30% lower than it was at baseline.

Embodiment 31

The method of embodiment 29, wherein at 12 weeks from the first day that the neridronic acid is administered to the human being, the human being has an average pain intensity score that is at least about 50% lower than it was at baseline.

Embodiment 32

The method of embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31, wherein the human being has suffered from the CRPS for less than 2 years on the first day that the neridronic acid is administered to the human being.

Embodiment 33

The method of embodiment 32, wherein the human being has suffered from the CRPS for about 1 day to about 4 months on the first day that the neridronic acid is administered to the human being.

Embodiment 34

The method of embodiment 32, wherein the human being has suffered from the CRPS for about 4 months to about 8 months on the first day that the neridronic acid is administered to the human being.

Embodiment 35

The method of embodiment 32, wherein the human being has suffered from the CRPS for about 8 months to about 12 months on the first day that the neridronic acid is administered to the human being.

Embodiment 36

The method of embodiment 32, wherein the human being has suffered from the CRPS for about 1 year to about 2 years on the first day that the neridronic acid is administered to the human being.

Embodiment 37

The method of embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31, wherein the human being has suffered from the CRPS for about 2 years to about 4 years on the first day that the neridronic acid is administered to the human being.

Embodiment 38

The method of embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31, wherein the human being has suffered from the CRPS for about 4 years to about 6 years on the first day that the neridronic acid is administered to the human being.

Embodiment 39

The method of embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31, wherein the human being has suffered from the CRPS for about 6 years to about 10 years on the first day that the neridronic acid is administered to the human being.

Embodiment 40

The method of embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, or 39, wherein the human being is selected for having hyperesthesia as a symptom of the CRPS.

Embodiment 41

The method of embodiment 1, 2, 3, 4, 5, 6, 7, 8, 9, 10, 11, 12, 13, 14, 15, 16, 17, 18, 19, 20, 21, 22, 23, 24, 25, 26, 27,

Embodiment 42

The method of embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, or 39, wherein the human being is selected for having hyperalgesia as a symptom of the CRPS.

Embodiment 42

The method of embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, or 39, wherein the human being is selected for having pinprick hyperalgesia as a symptom of the CRPS.

Embodiment 43

The method of embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, or 39, wherein the human being is selected for having allodynia as a symptom of the CRPS.

Embodiment 44

The method of embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, or 39, wherein the human being is selected for having temperature asymmetry as a symptom of the CRPS.

Embodiment 45

The method of embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, or 39, wherein the human being is selected for having skin color asymmetry as a symptom of the CRPS.

Embodiment 46

The method of embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, or 39, wherein the human being is selected for having sweating asymmetry as a symptom of the CRPS.

Embodiment 47

The method of embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, or 39, wherein the human being is selected for having asymmetric edema as a symptom of the CRPS.

Embodiment 48

The method of embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, or 39, wherein the human being is selected for having trophic changes as a symptom of the CRPS.

Embodiment 49

The method of embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, or 39, wherein the human being is selected for having motor changes as a symptom of the CRPS.

Embodiment 50

The method of embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, or 39, wherein the human being is selected for having edema as a symptom of the CRPS.

Embodiment 51

The method of embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, or 39, wherein the human being is selected for having dystrophic changes as a symptom of the CRPS.

Embodiment 52

The method of embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, or 39, wherein the human being is selected for having skin changes as a symptom of the CRPS.

Embodiment 53

The method of embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, or 39, wherein the human being is selected for having nail changes as a symptom of the CRPS.

Embodiment 54

The method of embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, or 39, wherein the human being is selected for having hair changes as a symptom of the CRPS.

Embodiment 55

The method of embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, or 39, wherein the human being is selected for having motor abnormalities as a symptom of the CRPS.

Embodiment 56

The method of embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, or 55, wherein the human being also suffers from depression (including moderate depression or severe depression).

Embodiment 57

The method of embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, or 55, wherein the human being also suffers from anxiety.

Embodiment 58

The method of embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, or 55, wherein the human being also suffers from insomnia.

Unless otherwise indicated, all numbers expressing quantities of ingredients, properties such as molecular weight, reaction conditions, and so forth used in the specification and claims are to be understood in all instances as indicating both the exact values as shown and as being modified by the term "about." Accordingly, unless indicated to the contrary, the numerical parameters set forth in the specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

The terms "a," "an," "the" and similar referents used in the context of describing the invention (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of any claim. No language in the specification should be construed as indicating any non-claimed element essential to the practice of the invention.

Groupings of alternative elements or embodiments disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, the claims include all modifications and equivalents of the subject matter recited in the claims as permitted by applicable law. Moreover, any combination of the above-described elements in all possible variations thereof is contemplated unless otherwise indicated herein or otherwise clearly contradicted by context.

In closing, it is to be understood that the embodiments disclosed herein are illustrative of the principles of the claims. Other modifications that may be employed are within the scope of the claims. Thus, by way of example, but not of limitation, alternative embodiments may be utilized in accordance with the teachings herein. Accordingly, the claims are not limited to embodiments precisely as shown and described.

The invention claimed is:

1. A method of treating pain in a human being suffering from complex regional pain syndrome (CRPS) and insomnia comprising administering, in one or more individual intravenous doses for a total amount of about 20 mg to about 2000 mg of neridronic acid, in an acid form or a salt form, or in one or more individual oral doses for a total amount of about 4000 mg to about 40,000 mg of neridronic acid, in the acid form or the salt form, to the human being suffering from CRPS and insomnia, with the result that 12 weeks from the first day that the neridronic acid is administered to the human being, the human being has an average pain intensity score, according to the 0-10 numerical rating scale (NRS), that is at least about 10% lower than the average pain intensity score at baseline.

2. The method of claim 1, wherein the CRPS is CRPS Type-I.

3. The method of claim 1, wherein the CRPS is CRPS Type-II.

4. The method of claim 1, wherein the CRPS is warm CRPS.

5. The method of claim 1, wherein the CRPS is cold CRPS.

6. The method of claim 1, wherein the CRPS is triggered by a traumatic event.

7. The method of claim 6, wherein the traumatic event is a bone fracture.

8. The method of claim 6, wherein the traumatic event is a surgery.

9. The method of claim 6, wherein the traumatic event is a soft tissue injury.

10. The method of claim 6, wherein the traumatic event is a bone injury.

11. The method of claim 6, wherein the traumatic event is a nerve injury.

12. The method of claim 6, wherein the traumatic event is a sprain.

13. The method of claim 6, wherein the traumatic event is a crush.

14. The method of claim 6, wherein the traumatic event is a contusion.

15. The method of claim 6, wherein the traumatic event is a dislocation.

16. The method of claim 6, wherein the traumatic event is a scratch.

17. The method of claim 6, wherein the traumatic event is a skin puncture.

18. The method of claim 1, wherein on the day before the neridronic acid is first administered, the human being has an average pain intensity score of at least 5 on the 0-10 NRS.

19. The method of claim 1, wherein on the day before the neridronic acid is first administered, the human being has an average pain intensity score of at least 6 on the 0-10 NRS.

20. The method of claim 1, wherein on the day before the neridronic acid is first administered, the human being has an average pain intensity score of at least 7 on the 0-10 NRS.

21. The method of claim 1, wherein on the day before the neridronic acid is first administered, the human being has an average pain intensity score of at least 8 on the 0-10 NRS.

22. The method of claim 1, wherein on the day before the neridronic acid is first administered, the human being has an average pain intensity score of at least 9 on the 0-10 NRS.

23. The method of claim 1, wherein at 12 weeks from the first day that the neridronic acid is administered to the human being, the human being has an average pain intensity score that is at least about 30% lower than the average pain intensity score at baseline.

24. The method of claim 1, wherein at 12 weeks from the first day that the neridronic acid is administered to the human being, the human being has an average pain intensity score that is at least about 50% lower than the average pain intensity score at baseline.

25. The method of claim 1, wherein the human being has suffered from the CRPS for less than 2 years on the first day that the neridronic acid is administered to the human being.

26. The method of claim 1, wherein the human being has suffered from the CRPS for about 2 years to about 4 years on the first day that the neridronic acid is administered to the human being.

27. The method of claim 1, wherein the human being has suffered from the CRPS for about 4 years to about 6 years on the first day that the neridronic acid is administered to the human being.

28. The method of claim 1, wherein the human being has suffered from the CRPS for about 6 years to about 10 years on the first day that the neridronic acid is administered to the human being.

\* \* \* \* \*

UNITED STATES PATENT AND TRADEMARK OFFICE
CERTIFICATE OF CORRECTION

PATENT NO. : 10,413,561 B2  
APPLICATION NO. : 16/366818  
DATED : September 17, 2019  
INVENTOR(S) : Herriot Tabuteau Page 1 of 1

It is certified that error appears in the above-identified patent and that said Letters Patent is hereby corrected as shown below:

On the Title Page

Page 2
Item [63], Line 11: delete "which" and replace with --; application No. 15/357,932--
Item [63], Line 19: delete "which" and replace with --; application No. 15/384,125--
Item [63], Line 25: delete "which" and replace with --; this application--

Signed and Sealed this
Sixteenth Day of June, 2020

Andrei Iancu
*Director of the United States Patent and Trademark Office*